United States Patent
Kataoka et al.

(10) Patent No.: US 10,471,019 B2
(45) Date of Patent: *Nov. 12, 2019

(54) SUBSTANCE-CONTAINING VESICLE, AND PRODUCTION METHOD THEREFOR

(71) Applicant: JAPAN SCIENCE AND TECHNOLOGY AGENCY, Kawaguchi-shi, Saitama (JP)

(72) Inventors: Kazunori Kataoka, Tokyo (JP); Akihiro Kishimura, Tokyo (JP); Yasutaka Anraku, Tokyo (JP); Akinori Goto, Tokyo (JP)

(73) Assignee: JAPAN SCIENCE AND TECHNOLOGY AGENCY, Kawaguchi-shi (JP)

( * ) Notice: Subject to any disclaimer, the term of this patent is extended or adjusted under 35 U.S.C. 154(b) by 0 days.

This patent is subject to a terminal disclaimer.

(21) Appl. No.: 15/683,988

(22) Filed: Aug. 23, 2017

(65) Prior Publication Data

US 2018/0008549 A1 Jan. 11, 2018

Related U.S. Application Data

(63) Continuation of application No. 14/839,854, filed on Aug. 28, 2015, now Pat. No. 9,782,358, which is a
(Continued)

(30) Foreign Application Priority Data

Mar. 1, 2013 (JP) .................................. 2013-041186
Aug. 27, 2013 (JP) .................................. 2013-176068

(51) Int. Cl.
*A61K 9/51* (2006.01)
*A61K 9/10* (2006.01)
(Continued)

(52) U.S. Cl.
CPC .............. *A61K 9/5146* (2013.01); *A61K 9/10* (2013.01); *A61K 9/5123* (2013.01); *B01J 13/14* (2013.01);
(Continued)

(58) Field of Classification Search
None
See application file for complete search history.

(56) References Cited

U.S. PATENT DOCUMENTS 7,498,045 B2  3/2009  Chang et al.
8,304,497 B2  11/2012  Kataoka et al.
(Continued)

FOREIGN PATENT DOCUMENTS

EP  1878766 A1  1/2008
JP  2001-146556 A1  11/2002
(Continued)

OTHER PUBLICATIONS

Non-Final Office Action dated Jul. 2, 2018 in U.S. Appl. No. 15/660,746.
(Continued)

*Primary Examiner* — Robert A Wax
*Assistant Examiner* — Melissa S Mercier
(74) *Attorney, Agent, or Firm* — Perkins Coie LLP; Viola T. Kung

(57) ABSTRACT

Provided is a monodisperse agglomerate of a substance-containing vesicle filled with a substance at a concentration higher than conventionally possible. A mixed solution, in which a target substance is included in an aqueous medium, is mixed with a monodisperse agglomerate of a crosslinked vesicle comprising a prescribed polymer which includes a first polymer, i.e. a block copolymer having uncharged hydrophilic segments and first charged segments, and a second polymer having second charged segments carrying a
(Continued)

(a)

(b)

charge opposite to that of the first charged segments, and in which the first polymer and/or the second polymer are/is crosslinked. As a result, the crosslinked vesicle is made to contain the target substance.

21 Claims, 37 Drawing Sheets

Related U.S. Application Data continuation of application No. PCT/JP2014/055186, filed on Feb. 28, 2014.

(51) Int. Cl.
  *B01J 13/14* (2006.01)
  *C08G 69/10* (2006.01)
  *C08G 69/40* (2006.01)
  *C08L 77/04* (2006.01)
(52) U.S. Cl.
  CPC .............. *C08G 69/10* (2013.01); *C08G 69/40* (2013.01); *C08L 77/04* (2013.01)

(56) References Cited

U.S. PATENT DOCUMENTS

| 9,051,437 | B2 | 6/2015 | Kishimura et al. |
| 9,314,529 | B2 | 4/2016 | Kataoka et al. |
| 9,750,687 | B2* | 9/2017 | Kataoka ............... A61K 9/1273 |
| 9,782,358 | B2 | 10/2017 | Kataoka et al. |
| 9,808,480 | B2 | 11/2017 | Kataoka et al. |
| 10,322,092 | B2* | 6/2019 | Kataoka ............... A61K 9/5146 |
| 2005/0003016 | A1 | 1/2005 | Discher et al. |
| 2009/0081458 | A1 | 3/2009 | Kataoka |
| 2013/0202711 | A1 | 8/2013 | Kataoka |

FOREIGN PATENT DOCUMENTS

| WO | 2011/145745 A1 | 11/2011 |
| WO | 2012/014942 A1 | 2/2012 |
| WO | 2014/058079 A1 | 4/2014 |

OTHER PUBLICATIONS

Anraku, Yasutaka et al., "PCI-gata Vesicle no Tokucho o Ikashita Koso Prodrug Ryoho-yo Carrier no Kochiku", Polymer Preprints, Japan, vol. 62, No. 1, May 14, 2013 (May 14, 2013), p. 1885 (1Pe141).

Kishimura, Akihiro et al., "Busshitsu Tokasei Kobunshi Capsule PICsome no Kaihatsu to sono DDS Oyo", The Pharmaceutical Society of Japan Dai 133 Nenkai DVD Yoshishu, Apr. 25, 2013 (Apr. 25, 2013) (received date), 28Q-pm15.

International Search Report for International Application No. PCT/JP2014/055186, dated Jun. 3, 2014.

European Search Report dated Aug. 10, 2016 in EP Application No. 14757219.2.

* cited by examiner

FIG. 1
(a)
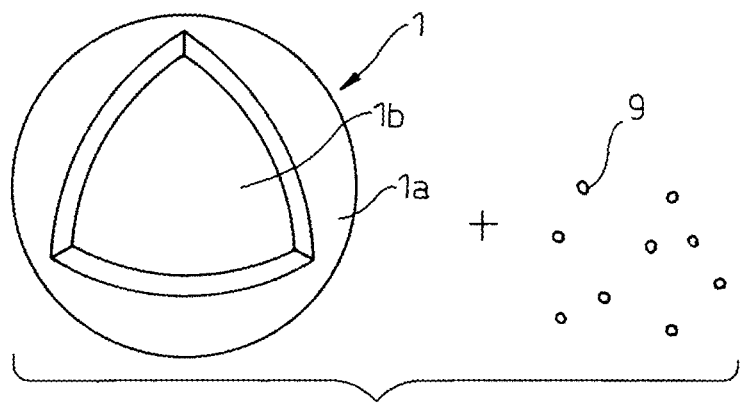
(b)
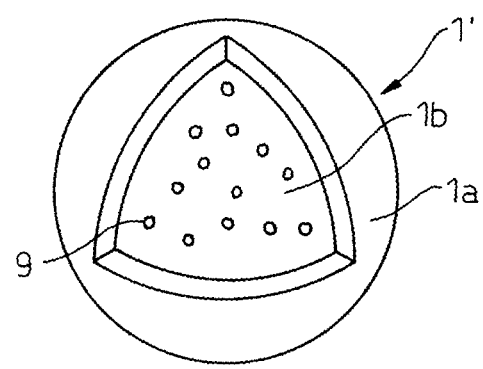

FIG. 2
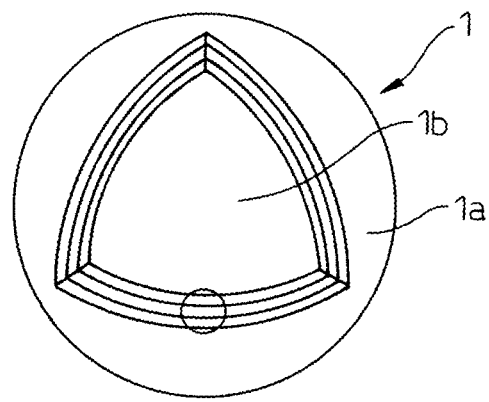
FIG. 3
(a)
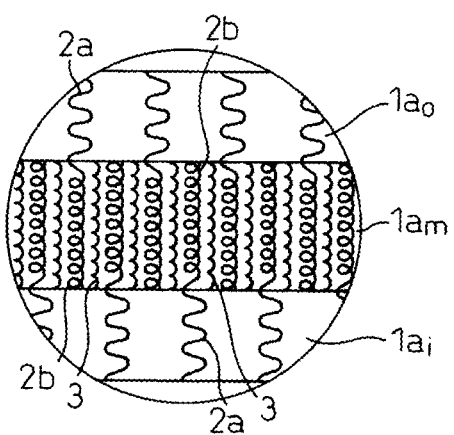
(b)
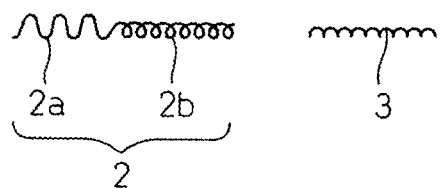

FIG. 4
(a)
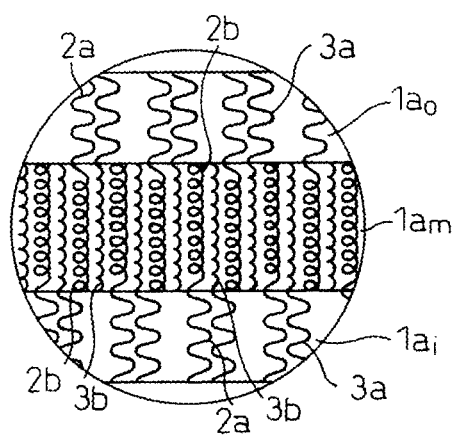
(b)
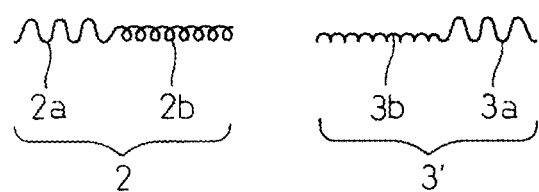

(Size:97.2nm, PDI:0.087)

(Size:627.5nm, PDI:0.619)

(Size:561.9nm, PDI:0.565)

FIG. 7
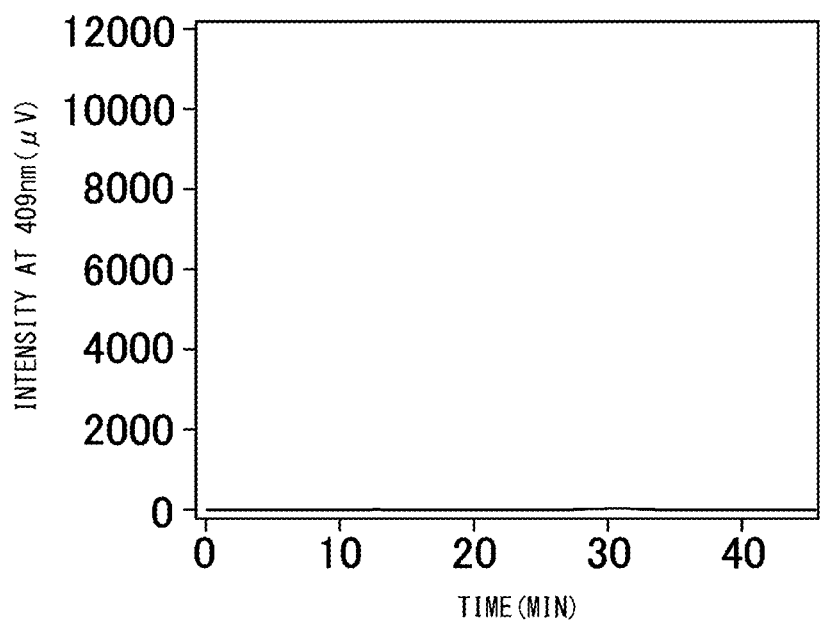
(a)
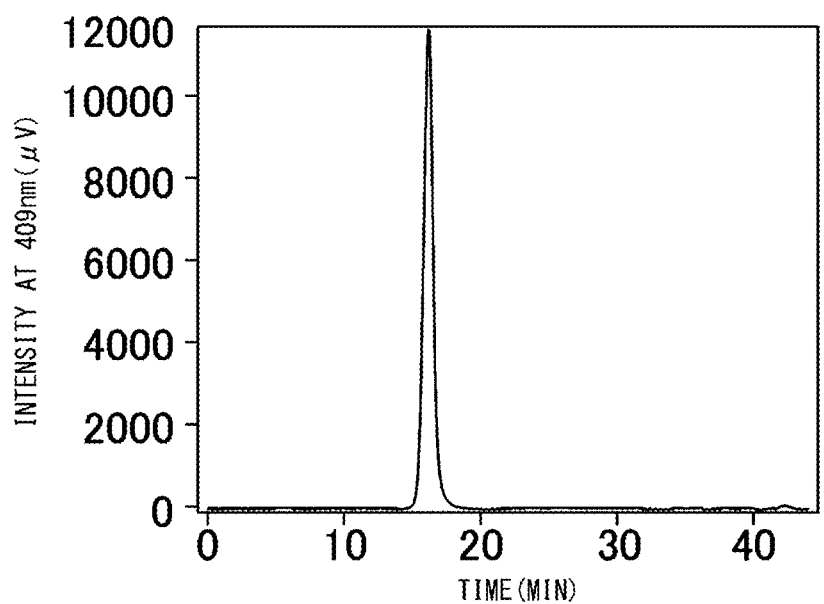
(b)

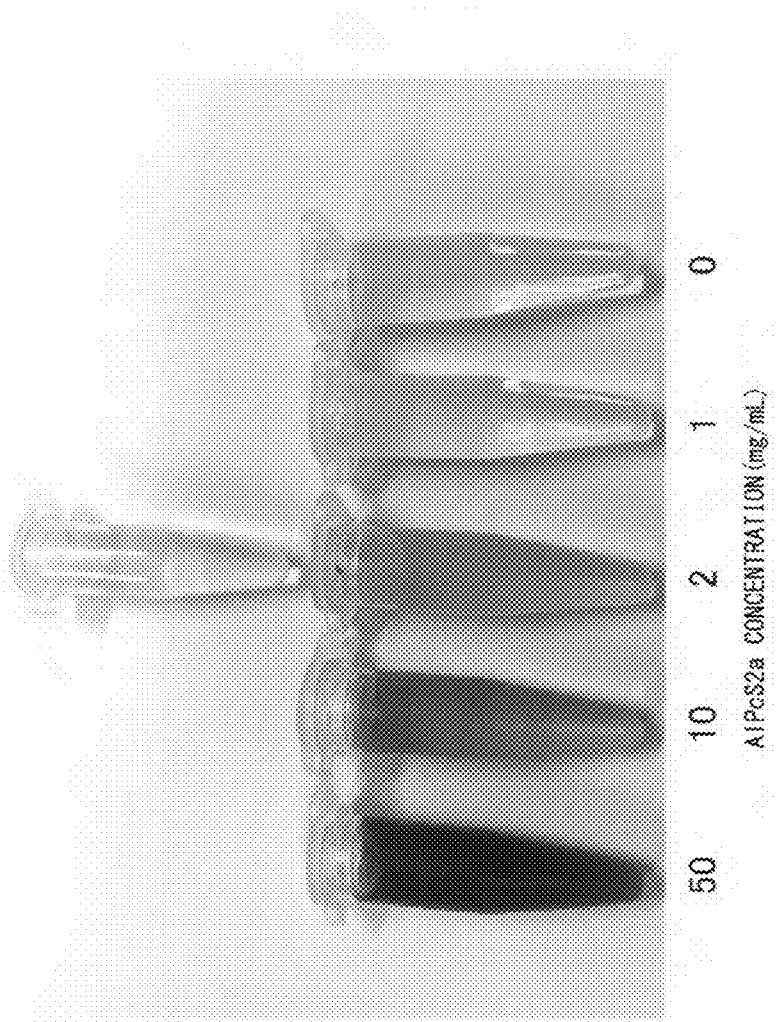

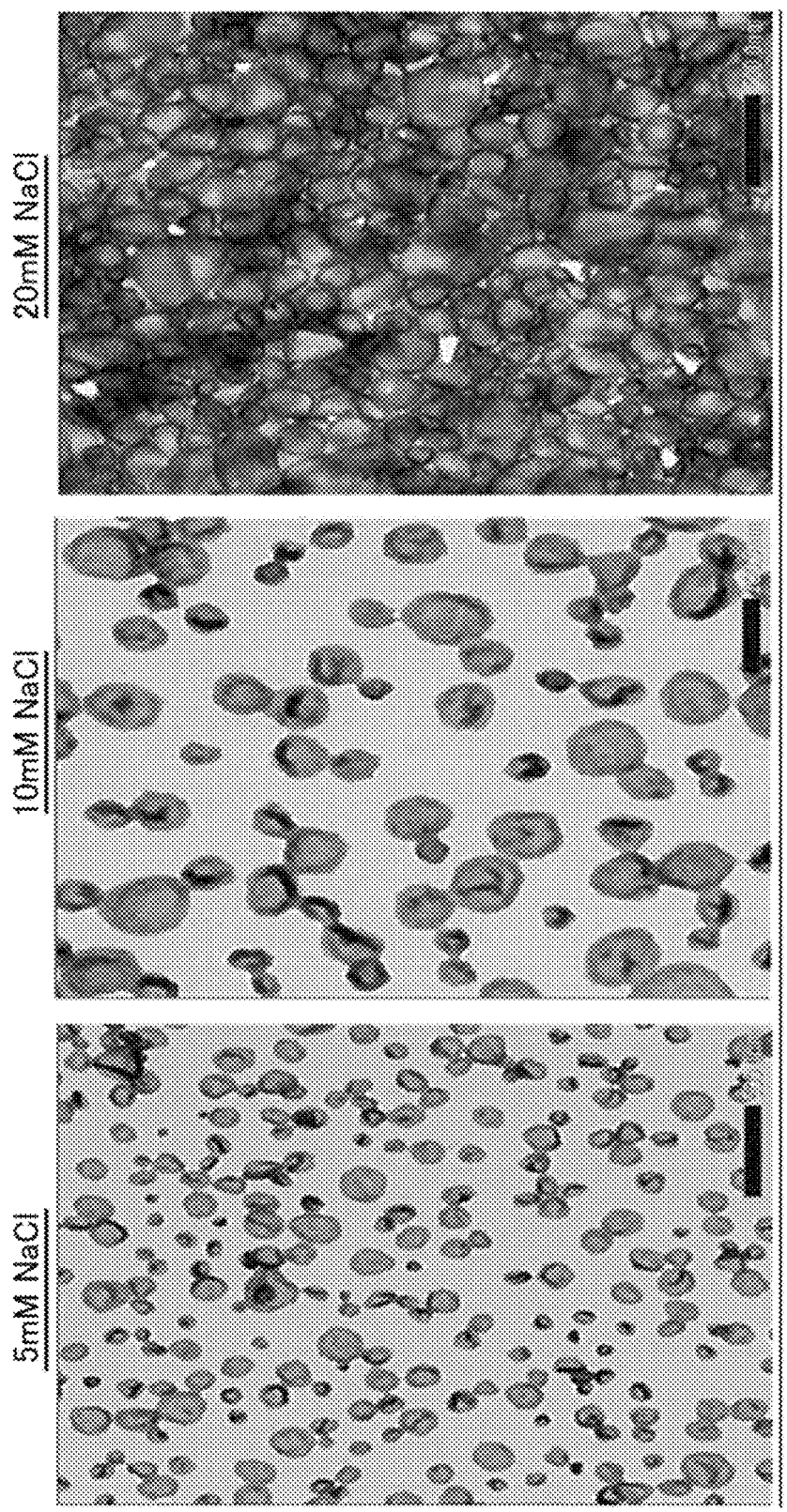

FIG. 28
(a)
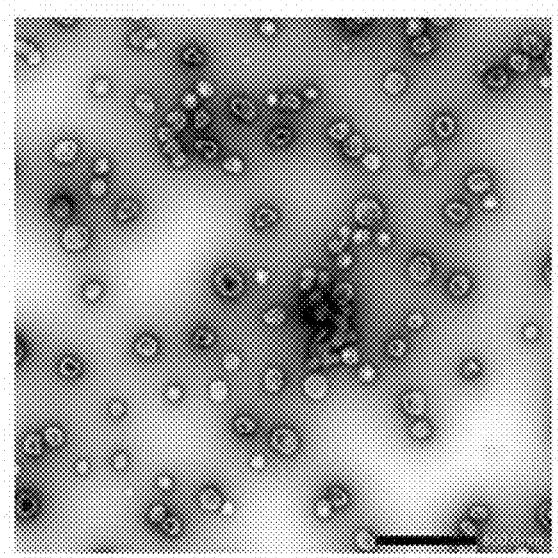
(b)
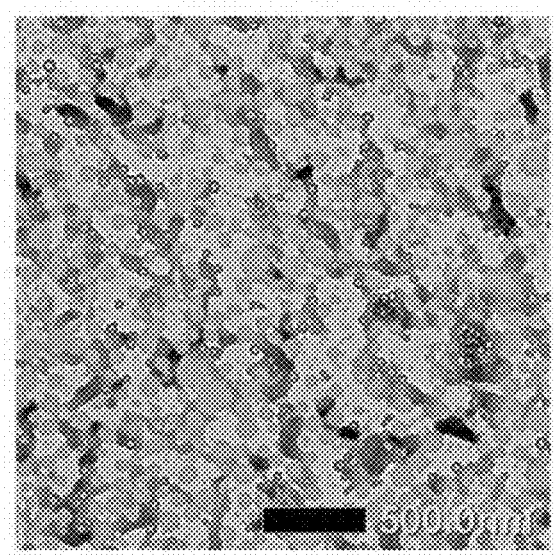

FIG. 29
(a)
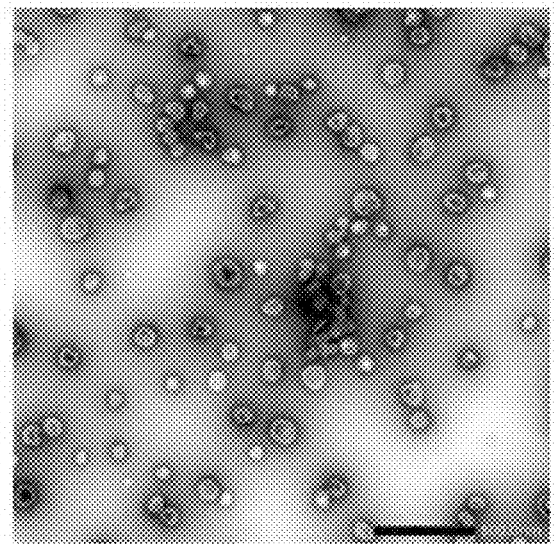
(b)
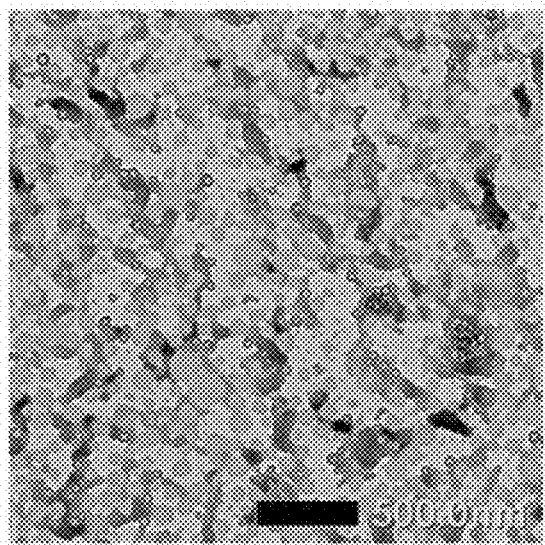

FIG. 33
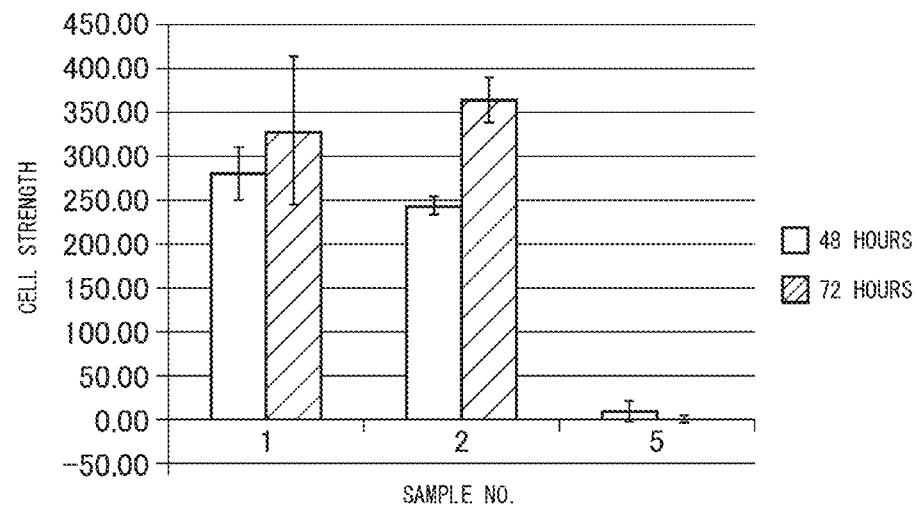
(a)
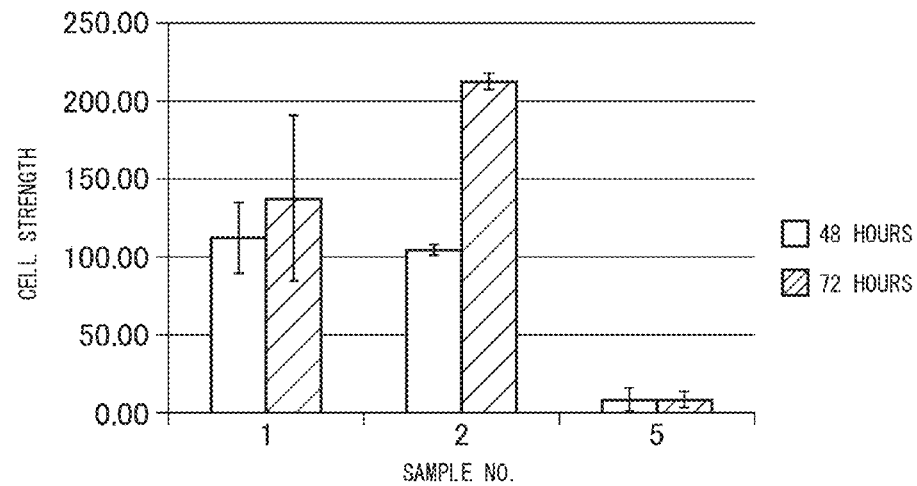
(b)

FIG. 34
(a)
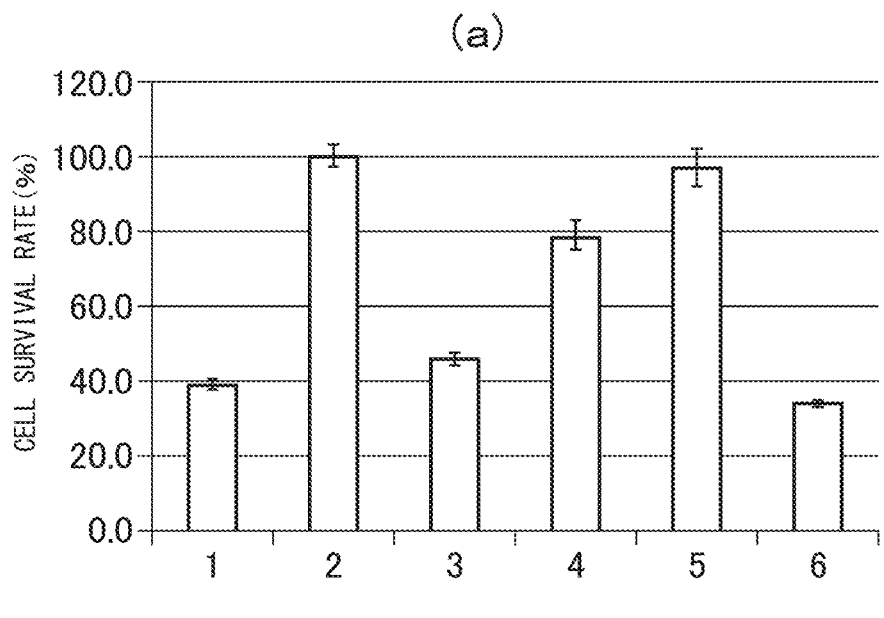
(b)
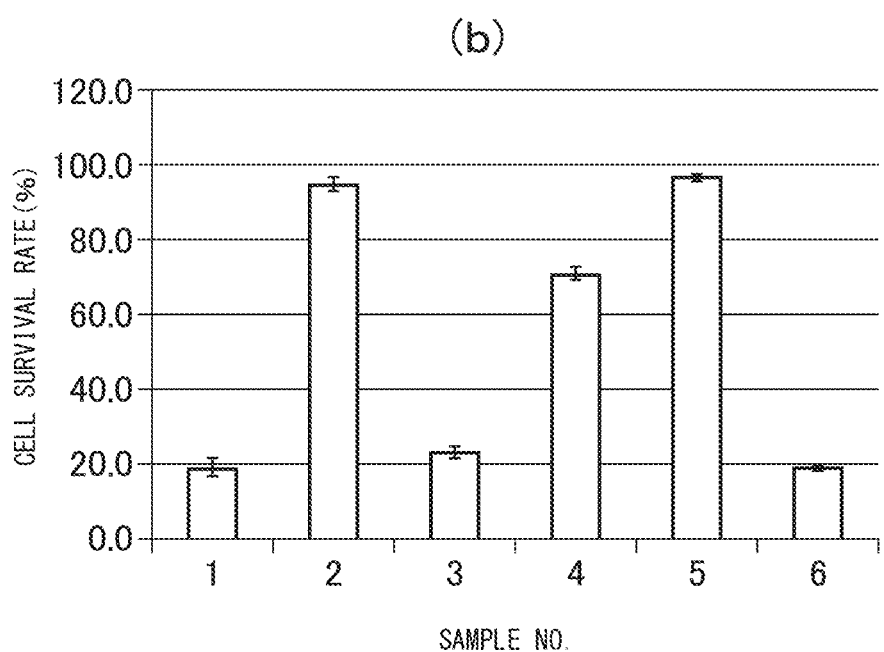

FIG. 35
(a)
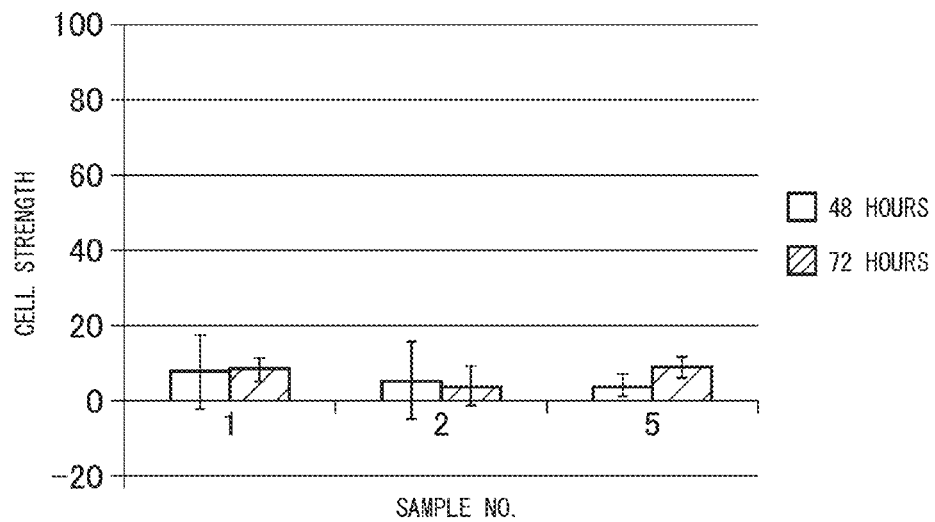
(b)
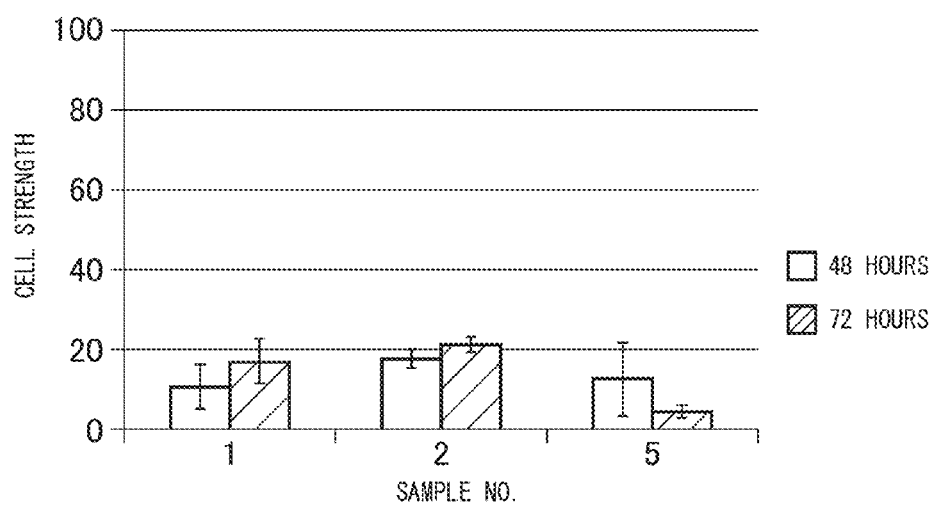

FIG. 36
(a)
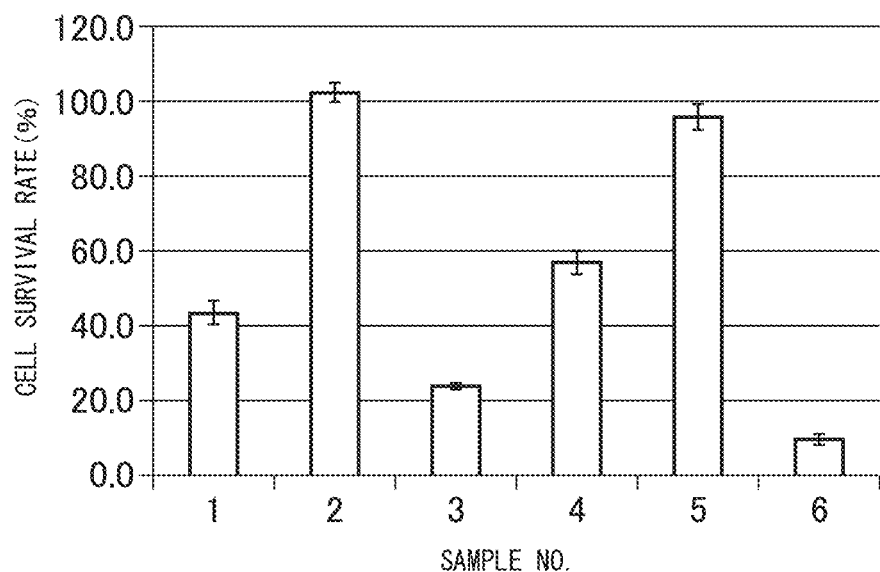
(b)
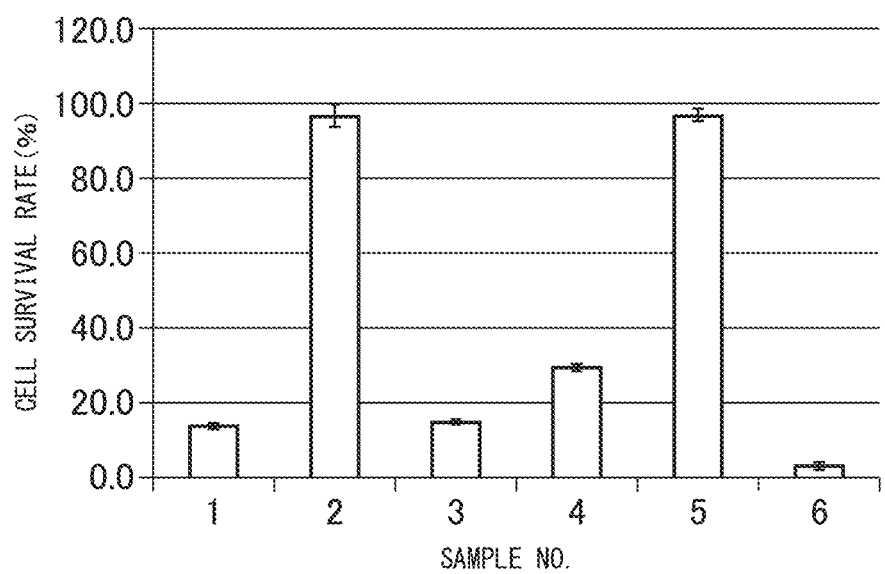

FIG. 37
(a)
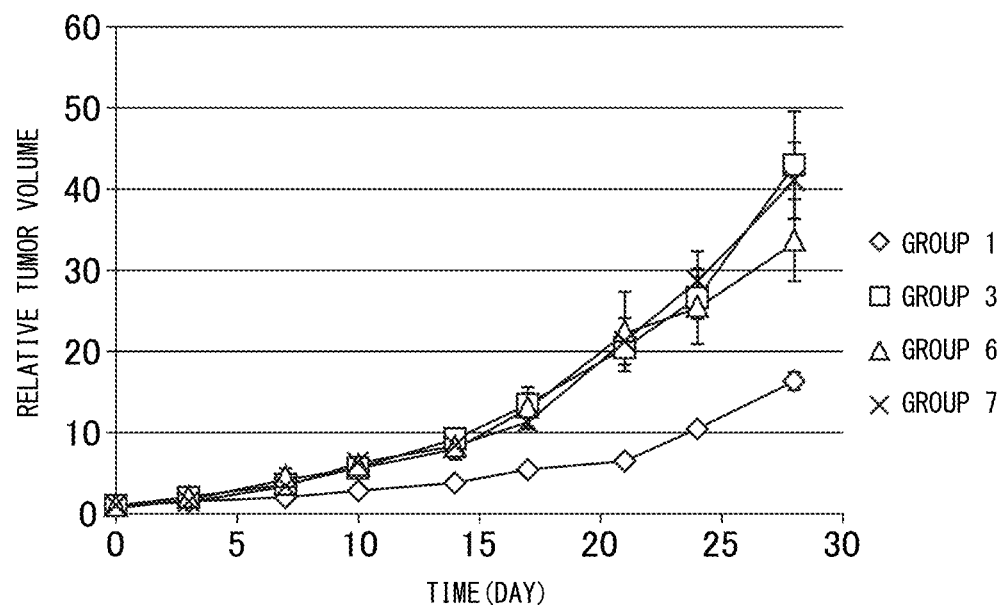
(b)
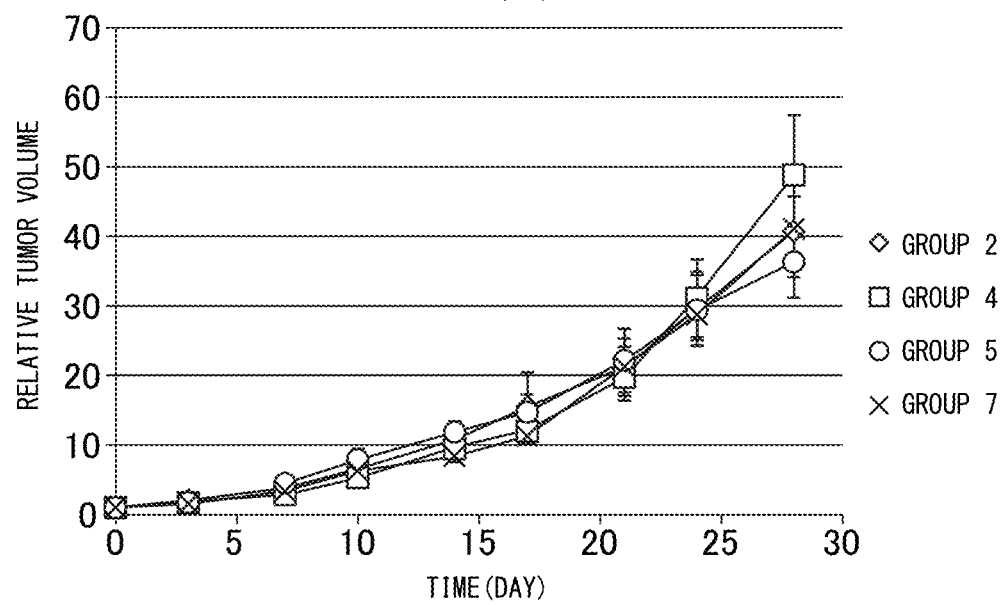

SUBSTANCE-CONTAINING VESICLE, AND PRODUCTION METHOD THEREFOR

This application is a continuation of U.S. application Ser. No. 14/839,854, filed Aug. 28, 2015; which is a continuation of PCT Application No. PCT/JP2014/055186, filed Feb. 28, 2014; which claims the priorites of Application Nos. JP 2013-041186, filed Mar. 1, 2013 and JP 2013-176068, filed Aug. 27, 2013. The contents of the above-identified applications are incorporated herein by reference in their entireties.

TECHNICAL FIELD

The present invention relates to novel substance-encapsulating vesicles as well as methods of producing the vesicles.

BACKGROUND ART

It is known that a vesicle can be formed via self-assembly of polymer molecules of which the primary structure has been have been controlled precisely. Such a vesicle is applicable to various molecular designs, and can serve a new function beyond the properties of the original polymers. Accordingly, the vesicle is being considered for use as a carrier for a drug delivery system (DDS) or as a biomaterial or functional material.

Patent Document 1 (JP-H08-188541A, of which the inventors overlap with the present inventors) discloses a drug carrier in the form of an electrostatically-united polymeric micelle formed via self-assembly of molecules of a block copolymer having an uncharged segment and a charged segment.

Non-Patent Document 1 (Schlaad H. et al., Macromolecules, 2003, 36 (5), 1417-1420) discloses a vesicle referred to as "polymersome", which is formed via self-assembly of molecules of a first block copolymer having poly(1,2-butadiene) block and poly(cesium methacrylate) block and a second block copolymer having polystyrene block and poly (1-methyl-4-vinylpyridinium iodide) block.

Patent Document 2 (WO2006/118260A, of which the inventors overlap with the present inventors) discloses a vesicle formed via self-assembly of a first block copolymer having an uncharged hydrophilic segment and a cationic segment (e.g., PEG-polycation) with a second block copolymer having an uncharged hydrophilic segment and an anionic segment (e.g., PEG-polyanion).

Non-Patent Document 2 (Anraku Y. et al., J. Am. Chem. Soc., 2010, 132 (5), 1631-1636, of which the inventors overlap with the present inventors) discloses a vesicle formed via self-assembly of a block copolymer having an uncharged hydrophilic segment and a charged segment (e.g., PEG-polycation) and a copolymer charged oppositely to the charged segment of the block copolymer (e.g., polyanion).

It is contemplated that such vesicles formed via self-assembly of polymers as mentioned above can encapsulate and carry various substances within their cavities for desired applications (for overview, see, e.g., Non-Patent Document 3: H. Nyin et al. Soft Matter, 2006, 2, 940-949; and Non-Patent Document 4: "Liposome: New Developments in Applications", supervised by Kazunari AKIYOSHI et al., NTS Inc., 2005).

A typical process of producing a vesicle encapsulating a substance within its cavity (hereinafter also referred to as "substance-encapsulating vesicle") includes mixing a substance to be encapsulated (hereinafter also referred to as "encapsulation-target substance") with membrane component polymers or a preformed polymer membrane to cause formation of a polymer vesicle via self-assembly simultaneously with enclosure of the substance into the vesicle cavity (hereinafter also referred to as "simultaneous mixing method"). Examples include: emulsion method (see, e.g., Non-Patent Document 5: F. Szoka, Jr et al., Proc. Natl. Acad. Sci. USA, 1978 75 (9) 4194-4198); and instillation method using organic solution of lipids (see, e.g., Non-Patent Document 6: Batzri, S. et al., Biochim. Biophys Acta 1973, 298, 1015-1019).

However, the simultaneous mixing method has a drawback that presence of the encapsulation-target substance may affect vesicle formation process via self-assembly, thereby preventing formation of a vesicle or, even if not, enclosure of the substance into the vesicle cavity. Another problem involved in this method is that it often requires use of organic solvent which is detrimental to membrane formation, rendering the process complicated and causing damage to the encapsulation-target substance due to the organic solvent. This method has still another drawback that it is difficult to form vesicles having uniform particle size and structure unless carrying out an additional step, which is likely to render the process complicated. Thus, this method lacks versatility, and is not practical as a means for producing various kinds of substance-encapsulating vesicles.

On the other hand, as a general method of producing a particle encapsulating a substance, there is a method in which an encapsulation-target substance is introduced into the cavity of an existing vacant particle such that the substance is enclosed and carried by the particle (hereinafter also referred to as "post-carrying method") (see, e.g., Non-Patent Document 7: W. Tong et al. J. Phys. Chem. B, 2005, 109, 13159-13165). This method could be an option for producing substance-encapsulating vesicles.

However, application of the post-carrying method to vesicles would require any additional means to introduce an encapsulation-target substance beyond the membrane of a vacant vesicle into the vesicle cavity. A conceivable method includes: making the vacant vesicle swell to relax the membrane; penetrating the encapsulation-target substance into the cavity through cleavage which has occurred on the relaxed membrane; and contracting the membrane to prevent release of the encapsulation-target substance. Another conceivable method includes: opening pores on the membrane of the vacant vesicle; introducing the encapsulation-target substance into the cavity through the pores; and closing the pores to prevent release of the encapsulation-target substance. However, these methods are cumbersome and complicated, too disadvantageous to be put into practical use. In addition, the particle size and the structure of the existing vacant vesicle would probably be disturbed during the process of enclosure and carriage of the encapsulation-target substance. Accordingly, these methods have been considered as being far from practical.

Another published method for lipid bilayer membrane vesicles such as liposomes includes integrating a channel protein into the lipid bilayer membrane (see, e.g., Non-Patent Document 8: Ranquin A, Versees W, Miere W, Steyaert J, Gelder P V., "Therapeutic Nanoreactors: Combining Chemistry and Biology in a Novel Triblock Copolymer", Drug Delivery System, Nano Lett., 2005, 5:2220-4). However, this method is not practical either, since the process is cumbersome and complicated and lacks versatility.

Under such circumstance, the present inventors filed a patent application (Patent Document 3: WO2011/145745A)

based on a surprising finding that a vacant vesicle formed of a membrane containing a first polymer, which is a block copolymer having an uncharged hydrophilic segment and a first charged segment, and a second polymer, which has a second charged segment oppositely charged to the first charged segment, wherein the membrane defines a cavity, can be used for producing a substance-encapsulating vesicle efficiently with ease by a method including mixing a vacant vesicle in aqueous medium in the presence of a target substance to be encapsulated (which method corresponds to a "post-carrying method" mentioned above), whereby the target substance is encapsulated into the vesicle cavity (inner aqueous phase) via self-assembly of the first and second polymers.

PRIOR ART REFERENCES

Patent Documents

[Patent Document 1] JP-H8-188541A
[Patent Document 2] WO2006/118260A
[Patent Document 3] WO2011/145745A Non-Patent Documents

[Non-Patent Document 1] Schlaad H. et al., Macromolecules, 2003, 36 (5), 1417-1420
[Non-Patent Document 2] Anraku Y. et al., J. Am. Chem. Soc., 2010, 132 (5), 1631-1636
[Non-Patent Document 3] H. Nyin et al. Soft Matter, 2006, 2, 940-949
[Non-Patent Document 4] "Liposome: New Developments in Applications", supervised by Kazunari AKIYOSHI et al., NTS Inc., 2005
[Non-Patent Document 5] F. Szoka, Jr. et al., Proc. Natl. Acad. Sci. USA, 1978 75 (9) 4194-4198
[Non-Patent Document 6] Batzri, S. et al., Biochim. Biophys Acta 1973, 298, 1015-1019
[Non-Patent Document 7] W. Tong et al., J. Phys. Chem. B, 2005, 109, 13159-13165
[Non-Patent Document 8] Ranquin A et al., Nano Lett. 2005, 5:2220-4

DISCLOSURE OF THE INVENTION

Problems to be Solved by the Invention

However, according to the conventional methods such as the post-carrying method, if a monodisperse population of vacant vesicles is mixed for encapsulation with a target substance present in aqueous medium in a concentration higher than a certain value, the monodispersity of the vesicles is disturbed, and the resultant substance-encapsulating vesicles become to form a polydisperse population.

In addition, encapsulation of a target substance into a vacant vesicle occurs as a statistical event depending on the concentration of the target substance present in aqueous medium. Accordingly, it is difficult to encapsulate two or more target substances into a vacant vesicle with controlling the encapsulation amount by the conventional methods such as the post-carrying method.

Furthermore, electrostatic interaction-type vesicles prepared by the conventional methods have limitations to the size of substances that can be encapsulated into the vesicle. Specifically, the maximum size of a substance to be encapsulated is limited to about 2 to 30 nm, while no vesicles encapsulating particles having a larger size (e.g., larger than 30 nm) have been obtained yet. In addition, since normal electrostatic interaction-type vesicles exhibit semipermeable membrane properties, the lower limit of the size of a substance to be encapsulated is defined as a molecular weight of about some thousands or higher, while it is very difficult to encapsulate a low-molecular compound having a lower molecular weight.

Moreover, the encapsulation rate of a substance into a conventional electrostatic interaction-type vesicle depends partly on the physicochemical properties of the substance to be encapsulated, but is basically limited to a level achieved via probability depending on the concentration of the substance to be encapsulated in solution for mixture with the vesicle. It is very difficult to encapsulate a substance into a vesicle with a higher efficiency. Specifically, the size of the substance to be encapsulated is significantly larger than the size of the vesicle (e.g., when encapsulating, into a vesicle having a size of about 100 nm, particles with a size of about 10 nm (about one tenth) or larger), the resultant encapsulation efficiency becomes very low, often leaving a large amount of the substance and without being encapsulated and also leaving a large number of vacant vesicles.

In addition, according to the conventional methods for preparing electrostatic interaction-type vesicles, vesicles (or polymers as components thereof) are mixed with the substance to be encapsulated in aqueous medium to thereby encapsulate the substance into the vesicles. Therefore, it is very difficult to efficiently encapsulate into vesicles a substance which exhibits poor solubility into aqueous medium (poorly water-soluble substance).

Thus, a first objective of the present invention is to provide a monodisperse population of substance-encapsulating vesicles encapsulating a target substance at a concentration higher than that achieved by the conventional methods (e.g., at a concentration which prevents formation of a monodisperse population of substance-encapsulating vesicles by the post-carrying method), as well as a method of producing a substance-encapsulating vesicle which allows for production of a monodisperse population of substance-encapsulating vesicles encapsulating a target substance at a concentration higher than that achieved by the conventional methods (e.g., at a concentration which prevents formation of a monodisperse population of substance-encapsulating vesicles by the post-carrying method).

A second objective of the present invention is to provide a substance-encapsulating vesicle encapsulating two or more target substances with controlled encapsulation amounts, as well as a method of producing a substance-encapsulating vesicle which allows for encapsulation of two or more target substance into vesicles with controlling the encapsulation amounts thereof.

A third objective of the present invention is to provide a method of producing a substance-encapsulating vesicle which can efficiently encapsulate, into an electrostatic interaction-type vesicle formed via self-assembly of polymers, particles having a larger size or a compound with a lower molecular weight with improved encapsulation efficiency compared with the conventional methods.

A fourth objective of the present invention is to provide a method of producing a substance-encapsulating vesicle which can efficiently encapsulate, into an electrostatic interaction-type vesicle formed via self-assembly of polymers, a substance which is insoluble or poorly soluble to aqueous medium.

Means to Solve the Problems

Aspects of the present invention reside in the following:
[1] A monodisperse population of substance-encapsulating crosslinked vesicles, each of the substance-encapsulating crosslinked vesicles comprising:
a crosslinked membrane comprising a first polymer, which is block copolymer having an uncharged hydrophilic segment and a first charged segment, and a second polymer, which has a second charged segment having a charge opposite to the charge of the first charged segment, the first and/or the second polymer(s) being crosslinked;
an inner aqueous phase surrounded by the crosslinked membrane; and
a target substance encapsulated in the inner aqueous phase,
wherein the concentration of the target substance encapsulated in the inner aqueous phase is high enough to prevent formation of a monodisperse population of substance-encapsulating non-crosslinked vesicles each encapsulating the target substance when a monodisperse population of vacant non-crosslinked vesicles is mixed with a mixture liquid containing the target substance in an aqueous medium at the same concentration as the concentration of the substance-encapsulating crosslinked vesicle in the inner aqueous phase, wherein the monodisperse population of vacant non-crosslinked vesicles differs from the monodisperse population of substance-encapsulating crosslinked vesicles only in that the first and/or the second polymer(s) is(are) not crosslinked and that the target substance is not encapsulated.
[2] The monodisperse population of substance-encapsulating crosslinked vesicles according to [1], having a polydispersity index of 0.2 or lower.
[3] The monodisperse population of substance-encapsulating crosslinked vesicles according to [1] or [2], wherein the weight-average molecular weight of the target substance is between 10000 and 40000, and the concentration of the target substance contained in the inner aqueous phase is higher than 5 mg/mL.
[4] The monodisperse population of substance-encapsulating crosslinked vesicles according to [2], wherein the first and/or the second polymer(s) is(are) crosslinked with one or more crosslinking bonds selected from the group consisting of a crosslinking bond formed between cationic groups, a crosslinking bond formed between anionic groups, and a crosslinking bond formed between a cationic group and an anionic group, and the molar ratio of the cationic groups and/or anionic groups forming crosslinking bonds to the cationic groups and/or anionic groups contained in the crosslinked membrane is 35% or more.
[5] A substance-encapsulating crosslinked vesicles comprising:
a crosslinked membrane comprising a first polymer, which is block copolymer having an uncharged hydrophilic segment and a first charged segment, and a second polymer, which has a second charged segment having a charge opposite to the charge of the first charged segment, the first and/or the second polymer(s) being crosslinked;
an inner aqueous phase surrounded by the crosslinked membrane; and
a first target substance and a second target substance encapsulated in the inner aqueous phase, the first target substance having a smaller molecular weight than the molecular weight of the second target substance,
wherein the first target substance is more stable than when the first target substance is contained in the inner aqueous phase in the absence of the second target substance.
[6] The substance-encapsulating crosslinked vesicle according to [5], wherein the second target substance is a clouding agent.
[7] A method of producing a substance-encapsulating vesicle, comprising mixing a monodisperse population of vacant crosslinked vesicles with a mixture liquid containing the target substance in an aqueous medium to form a monodisperse population of substance-encapsulating crosslinked vesicles,
wherein each of the vacant crosslinked vesicles comprises: a crosslinked membrane comprising a first polymer, which is block copolymer having an uncharged hydrophilic segment and a first charged segment, and a second polymer, which has a second charged segment having a charge opposite to the charge of the first charged segment, the first and/or the second polymer(s) being crosslinked; and an inner aqueous phase surrounded by the crosslinked membrane, wherein the inner aqueous phase does not contain the target substance, and
wherein each of the substance-encapsulating crosslinked vesicles comprises: the crosslinked membrane comprising the first polymer and the second polymer, the first and/or the second polymer(s) being crosslinked; and the inner aqueous phase surrounded by the crosslinked membrane, wherein the inner aqueous phase contains the target substance.
[8] The method according to [7], wherein the monodisperse population of vacant crosslinked vesicles, the monodisperse population of substance-encapsulating crosslinked vesicles, the monodisperse population of vacant non-crosslinked vesicles, and the monodisperse population of substance-encapsulating non-crosslinked vesicles each have a polydispersity index of 0.2 or less.
[9] The method according to [7] or [8], wherein the weight-average molecular weight of the target substance is between 10000 and 40000, and the concentration of the target substance in the mixture liquid is more than 5 mg/mL.
[10] The method according to [9], wherein both in the vacant crosslinked vesicles and the substance-encapsulating crosslinked vesicles, the first and/or the second polymer(s) is(are) crosslinked with one or more crosslinking bonds selected from the group consisting of a crosslinking bond formed between cationic groups, a crosslinking bond formed between anionic groups, and a crosslinking bond formed between a cationic group and an anionic group, and the molar ratio of the cationic groups and/or anionic groups forming crosslinking bonds to the cationic groups and/or anionic groups contained in the crosslinked membrane is 35% or more.
[11] The method according to any one of [7] to [10], further comprising: reacting the monodisperse population of substance-encapsulating crosslinked vesicles with a crosslinker which can react with the first and/or the second polymer(s).
[12] A method of producing a substance-encapsulating vesicle, comprising:
mixing a first substance-encapsulating crosslinked vesicle, which encapsulates a first substance, with a mixture liquid containing a second target substance in an aqueous medium to form a second substance-encapsulating crosslinked vesicle, which encapsulates the first substance,
wherein the first substance-encapsulating crosslinked vesicle comprises: a crosslinked membrane comprising a first polymer, which is block copolymer having an uncharged hydrophilic segment and a first charged segment, and a second polymer, which has a second charged segment having a charge opposite to the charge of the first charged segment, the first and/or the second polymer(s) being crosslinked; and an inner aqueous phase surrounded by the crosslinked membrane, wherein the inner aqueous phase contains the first target substance, and wherein the second substance-encapsulating crosslinked vesicle comprises: the crosslinked membrane comprising the first polymer and the second polymer, the first and/or the second polymer(s) being crosslinked; and the inner aqueous phase surrounded by the crosslinked membrane, wherein the inner aqueous phase contains the first and second substances.

[13] The method according to [12], wherein a monodisperse population of the first substance-encapsulating crosslinked vesicles is used to thereby produce a monodisperse population of the second substance-encapsulating crosslinked vesicles.

[14] The method according to [13], wherein the concentration of the second target substance contained in the mixture liquid is high enough to prevent formation of a monodisperse population of substance-encapsulating non-crosslinked vesicles each encapsulating both the first and second target substances when a monodisperse population of first non-crosslinked vesicles is mixed with the mixture liquid, wherein the monodisperse population of first substance-encapsulating non-crosslinked vesicles differs from the monodisperse population of first substance-encapsulating crosslinked vesicles only in that the first and/or the second polymer(s) is(are) not crosslinked.

[15] The method according to any one of [12] to [14], further comprising forming the first substance-encapsulating crosslinked vesicle by contacting a vacant crosslinked vesicle a mixture liquid containing the first target substance in an aqueous medium, wherein the vacant crosslinked vesicle comprises a crosslinked membrane comprising: the first and second polymers wherein the first and/or the second polymer(s) is(are) crosslinked; and an inner aqueous phase surrounded by the crosslinked membrane, wherein the inner aqueous phase does not contain the first and second target substances; and if necessary, reacting the vesicle with a crosslinker which can react with the first and/or the second polymer(s).

[16] The method according to [15], wherein a monodisperse population of the vacant crosslinked vesicles is used to thereby produce a monodisperse population of the first substance-encapsulating crosslinked vesicles.

[17] The method according to [16], wherein the concentration of the first target substance contained in the mixture liquid is high enough to inhibit the formation of a monodisperse population of substance-encapsulating non-crosslinked vesicles containing the first target substance when a monodisperse population of vacant non-crosslinked vesicles is mixed with the mixture liquid, wherein the monodisperse population of vacant non-crosslinked vesicles differs from the monodisperse population of vacant crosslinked vesicles only in that the first and/or the second polymer(s) are not crosslinked.

[18] The method according to any one of [12] to [17], wherein the second target substance is a clouding agent.

[19] An adsorbent-encapsulating vesicle comprising:

a vesicle composed of a membrane comprising a first polymer, which is block copolymer having an uncharged hydrophilic segment and a first charged segment, and a second polymer, which has a second charged segment having a charge opposite to the charge of the first charged segment; and an adsorbent particle encapsulated in the vesicle, wherein at least either the first polymer or the second polymer is adsorbed by the adsorbent particle.

[20] The adsorbent-encapsulating vesicle according to [19], wherein the first and/or second polymer(s) is(are) crosslinked.

[21] The adsorbent-encapsulating vesicle according to [19] or [20], wherein the adsorbent particle is a silica particle.

[22] The adsorbent-encapsulating vesicle according to any one of [19] to [21], wherein the adsorbent particle has an average particle size of between 40 nm and 10 µm.

[23] The adsorbent-encapsulating vesicle according to any one of [19] to [22], wherein the adsorbent particle has been surface-treated.

[24] The adsorbent-encapsulating vesicle according to any one of [19] to [23], wherein a low-molecular compound is adsorbed by the adsorbent particle.

[25] A method of producing an adsorbent-encapsulating vesicle comprising a vesicle composed of a membrane comprising a first polymer, which is block copolymer having an uncharged hydrophilic segment and a first charged segment, and a second polymer, which has a second charged segment having a charge opposite to the charge of the first charged segment, and an adsorbent particle encapsulated in the vesicle, said method comprising the steps of:

(a) mixing one of the first and second polymers with the adsorbent particle to have the one of the first and second polymers adsorbed by the adsorbent particle; and (b) further mixing the mixture from step (a) with the other of the first and second polymers to form a vesicle composed of a membrane comprising the first and second polymers around the adsorbent particle, thereby forming the adsorbent-encapsulating vesicle.

[26] The method according to [25], further comprising:

(c) crosslinking the first and/or the second polymer(s) contained in the vesicle from step (b).

[27] The method according to [25] or [26], wherein the adsorbent particle is a silica particle.

[28] The method according to any one of [25] to [27], wherein the adsorbent particle has an average particle size of between 40 nm and 10 µm.

[29] The method according to any one of [25] to [28], further comprising the step of surface-treating the adsorbent particle.

[30] The method according to any one of [25] to [29], wherein a low-molecular compound is adsorbed by the adsorbent particle.

[31] A method of producing a substance-encapsulating vesicle comprising: a vesicle composed of a membrane comprising a first polymer, which is block copolymer having an uncharged hydrophilic segment and a first charged segment, and a second polymer, which has a second charged segment having a charge opposite to the charge of the first charged segment; and a target substance encapsulated by the vesicle, said method comprising the steps of:

(a) preparing an enzyme-encapsulating vesicle comprising a vesicle composed of a membrane containing the first and second polymers and an enzyme encapsulated in the vesicle, wherein the vesicle can convert a precursor, which has a higher water-solubility than the target substance, into the target substance; and (b) introducing the precursor into the enzyme-encapsulating vesicle under conditions which exhibit a lower solubility for the target substance than for the precursor such that the enzyme converts the precursor into the target substance to thereby cause the target substance to precipitate and be encapsulated in the enzyme-encapsulating vesicle, thereby forming the substance-encapsulating vesicle.

[32] The method according to [31], wherein the introduction of the precursor into the enzyme-encapsulating vesicle in step (b) is carried out by mixing the enzyme-encapsulating vesicle with an aqueous solution of the precursor.

[33] The method according to [32], further comprising crosslinking the first and/or the second polymer(s) of the enzyme-encapsulating vesicle before step (b).

[34] The substance-encapsulating vesicle produced by the method according to any one of [31] to [33].

[35] A low-water-solubility substance-encapsulating vesicle comprising:
a vesicle composed of a membrane comprising a first polymer, which is block copolymer having an uncharged hydrophilic segment and a first charged segment, and a second polymer, which has a second charged segment having a charge opposite to the charge of the first charged segment;
a low-water-solubility substance encapsulated in the vesicle, wherein the low-water-solubility substance can be converted from a precursor, which has a higher water-solubility than the target substance; and
an enzyme encapsulated in the vesicle, wherein the enzyme can convert the precursor into the low-water-solubility substance.

[36] The low-water-solubility substance-encapsulating vesicle according to [34] or [35], wherein the low-water-solubility substance is encapsulated at a concentration exceeding the solubility of the low-water-solubility substance to the inner aqueous phase.

[37] The low-water-solubility substance-encapsulating vesicle according to any one of [34] to [36], wherein the first and/or the second polymer(s) is(are) crosslinked.

[38] A drug delivery system comprising the monodisperse population of vesicles according to any one of claims 1 to 4 and/or the vesicles according to any one of [5], [6], [19] to [22], and [34] to [37].

[39] A method of delivering a drug to a subject, comprising the steps of:
(a) preparing an enzyme-encapsulating vesicle comprising a vesicle composed of a membrane comprising a first polymer, which is block copolymer having an uncharged hydrophilic segment and a first charged segment, and a second polymer, which has a second charged segment having a charge opposite to the charge of the first charged segment, and an enzyme which can convert a precursor of the drug into the drug; and
(b) forming the drug by introducing the precursor into the enzyme-encapsulating vesicle at a predetermined position in the subject such that the enzyme converts the precursor into the drug.

[40] The method according to [39], wherein the precursor has a lower water-solubility than the drug, and the precursor is introduced into the enzyme-encapsulating vesicle in step (b) under conditions which exhibit a lower solubility for the drug than for the precursor.

[41] The method according to [39] or [40], wherein step (b) further comprises allowing the drug to precipitate and be encapsulated in the enzyme-encapsulating vesicle, thereby forming a drug-encapsulating vesicle.

Effects of the Invention

A first aspect of the present invention provides a monodisperse population of substance-encapsulating vesicles encapsulating a target substance at a concentration higher than that achieved by the conventional methods (e.g., at a concentration which prevents formation of a monodisperse population of substance-encapsulating vesicles by the post-carrying method), as well as a method of producing a substance-encapsulating vesicle which allows for production of a monodisperse population of substance-encapsulating vesicles encapsulating a target substance at a concentration higher than that achieved by the conventional methods (e.g., at a concentration which prevents formation of a monodisperse population of substance-encapsulating vesicles by the post-carrying method).

A second aspect of the present invention provides a substance-encapsulating vesicle encapsulating two or more target substances with controlled encapsulation amounts, as well as a method of producing a substance-encapsulating vesicle which allows for encapsulation of two or more target substance into vesicles with controlling the encapsulation amounts thereof.

A third aspect of the present invention provides a method of producing a substance-encapsulating vesicle which can efficiently encapsulate, into an electrostatic interaction-type vesicle formed via self-assembly of polymers, particles having a larger size or a compound with a lower molecular weight with improved encapsulation efficiency compared with the conventional methods.

A fourth aspect of the present invention provides a method of producing a substance-encapsulating vesicle which can efficiently encapsulate, into an electrostatic interaction-type vesicle formed via self-assembly of polymers, a substance which is insoluble or poorly soluble to aqueous medium.

BRIEF DESCRIPTION OF THE DRAWINGS

FIGS. 1 (a) and (b) are drawings for explaining the method of the present invention.

FIG. 2 is a drawing for explaining the structure of a vacant vesicle.

FIGS. 3 (a) and (b) are drawings for explaining an embodiment of the membrane structure of a vacant vesicle.

FIGS. 4 (a) and (b) are drawings for explaining another embodiment of the membrane structure of a vacant vesicle.

FIG. 7 (a) is a graph showing the GPC measurement results of vacant vesicles, while (b) is a graph showing the GPC measurement results of the crosslinked vesicles encapsulating cytochrome c obtained in Example I-2 after purification.

FIG. 10(A) is a picture showing the results of colorimetric tests of the vesicles obtained in Example I-3 and Comparative Example I-3 based on the absorption color of AlPcS2a.

FIG. 11 is a transmission electron microscopic (TEM) image of the vesicles after the addition of 5 mM, 10 mM, or 20 mM NaCl.

FIG. 28 (a) is a TEM image of the untreated vesicles encapsulating MSN obtained in Example II-3A, while (b) is a TEM image of the aminated vesicles encapsulating MSN obtained in Example II-3A.

FIG. 29 (a) is a TEM image of the untreated vesicles encapsulating MSN used in Example II-3B, and (b) is a TEM image of the sulfonated vesicles encapsulating MSN obtained in Example II-3B.

FIGS. 33 (a) and (b) are graphs showing the cell intake profiles of the sulfonated vesicles encapsulating MSN adsorbing gemcitabine obtained in Example II-4B by A549 cells. Specifically, (a) shows the measurement results of the total amount of Cy3 fluorescence from all cells in the absence of trypan blue, while (b) shows the measurement results of the amount of Cy3 fluorescence from the living cells stained with trypan blue.

FIGS. 34 (a) and (b) are graphs showing the cytocidal effects of the sulfonated vesicles encapsulating MSN adsorbing gemcitabine obtained in Example II-4B on A549 cells. Specifically, (a) indicates the results after incubation of 48 hours, while (b) indicates the results after incubation of 72 hours.

FIGS. 35 (a) and (b) are graphs showing the cell intake profiles of the sulfonated vesicles encapsulating MSN adsorbing gemcitabine obtained in Example II-4B by C26 cells. (a) shows the measurement results of the total amount of Cy3 fluorescence from all cells in the absence of trypan blue, while (b) shows the measurement results of the amount of Cy3 fluorescence from the living cells stained with trypan blue.

FIGS. 36 (a) and (b) are graphs showing the cytocidal effects of the sulfonated vesicles encapsulating MSN adsorbing gemcitabine obtained in Example II-4B on C26 cells. (a) indicates the results after incubation of 48 hours, while (b) indicates the results after incubation of 72 hours.

FIGS. 37 (a) and (b) are graphs showing the therapeutic effect on tumor using the sulfonated vesicles encapsulating MSN adsorbing gemcitabine obtained in Example II-4B. (a) indicates the inhibitory effects on tumor growth, while (b) indicates the effects of reducing side effects (body weight loss).

MODE FOR CARRYING OUT THE INVENTION

Figure 5A:
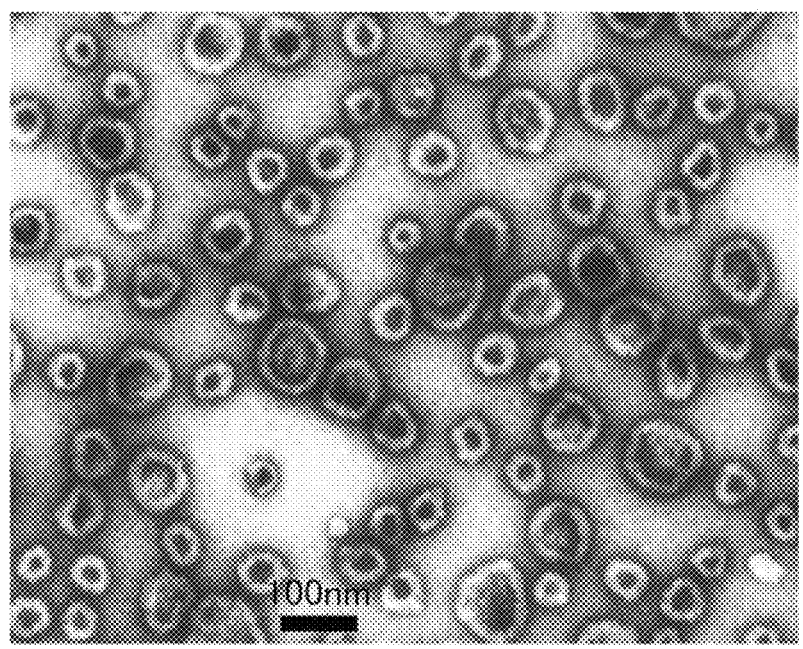
FIG. 5A is a transmission electron microscopic (TEM) image of the crosslinked vesicles encapsulating FITC-Dex40k obtained in Example I-1.

The invention will now be described in greater detail by concrete embodiments thereof. However, it is to be understood that the invention is not restricted in any way to the following embodiments, and various modifications thereof may be implemented.

[A] Definitions

The term "vesicle" as used herein refers to a basic structure having a membrane with a unilamellar structure, and a cavity (inner aqueous phase) surrounded by the membrane.

As used herein, the term "alkyl", as the name of a group or a portion thereof, refers to a monovalent aliphatic saturated hydrocarbon group. Unless otherwise specified, an alkyl group may be a chain or cyclic group, or it may consist of chain and cyclic portions bonded together. A chain alkyl group may be straight-chain or branched-chain. A cycloalkyl group may be monocyclic or polycyclic, and when it is polycyclic it may be a linked ring, a fused ring or a spiro ring.

As used herein, the term "alkoxy", as the name of a group or a portion thereof, refers to a group wherein the alkyl group is bonded at one bonding site of a divalent oxygen atom.

As used herein, the term "aryl", as the name of a group or a portion thereof, refers to a monovalent aromatic hydrocarbon group. Unless otherwise specified, the aryl may be monocyclic or polycyclic, and when it is polycyclic it may be a linked ring, a fused ring or a spiro ring.

As used herein, the number of carbons of a group will be denoted as "$C_{1-12}$ alkyl", for example. Here, "$C_{1-12}$" means that the number of carbon atoms of the alkyl is 1 to 12.

As used herein, "halogen atom" means fluorine, chlorine, bromine or iodine.

Also as used herein, the term "optionally substituted" in reference to a group means that the group may have one or more hydrogen atoms of the group substituted with one or more substituents (when more than one, they may be the same or different). The maximum number of substituents depends on the structure of the group and the number of substitutable hydrogen atoms, and can be easily determined by a person skilled in the art.

As used herein, the term "substituent", unless otherwise specified, refers to one selected from the group consisting of halogen atoms, aryl, hydroxyl, amino, carboxyl, cyano, formyl, dimethyl acetalated formyl, diethyl acetalated formyl, $C_{1-6}$ alkoxycarbonyl, $C_{2-7}$ acylamide, siloxy, tri ($C_{1-6}$ alkyl)siloxy group (where the $C_{1-6}$ alkyl groups may be the same or different) and silylamino.

As used herein, the term "monodisperse population" used in relation to various vesicles means a vesicle population with a narrow particle size distribution. The spread of the particle size distribution is preferably judged based on the polydispersity index (PDI), the monodisperse population having a polydispersity index of preferably no greater than 0.2, more preferably no greater than 0.15 and even more preferably no greater than 0.1.

As used herein, the term "polydispersity index" used in relation to various vesicles means a dimensionless index representing the spread of the particle size distribution, while the term "mean particle size" means the harmonic mean particle size (diameter) based on the scattered light intensity. The polydispersity index and mean particle size are both measured by dynamic light scattering. The dynamic light scattering method may be carried out according to JIS Z 8826:2005 (Particle size analysis—photon correlation spectroscopy). JIS Z 8826:2005 is a standard for dispersions with dilute particle concentrations, and appropriate modifications may be added to JIS Z 8826:2005 in order to allow measurement of polydispersity index and mean particle size of high-concentration samples as well. For example, back scattering detection may be employed instead of side scattering detection. By employing back scattering detection it is possible to eliminate or reduce the effect of multiple scattering, thereby allowing measurement of the polydispersity index and mean particle size even of high-concentration samples. The Zetasizer Nano-ZS by Malvern Co. may be mentioned as an example of a commercially available device for measurement of polydispersity index and mean particle size by dynamic light scattering. This device makes use of back scattering detection, allowing measurement of the polydispersity index and mean particle size in samples with a wide concentration range, from low concentration to high concentration.

[B] Substance-Encapsulating Vesicles and their Production Method

The substance-encapsulating vesicles and the production method therefor will be explained first, as the basis of the present invention. The features of the vesicles and their production method according to the invention will be explained again for [C] to [E], and all of the descriptions in this section also apply thereto unless otherwise noted in their description.

[B1: Method of Producing Substance-Encapsulating Vesicles

As mentioned above, the main production method for the substance-encapsulating vesicles may be (i) a method of mixing a substance to be encapsulated with a polymer that is to be a constituent element of a membrane, or with a previously formed polymer film, and simultaneously accomplishing formation of the vesicle by self-assembly and enclosure of the substance into the cavities (simultaneous mixing method), or (ii) a method of mixing previously formed vacant vesicles with the substance to be encapsulated, and introducing the substance to be encapsulated into the cavities of the vacant vesicles and incorporating and loading it therein (post-loading method).

According to the present invention, unless otherwise noted in the description for the production conditions for different vesicles, any desired method may be used including a simultaneous mixing method or a post-loading method. However, the post-loading method as a method developed by the present inventors (see PTL 3 (International Patent Publication No. WO2011/145745) for details) is preferred as it provides various advantages such as allowing the encapsulated substance to be efficiently introduced into vesicles in a convenient manner, and also allowing encapsulation of charged substances, that have been difficult to encapsulate by simultaneous mixing methods, essentially without damaging the structure of the vesicle before and after introduction.

The method of producing substance-encapsulating vesicles will hereunder be explained with the assumption of a post-loading method, but according to the invention the method of producing the substance-encapsulating vesicles is not limited to a post-loading method, and any other desired method, including a simultaneous mixing method, may be used so long as it does not interfere with the features of the substance-encapsulating vesicle, described hereunder. Furthermore, when a method other than a post-loading method is used to encapsulate a substance in vesicles, the specific conditions for the post-loading method described below may be applied as appropriate. For a simultaneous mixing method, for example, basically the same conditions may be used as for a post-loading method, except that the vacant vesicles are not prepared beforehand as in a post-loading method, and the polymer or other substance as the material for the vacant vesicles are mixed with the substance to be encapsulated.

(B1-1: General Description of Post-Loading Method)

A general description of a post-loading method will now be provided with reference to FIG. 1. FIG. 1 is a schematic diagram, and the invention is not limited to the illustration in FIG. 1.

As shown in FIG. 1(*a*), a vacant vesicle 1 is prepared having a prescribed structure with a cavity 1*b* surrounded by a membrane 1*a*, and it is mixed together with a substance to be encapsulated 9, in an aqueous medium. As a result, as shown in FIG. 1(*b*), the substance to be encapsulated 9 passes through the membrane 1*a* of the vacant vesicle 1 and is introduced into the cavity 1*b*, creating a substance-encapsulating vesicle 1' in which the substance to be encapsulated 9 is encapsulated in the cavity 1*b*.

A post-loading method will now be described in detail, although the details regarding the vacant vesicles and substance to be encapsulated will be described in a later section, focusing here only on the other relevant conditions and procedures.

(B1-2: Mixing of Vacant Vesicles and Substance to be Encapsulated)

The post-loading method includes a step of mixing the vacant vesicles and the substance to be encapsulated in an aqueous medium (the solution in an aqueous medium containing the vacant vesicles and the substance to be encapsulated, which are to be mixed, may hereunder also may be referred to as "mixing solution").

The method of mixing is not particularly restricted, but it is a method of applying external force to the aqueous medium. That is, this excludes methods of mixing by adding the vacant vesicles and the substance to be encapsulated to the aqueous medium and allowing them to stand for natural diffusion (hereunder also to be referred to as "stationary diffusion mixing"). Examples of mixing methods by application of external force to the aqueous medium include stirring, shaking and impacting.

Examples of methods by stirring include methods of stirring by revolution of the container holding the mixing solution using a vortex mixer or the like, and methods of directly stirring the solution with a stirring blade or the like.

Examples of methods by shaking include methods of shaking the container holding the mixing solution using a shaking apparatus or the like.

Examples of methods by impacting include methods of applying various forms of impact including vibration to the mixing solution, using ultrasonic irradiation or the like.

This mixing causes the substance to become encapsulated in the vesicle cavities, producing substance-encapsulating vesicles.

The reason for which substance-encapsulating vesicles are formed by mixing, though this is not absolutely established, is that shearing stress acts on the vacant vesicles upon application of external force to the aqueous medium (and it may therefore be restated that mixing wherein external force is applied to the aqueous medium is mixing under shearing stress). Presumably, this shearing stress disturbs the vacant vesicle structures, degrading them mostly into small uniform aggregates, which again undergo self-assembly such that the vesicles are uniformly regenerated, the substance to be encapsulated present in the aqueous medium becoming enclosed in the vesicles during regeneration of the vesicles (this mechanism is also inferred from the fact that degradation of the vesicles into small aggregates by mixing was confirmed in a reference experiment, described below). This is a phenomenon that does not readily occur with vesicles in their normal state, and therefore a post-loading method utilizing the phenomenon can be considered to be a very novel concept.

The mixing conditions are not restrictive, but in consideration of the mechanism described above, preferably the conditions are selected such that the vacant vesicle structure in the aqueous medium is sufficiently disturbed and the vesicle structure can be regenerated after disturbance. Normally, the mixing may be a sufficient degree so that force acts on the entire mixing solution, and preferably the mixing is to a degree such that the entire mixing solution is generally uniform.

The specific mixing conditions will differ depending on the mixing method, and in the case of stirring, for example, it is preferably carried out at a rotational speed of usually 500 rpm or greater and preferably 1000 rpm or greater, and usually no greater than 10,000 rpm and preferably no greater than 5000 rpm. If the rotational speed is too low, it may be difficult for homogeneous substance-encapsulating vesicles to form. If the rotational speed is too high, damage or destruction of the vesicles or substance to be encapsulated may occur.

Also, the stirring time with a vortex mixer will differ depending on the rotational speed, but will usually be 60 seconds or longer and preferably 120 seconds or longer, and is usually within 10 minutes and preferably within 5 minutes. If the stirring time is too short, it may be difficult for homogeneous substance-encapsulating vesicles to form. If the stirring time is too long, damage or destruction of the vesicles or substance to be encapsulated may occur.

The specific conditions when using other mixing methods (stirring with a stirring blade, shaking with a shaking apparatus, impacting with ultrasonic irradiation, or the like) may be appropriately adjusted conditions so that an equivalent amount of force acts on the mixing solution as when stirring with a vortex mixer is carried out with the rotational speed and stirring time specified above.

Also, likewise in consideration of the mechanism described above, mixing of the mixing solution is preferably followed by stationing of the mixing solution for a certain period of time to ensure time for the vesicles to uniformly regenerate. The stationing time is not restricted and may be, for example, 1 minute or longer and preferably 3 minutes or longer.

Encapsulation of the substance in the cavities of the vesicles can be confirmed by a method such as detection of changes in the diffusion coefficient by Fluorescence Correlation Spectroscopy (FCS), or separation by size exclusion chromatography, or direct observation with a transmission electron microscope. When the diffusion coefficient is measured by Fluorescence Correlation Spectroscopy, a fluorescent material may be used as the substance to be encapsulated and changes in the diffusion coefficient of the fluorescent material measured to confirm that the substance to be encapsulated is preferentially distributed within the vesicles (i.e. that substance-encapsulating vesicles have been obtained).

(B1-3: Other Conditions for Mixing)

Generally, a solution containing the vacant vesicles and the substance to be encapsulated in an aqueous medium (mixing solution) is prepared and supplied for the mixing described above.

The type of aqueous medium (aqueous solvent) is not restricted. It is preferably water, but a solvent comprising a mixture of other components with water (for example, physiological saline, aqueous buffers, water and water-soluble organic solvent mixtures, and the like) may also be used, so long as it does not have an undesirable effect on the vacant vesicles and does not interfere with introduction of the substance to be encapsulated into their interiors. One aqueous buffer that may be mentioned is 10 mM HEPES buffer. Water-soluble organic solvents include alcohols such as methanol and ethanol, ketones such as acetone, chlorine-based organic solvents such as chloroform, ether-based organic solvents such as dimethyl ether and esteric organic solvents such as ethyl acetate.

The procedure for preparing the solution to be mixed may be as desired, but since the vacant vesicles will usually be prepared in an aqueous medium as explained below, it is preferred to provide the substance to be encapsulated for addition and mixing with a prepared vacant vesicle-containing solution. The substance to be encapsulated may be added directly to the vacant vesicle-containing solution, or it may be added in a form such as a solution or suspension in an aqueous medium.

There are no particular restrictions on the respective concentrations of the vacant vesicles and the substance to be encapsulated in the solution to be mixed, and they may be determined in consideration of the conditions such as the vacant vesicle structure, the type of substance to be encapsulated, and the desired encapsulation ratio of the substance to be encapsulated with respect to the vacant vesicles.

However, from the viewpoint of increasing the encapsulation efficiency of the substance to be encapsulated in the vacant vesicles, the concentration of the vacant vesicles with respect to the aqueous medium will usually be 0.1 mg/mL or greater and preferably 1 mg/mL or greater, and usually no greater than 100 mg/mL and preferably no greater than 10 mg/mL. If the vacant vesicle concentration is too low, in particular, substance-encapsulating vesicles may not form. Because the sizes of the obtained substance-encapsulating vesicles may depend on the concentration of the vacant vesicles, the concentration of the vacant vesicles should be determined according to the desired substance-encapsulating vesicle size.

Also, the concentration of the substance to be encapsulated with respect to the aqueous medium will differ depending even on the nature of the substance to be encapsulated, but will usually be 0.1 mg/mL or greater and preferably 1 mg/mL or greater, and usually no greater than 100 mg/mL and preferably no greater than 50 mg/mL. If the concentration of the substance to be encapsulated is too low, in particular, substance-encapsulating vesicles may not form.

There is no particular restriction on the pH of the solution to be mixed, and it may be appropriately adjusted in consideration of the conditions including the vacant vesicle structure, the type of substance to be encapsulated, and the respective concentrations of the vacant vesicles and the substance to be encapsulated in the solution to be mixed, but it is preferably pH 5 or higher and more preferably pH 6.5 or higher, and preferably no higher than pH 9 and more preferably no higher than pH 7.5. The pH can be easily adjusted using a buffering solution as the solvent. Using a solution to be mixed with an adjusted pH is advantageous for maintaining the structure of the vacant vesicles and for efficiently encapsulating the substance to be encapsulated in the vacant vesicles.

The ionic strength of the solution to be mixed can be appropriately adjusted in a range that does not destroy the structure of the vacant vesicles or inhibit encapsulation of the substance to be encapsulated in the vacant vesicles, and it is preferably 0 mM or greater and more preferably 10 mM or greater, and preferably no greater than 200 mM and more preferably no greater than 50 mM.

The temperature during mixing of the solution to be mixed is not restricted, within a range that does not destroy the structure of the vacant vesicles or inhibit encapsulation of the substance to be encapsulated in the vacant vesicles, and it is preferably 10° C. or higher and more preferably 20° C. or higher, and preferably no higher than 80° C. and more preferably no higher than 50° C.

After mixing, the formed substance-encapsulating vesicles may be immediately supplied for the desired use, or a time may be allowed for stationing of the liquid mixture, to equilibrate the system. The time for stationing of the liquid mixture will differ depending on the conditions such as the efficiency with which the substance-encapsulating vesicles are formed, but it is preferably no greater than 50 hours and more preferably no greater than 30 hours. However, when a crosslinking agent is not used, the sizes of the formed substance-encapsulating vesicles will tend to increase with time, as explained below, and therefore it may be preferred for the stationing time to be no longer than the time required for uniform regeneration of the vesicles.

When a crosslinking agent is used, the crosslinking agent may be added to and mixed with the solution to be mixed which contains the formed substance-encapsulating vesicles. The crosslinking agent may be added directly, or an aqueous solution containing the crosslinking agent may be prepared and added. The conditions for preparation of an aqueous solution of the crosslinking agent, such as the aqueous solvent, pH, temperature and ionic strength, are the same conditions as described above for the solution to be mixed.

Procedures such as dialysis, dilution, concentration and stirring may also be carried out as appropriate.

[B2: Vacant Vesicles]

(B2-1: Vacant Vesicle Structure)

In a post-loading method, vesicles comprising a membrane formed from a first polymer which is a block copolymer which has an uncharged hydrophilic segment and a first charged segment, and a second polymer which has a second charged segment having a charge opposite to the charge of the first charged segment, and also comprising a cavity surrounded by the membrane, are used as vacant vesicles.

An example of a vacant vesicle structure will now be described with reference to FIGS. 2 to 4. FIGS. 2 to 4 are all schematic diagrams, and the invention is not limited to the illustrations therein.

FIG. 2 is a partial cutaway view of a vesicle 1. As shown in FIG. 2, the vesicle 1 has a membrane 1$a$, and a cavity 1$b$ surrounded by the membrane 1$a$.

FIG. 3($a$) is a partial cross-sectional magnified view of the membrane 1$a$ of the vesicle 1 according to one mode of the invention. The membrane 1$a$ shown in FIG. 3($a$) has a three-layered structure comprising an outer layer 1$a_o$, an intermediate layer $1a_m$ and an inner layer $1a_i$, and is formed mainly of a first polymer 2 and a second polymer 3.

FIG. 3(b) is a magnified view of the first polymer 2 and second polymer 3 shown in FIG. 3(a). As shown in FIG. 3(b), the first polymer 2 is a block copolymer having an uncharged hydrophilic segment 2a and a first charged segment 2b, while the second polymer 3 is a polymer comprising a second charged segment 3 having a charge opposite to the charge of the first charged segment 2b. Preferably, as shown in FIG. 3(a), the uncharged hydrophilic segment 2a forms the outer layer $1a_o$ of the membrane 1a, while the first charged segment 2b and the second charged segment 3 are electrostatically bonded to form the intermediate layer $1a_m$. Also preferably, primarily the uncharged hydrophilic segment 2a forms the inner layer $1a_i$ of the membrane 1a.

FIG. 4(a) is a partial cross-sectional magnified view of the membrane 1a of a vesicle 1 according to a different mode of the invention. The membrane 1a shown in FIG. 4(a) also has a three-layered structure comprising an outer layer $1a_o$, an intermediate layer $1a_m$ and an inner layer $1a_i$, and is formed mainly of a first polymer 2 and a second polymer 3'.

FIG. 4(b) is a magnified view of the first polymer 2 and second polymer 3' shown in FIG. 4(a). As shown in FIG. 4(b), the first polymer 2 is a block copolymer having an uncharged hydrophilic segment 2a and a first charged segment 2b, while the second polymer 3' is a polymer comprising an uncharged hydrophilic segment 3a and a second charged segment 3b having a charge opposite to the charge of the first charged segment 2b. Also preferably, as shown in FIG. 4(a), either or both the uncharged hydrophilic segments 2a, 3a form the outer layer $1a_o$ of the membrane 1a, while the first charged segment 2b and the second charged segment 3b are electrostatically bonded to form the intermediate layer $1a_m$. Also preferably, primarily either or both the uncharged hydrophilic segments 2a, 3a form the inner layer $1a_i$ of the membrane 1a.

While it is not our intention to be constrained by theory, it is believed that the mechanism by which the vesicle 1 is formed from the first polymer 2 and the second polymer 3, 3' is as follows. Specifically, when the first polymer 2 and the second polymer 3, 3' shown in FIG. 3(b) and FIG. 4(b) are placed in a system allowing interaction of electrical charges (for example, in an aqueous medium), they undergo self-assembly, and as shown in FIG. 3(a) and FIG. 4(a), the first charged segment 2b and the second charged segment 3, 3b which have mutually opposite electrical charges electrostatically bond together to form the intermediate layer $1a_m$, while the uncharged hydrophilic segments 2a, 3a are disposed on the outer side, forming the outer layer $1a_o$. Also, preferably, primarily the uncharged hydrophilic segments 2a, 3a are disposed on the inner side of the intermediate layer $1a_m$ as well, forming the inner layer $1a_i$. Presumably, a membrane 1a with the three-layered structure shown in FIG. 3(a) and FIG. 4(a) is thus formed, and as a result, a vesicle 1 as shown in FIG. 2 is formed.

The membrane 1a of the vesicle 1 may consist only of the first polymer 2 and the second polymer 3, 3', but it may also contain other components so long as the aforementioned structure is generally maintained. Such other components are not restricted, and examples include crosslinking agents, charged polymers and charged molecules. Crosslinking agents will be described in detail below.

Also, since the vesicle 1 is usually prepared in an aqueous medium as explained below, and the inner layer $1a_i$ of the membrane 1a is composed primarily of the uncharged hydrophilic segments 2a, 3a, the aqueous medium will usually be present in the cavity 1b of the vesicle 1 (and therefore the cavity 1b may be referred to as "inner aqueous phase" throughout the present specification). However, other substances may also be present in the cavity 1b.

The shape of the vesicle 1 is not restricted but will usually be spherical or approximately spherical.

The diameter of the vesicle 1 will differ depending on the type and weight ratio of the first polymer 2 and the second polymer 3, 3', the presence or absence of a crosslinking agent and the surrounding environment of the vesicle 1 (type of aqueous medium), but it is preferably 10 nm or greater and more preferably 50 nm or greater, and preferably no greater than 1000 nm, more preferably no greater than 400 nm and even more preferably no greater than 200 nm.

The thickness of the membrane 1a of the vesicle 1 will also differ depending on the type and weight ratio of the first polymer 2 and the second polymer 3, 3', the presence or absence of a crosslinking agent and the surrounding environment of the vesicle 1 (type of aqueous medium), but it is preferably 5 nm or greater and more preferably 10 nm or greater, and preferably no greater than 30 nm and more preferably no greater than 15 nm.

(B2-2: First and Second Polymers)

The vacant vesicles to be used in a post-loading method have a membrane composed of a first polymer and a second polymer.

The first polymer is a block copolymer having an uncharged hydrophilic segment and a first charged segment. The first polymer may be of a single type alone, or any desired combination and proportion of two or more types in combination.

The second polymer is a polymer with a second charged segment having a charge opposite to the charge of the first charged segment. It may be a polymer composed only of the second charged segment, or it may be a block copolymer having an uncharged hydrophilic segment in addition to the second charged segment. The second polymer may be of a single type or any desired combination and proportion of two or more types in combination. In the case of two or more types, a second polymer composed only of the second charged segment and a second polymer having an uncharged hydrophilic segment in addition to the second charged segment may be used in combination.

The first polymer and second polymer may also have yet another segment in addition to the respective segments mentioned above.

(B2-2a: Uncharged Hydrophilic Segment)

The first polymer has an uncharged hydrophilic segment. The second polymer may also have an uncharged hydrophilic segment.

The uncharged hydrophilic segment is a polymer segment that is uncharged and has a hydrophilic property. Here, "uncharged" means that the segment is neutral overall. As examples there may be mentioned segments without positive or negative charges. Also, even if the segment has a positive or negative charge in the molecule, it may still qualify as being "uncharged" so long as the local effective charge density is not high and the segment has enough of an overall neutral charge so as to not interfere with formation of vesicles by self-assembly. The term "hydrophilic" means exhibiting solubility in aqueous media.

The type of uncharged hydrophilic segment is not restricted. It may be a segment consisting of a single repeating unit, or it may be a segment containing two or more different repeating units in any desired combination and proportion. Specific examples of uncharged hydrophilic segments include polyalkylene glycols, poly(2-oxazoline), polysaccharides, polyvinyl alcohol, polyvinylpyrrolidone, polyacrylamide, polymethacrylamide, polyacrylic acid ester, polymethacrylic acid ester, poly(2-methacryloyloxyethyl-phosphorylcholine), and peptides or proteins with isoelectric points of around 7, as well as their derivatives. Of these, polyalkylene glycols and poly(2-oxazoline) are preferred, with polyalkylene glycols being especially preferred. Polyalkylene glycols include polyethylene glycol, polypropylene glycol and the like, with polyethylene glycol being preferred.

The molecular weight of the uncharged hydrophilic segment is not restricted, but preferably it has a molecular weight in a prescribed range, from the viewpoint of self-assembly of the first polymer and second polymer, and of efficiently producing uniform vesicles. The specific molecular weight range will differ depending on the type of uncharged hydrophilic segment, the combination of charged segments and other factors, but when the uncharged hydrophilic segment is polyethylene glycol, the molecular weight (Mw) is preferably in the range of 500 or greater and more preferably 1000 or greater, and preferably no greater than 15,000 and more preferably no greater than 5000. The number of repeating units of the uncharged hydrophilic segment are not restricted, and in most cases it will be determined by the type of repeating unit, so that the molecular weight of the uncharged hydrophilic segment satisfies the aforementioned molecular weight range.

By using an uncharged hydrophilic segment satisfying these conditions, it is possible to prevent aggregation and precipitation of the first polymer and second polymer in the aqueous solution and stabilize them, in order to efficiently construct vesicles.

(B2-2b: Charged Segment)

The first charged segment of the first polymer and the second charged segment of the second polymer are charged segments that have mutually opposite charges. That is, if the first charged segment is a cationic segment, the second charged segment is an anionic segment, and if the first charged segment is an anionic segment, the second charged segment is a cationic segment.

(B2-2b-1: Cationic Segment)

A cationic segment is a polymer segment having a cationic group and exhibiting cationicity. However, a cationic segment may have some anionic groups, in a range that does not interfere with formation of the vesicles by self-assembly of the first polymer and second polymer.

The type of cationic segment is not restricted. It may be a segment consisting of a single repeating unit, or it may be a segment containing two or more different repeating units in any desired combination and proportion. The cationic segment is preferably a polyamine or the like, and most preferably a polyamino acid having an amino group on a side chain, or a derivative of the same. Polyamino acids having amino groups on side chains, or their derivatives, include polyaspartamide, polyglutamide, polylysine, polyarginine and polyhistidine, and their derivatives, with polyaspartamide derivatives and polyglutamide derivatives being especially preferred.

The molecular weight of the cationic segment is not restricted, but preferably it has a molecular weight in a prescribed range, from the viewpoint of self-assembly of the first polymer and second polymer, and of efficiently producing uniform vesicles. The number of repeating units of the cationic segment are not restricted, and in most cases it will be determined by the type of repeating unit, so that the molecular weight of the cationic segment satisfies the prescribed range. Specifically, when a polyaspartic acid derivative is used as the cationic segment, the number of repeating units is in the range of preferably 10 or greater and more preferably 50 or greater, and preferably no greater than 200 and more preferably no greater than 100.

By using a cationic segment satisfying these conditions, it is possible to prevent aggregation and precipitation of the first polymer and second polymer in the aqueous solution and stabilize them, in order to efficiently construct vesicles.

(B2-2b-2: Anionic Segment)

An anionic segment is a polymer segment having an anionic group and exhibiting anionicity. However, an anionic segment may have some cationic groups, in a range that does not interfere with formation of the vesicles by self-assembly of the first polymer and second polymer.

The type of anionic segment is not restricted. It may be a segment consisting of a single repeating unit, or it may be a segment containing two or more different repeating units in any desired combination and proportion. Preferred as anionic segments are polycarboxylic acids, polysulfonic acids, polyphosphoric acids (nucleic acids) and the like, with polyamino acids having carboxyl groups on a side chain, or their derivatives, and nucleic acids being especially preferred.

Polyamino acids having carboxyl groups on side chains, and their derivatives, include polyaspartic acid, polyglutamic acid, and polycarboxylic acids that are polycations and obtained by reacting a suitable amount of aconitic anhydride or citraconic anhydride with the amino groups of a polyamino acid or its derivative having amino groups on side chains, as well as their derivatives, with polyaspartic acid and polyglutamic acid being especially preferred.

Nucleic acids include single-stranded or double-stranded DNA or RNA. Nucleic acids may also be functional nucleic acids, depending on the purpose of use of the vesicles. Functional nucleic acids include siRNA, miRNA (microRNA), antisense RNA, antisense DNA, ribozymes, DNA enzymes, and the like. These may be selected according to the purpose of use of the vesicles. For example, when the vesicles are to be used as a DDS for RNAi, siRNA may be used as the nucleic acid. The nucleic acid may also be modified. Examples of modified nucleic acids include nucleic acids having hydrophobic functional groups such as cholesterol or vitamin E bonded thereto, for the purpose of vesicle stabilization or the like.

The molecular weight of the anionic segment is not restricted, but preferably it has a molecular weight in a prescribed range, from the viewpoint of self-assembly of the first polymer and second polymer, and of efficiently producing uniform vesicles. The number of repeating units of the anionic segment are not restricted, and in most cases it will be determined by the type of repeating unit, so that the molecular weight of the anionic segment satisfies the prescribed range. Specifically, when a polycarboxylic acid, polysulfonic acid or nucleic acid is used as the anionic segment, the number of repeating units is in the range of preferably 10 or greater and more preferably 50 or greater, and preferably no greater than 200 and more preferably no greater than 100.

By using an anionic segment satisfying these conditions, it is possible to prevent aggregation and precipitation of the first polymer and second polymer in the aqueous solution and stabilize them, in order to efficiently construct vesicles.

(B2-2c: Combination of Uncharged Hydrophilic Segment and Charged Segment)

There are no restrictions on the combination of the uncharged hydrophilic segment and the first charged segment in the first polymer, or on the combination of the uncharged hydrophilic segment and the second charged segment in the second polymer, when it has an uncharged hydrophilic segment in addition to the second charged segment, and a combination of any uncharged hydrophilic segment and any charged segment is possible (in the description which follows, the first charged segment and the second charged segment will sometimes be referred to collectively as "charged segments").

The number of uncharged hydrophilic segments and charged segments may also be as desired, being one of each or two or more of each, and in the case of two or more of each, they may be the same or different.

There is no restriction on the form of bonding of the uncharged hydrophilic segment and the charged segment, and it may be direct bonding or bonding through a linking group.

Examples of linking groups include hydrocarbon groups with a valency corresponding to the total number of uncharged hydrophilic segments and charged segments. A hydrocarbon group used as a linking group may be aliphatic, aromatic or a linkage of the two, and when aliphatic it may be saturated or unsaturated, or straight-chain, branched or cyclic. The molecular weight of the hydrocarbon group used as a linking group is not restricted but will usually be no greater than 5000 and is preferably no greater than 1000. Examples of hydrocarbon groups to be used as linking groups include gallic acid derivatives, 3,5-dihydroxybenzoic acid derivatives, glycerin derivatives, cyclohexane derivatives, L-lysine, and the like, with 3,5-dihydroxybenzoic acid derivatives being preferred.

Other examples of linking groups include disulfide groups. A disulfide group is used to link one uncharged hydrophilic segment and one charged segment. By linking the uncharged hydrophilic segment and charged segment through a disulfide group, it is possible to split the disulfide group by the environment in which the vesicles reside or by external action, thereby altering the form or properties of the vesicles. If this is utilized, for example, to encapsulate a drug in vesicles and the obtained substance-encapsulating vesicles are used in a DDS for drug delivery, then splitting the disulfide groups in vivo can potentially promote release of the substance encapsulated in the vesicles.

Furthermore, while the proportion of the first charged segment and second charged segment (the proportion of the cationic segment and anionic segment) and the proportion of the uncharged hydrophilic segment and charged segment may also be as desired, they are preferably selected based on the following criteria, from the viewpoint of promoting self-assembly of the first polymer and second polymer and efficiently producing a uniform vesicle.

First, the proportion between the cationic segment and the anionic segment is preferably adjusted so that the C/A ratio defined by the following equation (i) is usually 0.3, preferably 0.5 or higher and more preferably 0.6 or higher, and usually lower than 3.0, preferably 2.0 or lower, and more preferably 1.7 or lower.

[Equation 1]

C/A ratio (molar ratio)=[number of moles of cationic groups in first and second polymers]/[number of moles of anionic groups in first and second polymers]   Formula (i)

In this equation, the moles of cationic groups and anionic groups in the first and second polymers are values that depend on the structures of the cationic segment and the anionic segment, and they can be determined by common potentiometric (acid/base) titration.

Also, the proportion of the uncharged hydrophilic segment and the charged segment in the first and second polymers is preferably determined in consideration of a proportion of the cationic segment and the anionic segment that satisfies the above range of the C/A ratio. Specifically, the molecular weight ratio X of the uncharged hydrophilic segment defined by the following equation (ii) is preferably kept in the range of usually 0.01 or higher and preferably 0.05 or higher, and usually 0.35 or lower and preferably 0.1 or lower.

In a case where one each of the cationic segment (assumed to have one positive electric charge per monomer) and the anionic segment (assumed to have one negative electric charge per monomer) is used, and an uncharged hydrophilic segment is introduced into at least one of them (i.e., a case where the first polymer is a block copolymer having a cationic or an anionic segment and an uncharged hydrophilic segment, and the second polymer is a homopolymer of an anionic or a cationic segment or a block copolymer having an uncharged hydrophilic segment in addition to it), its X is defined by the following equation:

[Equation 2]

Formula (ii)

$M_{NA}$ represents the molecular weight of the uncharged hydrophilic segment linked to the anionic segment,
$M_{NC}$ represents the molecular weight of the uncharged hydrophilic segment linked to the cationic segment,
$M_C$ represents the molecular weight of the cationic segment,
$M_A$ represents the molecular weight of the anionic segment,
$P_C$ represents the polymerization degree of the cationic segment,
$P_A$ represents the polymerization degree of the anionic segment.

(B2-2d: Specific Examples of First and Second Polymers)

The following [Example 1] and [Example 2] may be mentioned as specific examples of the first and second polymers.

Example 1

The following (A1) is used as the first polymer and the following (B1) is used as the second polymer.
(A1) A block copolymer having an uncharged hydrophilic segment and an anionic segment.
(B1) A block copolymer of the following (i) and/or a polymer of the following (ii):
  (i) A block copolymer having an uncharged hydrophilic segment and a cationic segment.
  (ii) A polymer having a cationic segment (but having no uncharged hydrophilic segment).

Example 2

The following (A2) is used as the first polymer and the following (B2) is used as the second polymer.
(A2) A block copolymer having an uncharged hydrophilic segment and a cationic segment.
(B2) A block copolymer of the following (iii) and/or a polymer of the following (iv):
  (iii) A block copolymer having an uncharged hydrophilic segment and an anionic segment.
  (iv) A polymer having an anionic segment (but having no uncharged hydrophilic segment).

For the purpose of the present invention, a polymer having no uncharged hydrophilic segment, as in the polymers of (B1) (ii) and (B2) (iv) above, may be referred to as a "homopolymer" for convenience.

While there is no limitation on the cationic segment in each of the polymers of (B1) (i) and (ii) and (A2) above, preferred examples that may be mentioned include those derived from polypeptides having a cationic group on a side chain.

Similarly, while there is no limitation on the anionic segment in each of the polymers of (A1) and (B2) (iii) and (iv) above, preferred examples that may be mentioned include those derived from polypeptides or nucleic acids having an anionic group on a side chain.

More specifically, preferred examples for each block copolymer of (A1) and (B2) (iii) above include those represented by the following general formula (I) and/or (II).

[Chemical Formula 1]

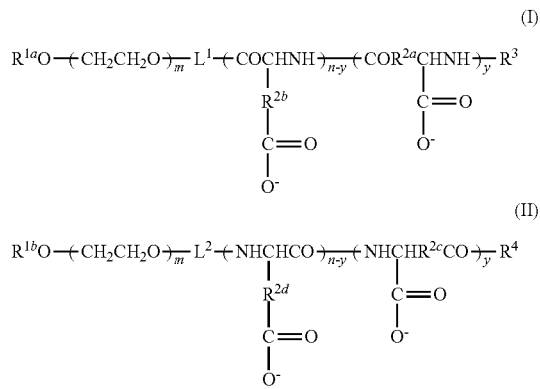

In the structural formulas of general formulas (I) and (II), segments having a number of repeating units (degree of polymerization) of "m" are uncharged hydrophilic segments derived from PEG (hereinafter referred to as "PEG segments"), and segments that are a combination of sections having a number of repeating units of "n-y" and sections having a number of repeating units of "y" are anionic segments derived from polyanions (hereinafter referred to as "polyanionic segments").

In general formulas (I) and (II), $R^{1a}$ and $R^{1b}$ each independently represent a hydrogen atom or an unsubstituted or substituted straight-chain or branched $C_{1-12}$ alkyl group. Examples of straight-chain or branched $C_{1-12}$ groups include methyl, ethyl, n-propyl, iso-propyl, n-butyl, sec-butyl, tert-butyl, n-pentyl, n-hexyl, decyl, undecyl and the like. When substituents are present, the substituents may be acetalized formyl, cyano, formyl, carboxyl, amino, $C_{1-6}$ alkoxycarbonyl, $C_{2-7}$ acylamido, identical or different tri-$C_{1-6}$ alkylsiloxy, siloxy or silylamino groups. As used herein, acetalization means the formation of an acetal portion by reaction of the carbonyl group of formyl with, for example, two C1-6 alkanol molecules or an optionally branched C2-6 alkylenediol, and thus it is also a method for protecting the carbonyl group. For example, when the substituent is an acetalized formyl group, it can be hydrolyzed under acidic mild conditions for conversion to another substituent which may be a formyl group (—CHO) (or an aldehyde group).

In general formulas (I) and (II), $L^4$ and $L^2$ represent linking groups. Specifically, $L^4$ is preferably —$(CH_2)_b$—NH— (where b is an integer of 1 to 5), and $L^2$ is preferably —$(CH_2)_c$—CO— (where c is an integer of 1 to 5).

In general formulas (I) and (II), $R^{2a}$, $R^{2b}$, $R^{2c}$ and $R^{2d}$ each independently represent a methylene or ethylene group. When both $R^{2a}$ and $R^{2b}$ are methylene groups, it corresponds to a poly(aspartic acid derivative) and when they are ethylene groups, it corresponds to a poly(glutamic acid derivative), or when both $R^{2c}$ and $R^{2d}$ are methylene groups, it corresponds to a poly(aspartic acid derivative) and when they are ethylene groups it corresponds to a poly(glutamic acid derivative). In these general formulas, when $R^{2a}$ and $R^{2b}$ ($R^{2b}$ and $R^{2a}$) represent both a methylene group and an ethylene group, and when $R^{2c}$ and $R^{2d}$ ($R^{2d}$ and $R^{2c}$) represent both a methylene group and an ethylene group, the repeating aspartic acid derivative and the glutamic acid derivative units may be present either as blocks or in a random fashion.

In general formulas (I) and (II), $R^3$ represents a hydrogen atom, a protecting group, a hydrophobic group or a polymerizable group. Specifically, $R^3$ is preferably an acetyl, acryloyl or methacryloyl group.

In general formulas (I) and (II), $R^4$ represents hydroxyl, oxybenzyl, the group —NH—$(CH_2)_a$—X or an initiator residue. Herein, a represents an integer of 1 to 5, and X is preferably the residue of an amine compound comprising one or more from among primary, secondary and tertiary amines, or quaternary ammonium salts, or the residue of a compound other than an amine. Furthermore, in some cases, $R^4$ is preferably —NH—$R^9$ (where $R^9$ represents an unsubstituted or substituted straight-chain or branched $C_{1-20}$ alkyl group).

In the general formulas (I) and (II), m is an integer of 5 to 2,000, preferably an integer of 5 to 270, and more preferably an integer of 10 to 100. Also, n represents an integer of 2 to 5,000, y represents an integer of 0 to 5,000, and preferably n and y represent integers of 5 to 300 and more preferably integers of 10 to 100. This is with the proviso that y is not greater than n.

While each of the repeating units in general formulas (I) and (II) is represented here in a specified order for convenience of description, each of the repeating units may be present in a random order. Specifically, it is preferred for the repeating units in only the polyanionic segment to be present in a random order as described above.

While the molecular weights (Mw) of the block copolymers represented by general formulas (I) and (II) are not restricted, they are preferably 3,000 to 30,000, and more preferably 5,000 to 20,000. For individual segments, the molecular weight (Mw) of the PEG segment is preferably 500 to 15,000 and more preferably 1,000 to 5,000, and the molecular weight (Mw) of the polyanionic segment is preferably 500 to 50,000 and more preferably 1,000 to 20,000.

The method for producing the block copolymers represented by general formulas (I) and (II) is not restricted, and examples include a method in which a segment that contains $R^{1a}O$— or $R^{1b}O$— and a PEG chain block portion (PEG segment) is synthesized in advance, prescribed monomers are polymerized in order at one end (the end opposite to $R^{1a}O$— or $R^{1b}O$—) of the PEG segment, and then a side chain is substituted or converted as necessary so as to include an anionic group, or a method in which the aforementioned PEG segment and a block portion having a side chain containing an anionic group are synthesized in advance, and are then linked together. The method and conditions for the different reactions in the above production methods may be selected or designed as appropriate in consideration of conventional methods. The PEG segment described above may be prepared using a method for producing the PEG segment portion of a block copolymer as described in, for example, WO96/32434, WO96/33233 or WO97/06202.

An example of a more specific method for producing block copolymers represented by general formulas (I) and (II) that is preferred, is a method in which a PEG segment derivative having an amino group at the terminus is used, and the N-carboxylic anhydride (NCA) of a protective amino acid such as β-benzyl-L-aspartate (BLA) or Nε-Z-L-lysine is polymerized at the amino terminal to synthesize a block copolymer, after which the side chain of each segment is substituted or converted so as to become a side chain with the aforementioned anionic group.

According to the invention, preferred specific examples of block copolymers represented by general formulas (I) and (II) include anionic block copolymers (hereinafter also referred to as "PEG-P(Asp)") of the following formula, comprising polyethylene glycol (hereinafter also referred to as "PEG") as an uncharged hydrophilic segment, and polyaspartic acid (hereinafter also referred to as "P(Asp)") as an anionic segment (In the following formulas, Na+ may be indicated as an example of a counter cation, with the understanding that the counter cation is not limited thereto).

[Chemical Formula 2]

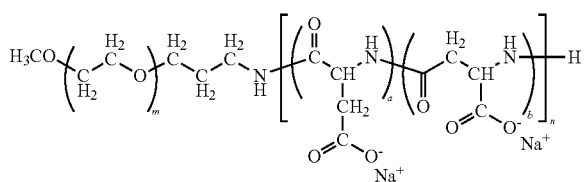

wherein, m represents an integer indicating the degree of polymerization of PEG, n represents an integer indicating the degree of polymerization of P(Asp), and both a and b are greater than 0 and less than 1, with the proviso that a+b=1.

As PEG-P(Asp), there is particularly preferred one wherein the molecular weight (Mw) of the PEG segment is 2,000 and the number of P(Asp) units representing a polyanionic segment (n in the above formula) is 70 or 75.

Preferred examples for each block copolymer in (A2) and (B1) (i) above include those represented by the following general formula (III) and/or (IV).

[Chemical Formula 3]

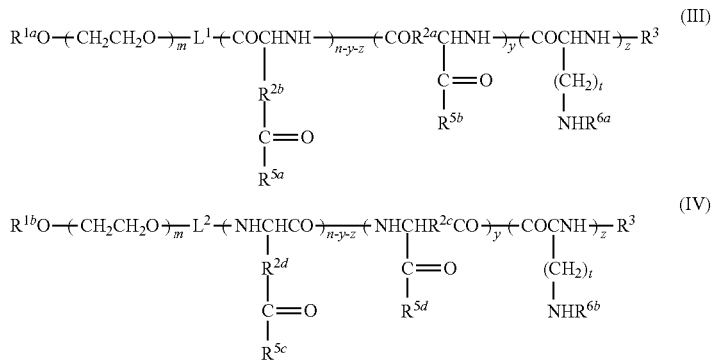

In the structural formulas of general formulas (III) and (IV), the segments having a number of repeating units (degree of polymerization) of "m" are uncharged hydrophilic segments derived from PEG ("PEG segments"), while the segments that are combinations of portions with "n-y-z", portions with "y" and portions with "z" number of repeating units are cationic segments derived from polycations (hereinafter referred to as "polycationic segments").

In general formulas (III and (IV), $R^{1a}$ and $R^{1b}$ each independently represent a hydrogen atom or an unsubstituted or substituted straight-chain or branched $C_{1-12}$ alkyl group. Examples of straight-chain or branched $C_{1-12}$ groups include methyl, ethyl, n-propyl, iso-propyl, n-butyl, sec-butyl, tert-butyl, n-pentyl, n-hexyl, decyl, undecyl and the like. When substituents are present, the substituents may be acetalized formyl, cyano, formyl, carboxyl, amino, $C_{1-6}$ alkoxycarbonyl, $C_{2-7}$ acylamido, identical or different tri-$C_{1-6}$ alkylsiloxy, siloxy or silylamino groups. As used herein, acetalization means the formation of an acetal portion by reaction of the carbonyl group of formyl with, for example, two C1 to 6 alkanol molecules or an optionally branched C2 to 6 alkylenediol, and thus it is also a method for protecting the carbonyl group. For example, when the substituent is an acetalized formyl group, it can be hydrolyzed under acidic mild conditions for conversion to another substituent, i.e. a formyl group (—CHO: or an aldehyde group).

In general formulas (III) and (IV), $L^1$ and $L^2$ represent linking groups. Specifically, $L^1$ is preferably —$(CH_2)_b$—NH— (where b is an integer of 1 to 5), and $L^2$ is preferably —$(CH_2)_c$—CO— (where c is an integer of 1 to 5).

In general formulas (III) and (IV), $R^{2a}$, $R^{2b}$, $R^{2c}$ and $R^{2d}$ each independently represent a methylene or ethylene group. When both $R^{2a}$ and $R^{2b}$ are methylene groups, it corresponds to a poly(aspartic acid derivative) and when they are ethylene groups, it corresponds to a poly(glutamic acid derivative), or when both $R^{2c}$ and $R^{2d}$ are methylene groups, it corresponds to a poly(aspartic acid derivative) and when they are ethylene groups it corresponds to a poly(glutamic acid derivative). In these general formulas, when $R^{2a}$ and $R^{2b}$ ($R^{2b}$ and $R^{2a}$) represent both a methylene group and an ethylene group, and when $R^{2c}$ and $R^{2d}$ ($R^{2d}$ and $R^{2c}$) represent both a methylene group and an ethylene group, the repeating aspartic acid derivative and the glutamic acid derivative units may be present either as blocks or in a random fashion.

In general formulas (III) and (IV), $R^3$ represents a hydrogen atom, a protecting group, a hydrophobic group or a polymerizable group. Specifically, $R^3$ is preferably an acetyl, acryloyl or methacryloyl group.

In general formulas (III) and (IV), $R^4$ represents hydroxyl, oxybenzyl, the group —NH—$(CH_2)_a$—X or an initiator residue. Here, a represents an integer of 1 to 5, and X is preferably the residue of an amine compound containing one or more from among primary, secondary, and tertiary amines, quaternary ammonium salts and guanidino groups, or the residue of a compound other than an amine. Furthermore, in some cases, $R^4$ is preferably —NH—$R^9$ (where $R^9$ represents an unsubstituted or substituted straight-chain or branched $C_{1-20}$ alkyl group).

In general formulas (III) and (IV), $R^{5a}$, $R^{5b}$, $R^{5c}$ and $R^{5d}$ each independently represent hydroxyl, oxybenzyl, or the group —NH—$(CH_2)_a$—X. Here, a represents an integer of 1 to 5, and X is preferably the residue of an amine compound containing one or more from among primary, secondary, and tertiary amines, quaternary ammonium salts and guanidino groups, or the residue of a compound other than an amine.

Preferably, two or more of the total number of $R^{5a}$ and $R^{5b}$ and the total number of $R^{5c}$ and $R^{5d}$ groups are —NH—$(CH_2)_a$—X groups (where X is $(NH(CH_2)_2)_e$—$NH_2$ (with the proviso that e is an integer of 0 to 5)), more preferably 50% or more of the total number are said group, and even more preferably 85% or more of the total number are said group.

Also, preferably all or some of $R^{5a}$, $R^{5b}$, $R^{5c}$ and $R^{5d}$ are —NH—$(CH_2)_a$—X groups (where a is 2 and X is (NH$(CH_2)_2)_e$—$NH_2$ (with the proviso that e is 1)).

Furthermore, In the group —NH—$(CH_2)_a$—X as an example of $R^4$ and $R^{5a}$, $R^{5b}$, $R^{5c}$ and $R^{5d}$, preferably X is selected from among groups represented by the following formulas.

[Chemical Formula 4]

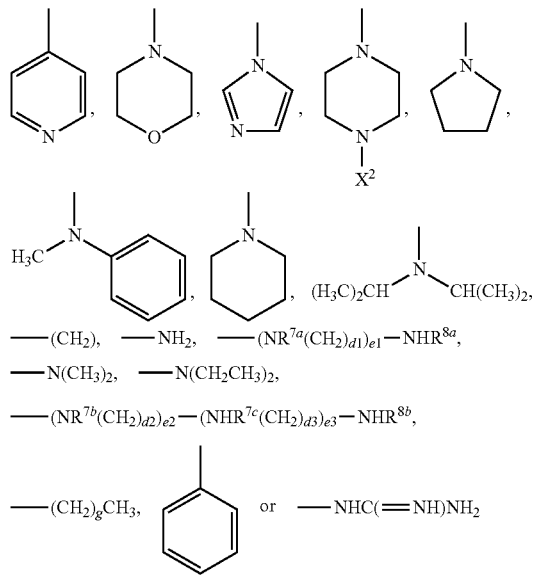

In each of the above formulas, $X^2$ represents a hydrogen atom, a $C_{1-6}$ alkyl group or an amino $C_{1-6}$ alkyl group, $R^{7a}$, $R^{7b}$ and $R^{7c}$, each independently represent a hydrogen atom or methyl group, d1, d2 and d3 each independently represent an integer of 1 to 5, e1, e2 and e3 each independently represent an integer of 1 to 5, f represents an integer of 0 to 15, g represents an integer of 0 to 15, and $R^{8a}$ and $R^{8b}$ each independently represent a hydrogen atom or a protecting group. Here, the protecting group is preferably selected from the group consisting of a Z group, Boc group, acetyl group and trifluoroacetyl group, that are commonly used as protecting groups for amino groups.

In general formulas (III) and (IV), $R^{6a}$ and $R^{6b}$ each independently represent a hydrogen atom, —C(=NH)$NH_2$ or a protecting group, wherein the protecting group is preferably selected from the group consisting of a Z group, Boc group, acetyl group and trifluoroacetyl group, that are commonly used as protecting groups for amino groups. Also in general formulas (III) and (IV), t preferably represents an integer of 2 to 6, and more preferably 3 or 4.

In general formulas (III) and (IV), m represents an integer of 5 to 2,000, preferably an integer of 5 to 270, and more preferably an integer of 10 to 100. The letter n represents an integer of 2 to 5,000, y represents an integer of 0 to 5,000, and z represents an integer of 0 to 5,000. The letter n preferably represents an integer of 5 to 300, and more preferably represents 0 or an integer of 10 to 100. The letters y and z each preferably represent 0 or an integer of 5 to 300, and more preferably 0 or an integer of 10 to 100. This is with the proviso that the sum of y and z (y+z) is not greater than n.

While each of the repeating units in general formulas (III) and (IV) is represented here in a specified order for convenience of description, each of the repeating units may be present in a random order. Specifically, it is preferred for the repeating units in only the polycationic segment to be present in a random order as described above.

While the molecular weights (Mw) of the block copolymers represented by general formulas (III) and (IV) are not restricted, they are preferably 23,000 to 45,000, and more preferably 28,000 to 34,000. For individual segments, the molecular weight (Mw) of the PEG segment is preferably 500 to 15,000 and more preferably 1,000 to 5,000, and the molecular weight (Mw) of the polycationic segment is preferably 500 to 50,000 and more preferably 1,000 to 30,000.

The method for producing the block copolymers represented by general formulas (III) and (IV) is not restricted, and examples include a method in which a segment that contains $R^{1a}O^-$ or $R^{1b}O^-$ and a PEG chain block portion (PEG segment) is synthesized in advance, prescribed monomers are polymerized in order at one end (the end opposite to $R^{1a}O^-$ or $R^{1b}O^-$) of the PEG segment, and then a side chain is substituted or converted as necessary so as to include a cationic group, or a method in which the aforementioned PEG segment and a block portion having a side chain containing a cationic group are synthesized in advance, and are then linked together. The method and conditions for the different reactions in the above production methods may be selected or designed as appropriate in consideration of conventional methods. The PEG segment described above may be prepared using a method for producing the PEG segment portion of a block copolymer as described in, for example, WO96/32434, WO96/33233, WO97/06202, and the like.

An example of a more specific method for producing block copolymers represented by general formulas (III) and (IV) that is preferred, is a method in which a PEG segment derivative having an amino group at the terminus is used, and the N-carboxylic anhydride (NCA) of a protective amino acid such as β-benzyl-L-aspartate (BLA) or Nε-Z-L-lysine is polymerized at the amino terminal to synthesize a block copolymer, after which the side chain of each segment is substituted or converted with diethylenetriamine (DET) or the like, so as to become a side chain with the aforementioned cationic group.

Preferred specific examples of block copolymers represented by general formulas (III) and (IV) include cationic block copolymers of the following formula, comprising polyethylene glycol (hereinafter also referred to as "PEG") as an uncharged hydrophilic segment, and a poly(diaminopentane structure-containing asparagine derivative) (hereunder also referred to as "P(Asp-AP)") as a cationic segment (hereinafter also referred to as "PEG-P(Asp-AP)"). In the following formulas, Cl⁻ may be indicated as an example of a counter anion, with the understanding that the counter anion is not limited thereto.

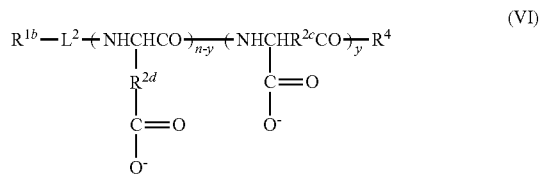

(VI)

According to the invention, preferred specific examples of polymers represented by general formulas (V) and (VI) include anionic homopolymers of the following formula, comprising polyaspartic acid (P(Asp)) as an anionic segment (hereinafter referred to as "Homo-P(Asp)").

[Chemical Formula 5]

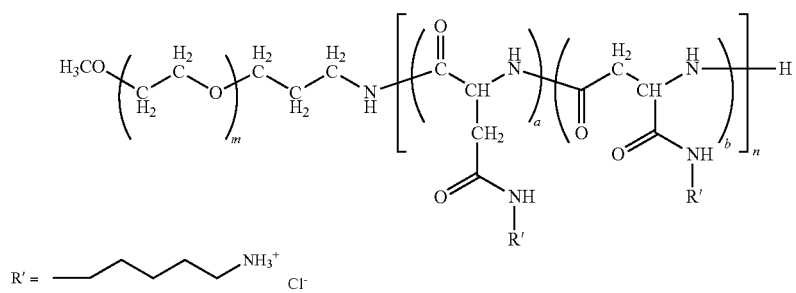

wherein, m represents an integer indicating the degree of polymerization of PEG, n represents an integer that indicates the degree of polymerization of P(Asp-AP), and both a and b are greater than 0 and less than 1, with the proviso that a+b=1.

As PEG-P(Asp-AP), there is particularly preferred one wherein the molecular weight (Mw) of the PEG segment is 2,000 and the number of P(Asp-AP) units representing a polycationic segment (n in the above formula) is 70 or 75.

Preferred examples for the polymer in (B2) (iv) above include those represented by the following general formula (V) and/or (VI). For the explanation of general formulas (V) and (VI), the explanation of general formulas (I) and (II) (excluding the explanation on the PEG segment) may be similarly applied as appropriate.

[Chemical Formula 6]

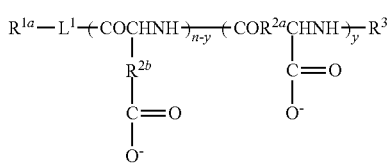

(V)

[Chemical Formula 7]

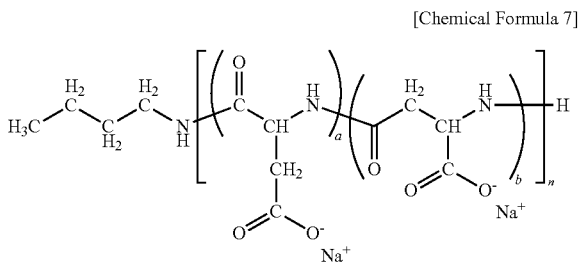

wherein, n represents an integer indicating the degree of polymerization of P(Asp), and both a and b are greater than 0 and less than 1, with the proviso that a+b=1.

As Homo-P(Asp), there is particularly preferred one wherein the number of P(Asp) units representing a polyanionic segment (n in the above formula) is 70 or 82.

Preferred examples for the polymer in (B1) (ii) above include those represented by the following general formulas (VII) and/or (VIII). For the explanation of general formulas (VII) and (VIII), the explanation of general formulas (III) and (IV) may be similarly applied as appropriate.

[Chemical Formula 8]

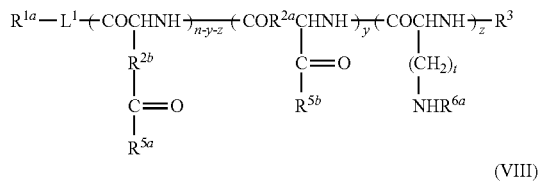

(VII)

(VIII)

According to the invention, preferred specific examples of polymers represented by general formulas (VII) and (VIII) include cationic homopolymers of the following formula, comprising a poly(diaminopentane structure-containing asparagine derivative) (P(Asp-AP)) as a cationic segment (hereinafter referred to as "Homo-P(Asp-AP)").

[Chemical Formula 9]

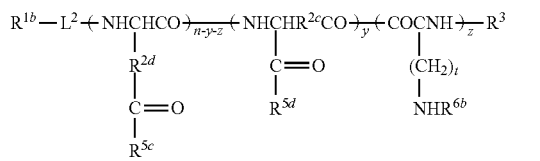

wherein,
n represents an integer indicating the degree of polymerization of P(Asp-AP), and
both a and b are greater than 0 and less than 1, with the proviso that a+b=1.

As Homo-P(Asp-AP), there is particularly preferred one wherein the number of P(Asp-AP) units representing a polycationic segment (n in the above formula) is 70 or 82.

(B2-3: Other Membrane Component)

During formation of the vacant vesicles, an additional membrane component may be added in addition to the first polymer and the second polymer, so long as it does not prevent vesicle formation or reduce stability. The other membrane component is not particularly restricted, and specific examples thereof include charged polymers, charged nanoparticles and the like.

The charged polymer may be any charged polymer that has one or more of the charged segments (cationic segments or anionic segments) mentioned above and that does not correspond to the first polymer or the second polymer.

The charged nanoparticles may be metal-based nanoparticles having an electric charge on the surface, or the like.

The other membrane component mentioned above may be used as a single type, or two or more different types may be used in any combination or proportion.

The amount of the other membrane component used is not restricted, but it is preferably limited so as not to interfere with vesicle formation by self-assembly of the first polymer and the second polymer. Specifically, it will usually be 30% or less, preferably 20% or less, and more preferably 10% or less, relative to the total weight of the vesicle.

(B2-4: Method for Producing Vacant Vesicles)

Since the vacant vesicles that are to encapsulate a substance are formed using electrostatic interaction between the first polymer and the second polymer, it can be easily produced by mixing the first polymer and the second polymer in an aqueous solution. Such a production method allows production of the vesicles even without using an organic solvent, and is therefore advantageous in the fields of DDS, biomaterials and the like.

Specifically, a first aqueous solution containing the first polymer and a second aqueous solution containing the second polymer are prepared. The first and second aqueous solutions may be purified by filtration as desired.

The concentration of the first polymer in the first aqueous solution and the concentration of the second polymer in the second aqueous solution are not restricted, and may be determined, as appropriate, by considering the ratio of the total charge number of the first polymer and the second polymer, the solubility of the first polymer and the second polymer in aqueous solution, the efficiency of vesicle formation, and other conditions.

The type of solvent for the first and second aqueous solutions is not restricted so long as it is an aqueous solvent. It is preferably water, but so long as it does not prevent vesicle formation, the solvent used may be one having another component mixed in water, such as physiological saline, an aqueous buffer, a mixed solvent of water and a water-soluble organic solvent, or the like. One aqueous buffer that may be mentioned is 10 mM HEPES buffer.

The pH of the first and second aqueous solutions may be adjusted as appropriate so long as it does not prevent vesicle formation, and it is preferably pH 5 or higher and more preferably pH 6.5 or higher, and preferably pH 9 or lower and more preferably pH 7.5 or lower. The pH can be easily adjusted using a buffering solution as the solvent. The pH adjustment of the first and second aqueous solutions is advantageous for maintaining the charged state of the first polymer and second polymer and efficiently forming vesicles.

The temperature of the first and second aqueous solutions can be determined as appropriate depending on the solubility in the solvent of the first polymer and the second polymer, but it is preferably 10° C. or higher and more preferably 20° C. or higher, and preferably 80° C. or lower and more preferably 50° C. or lower.

The ionic strength of the first and second aqueous solutions can also be adjusted as appropriate so long as it does not prevent vesicle formation, but it is preferably 0 mM or greater and more preferably 10 mM or greater, and preferably 200 mM or lower and more preferably 50 mM or lower.

The first and second aqueous solutions are mixed to form vesicles. The mixing method is not restricted, and the second aqueous solution may be added to the first aqueous solution or the first aqueous solution may be added to the second aqueous solution. The first and second aqueous solutions may also be simultaneously placed in a vessel for mixing. The mixture of the first and second aqueous solutions that is obtained may be stirred as appropriate.

The temperature at the time of mixing of the first and second aqueous solutions is not restricted so long as it does not prevent vesicle formation, but it is preferably determined by considering the solubility, depending on the temperature of the first polymer and the second polymer. Specifically, it is preferably 10° C. or higher and more preferably 20° C. or higher, and preferably 60° C. or lower and more preferably 50° C. or lower.

After mixing, the formed vacant vesicles may be immediately supplied for a post-loading method, or alternatively a time may be allowed for stationing of the liquid mixture, for equilibration of the system. However, since the diameters of the vesicles that are formed may tend to increase over time, it is usually preferred to immediately provide the vacant vesicles for a post-loading method, without providing a stationing time.

When another membrane component is used, the membrane component may be mixed with the first and second aqueous solutions. In this case, the membrane component may be added to the first and second aqueous solutions before mixing, but preferably there is no aggregation or interaction between the membrane component and the first and second aqueous solutions that would prevent vesicle formation. Also, the membrane component may be added simultaneously during mixing of the first and second aqueous solutions, or the mixing of the first and second aqueous solutions may be followed by addition and further mixing of the membrane component. The other membrane component may be mixed as is, or an aqueous solution containing the membrane component may be prepared and used for mixing. The conditions for preparing an aqueous solution of the membrane component, such as the aqueous solvent used, the pH, the temperature and the ionic strength, are the same as described for the first and second aqueous solutions.

Procedures such as dialysis, dilution, concentration and stirring may also be carried out as appropriate.

[B3: Substance to be Encapsulated]

The substance to be encapsulated in the vesicles is not restricted, and may be selected as appropriate and desired according to the purpose of use, properties, etc. of the substance-encapsulating vesicles.

Specifically, there has been a problem when using a simultaneous mixing method, i.e. the conventional production method, in that when a charged substance is used as the substance to be encapsulated, vesicle formation by self-assembly of polymer membrane structural components is hindered by the electric charge of the substance to be encapsulated, making it impossible to obtain suitable substance-encapsulating vesicles. With a post-loading method, however, there is no such limitation on the electrical properties of the substance to be encapsulated, and thus it is possible to efficiently form substance-encapsulating vesicles whether a charged substance or an uncharged substance is used as the substance to be encapsulated.

Specifically, the type of the substance to be encapsulated may be a biomolecule, an organic compound, an inorganic substance, or the like.

Biomolecules include proteins, polypeptides, amino acids, nucleic acids (DNA, RNA), lipids (fatty acids, glycerides, steroids and the like), carbohydrates (monosaccharides, polysaccharides), and derivatives thereof, as well as two or more thereof bonded together (glycoproteins, glycolipids and the like). Proteins, carbohydrates and the like are preferred among these.

Organic compounds include luminescent (for example, fluorescent and phosphorescent) molecules, water-soluble drugs, water-soluble polymers, water-soluble molecular aggregates (micelles, vesicles, nanogels, etc.) with mean particle sizes of 100 nm or smaller, emulsions with mean particle sizes of 100 nm or smaller, and the like. Among these, polymer micelles with mean particle sizes of 50 nm or smaller and water-soluble polymers with molecular weights of 100,000 or smaller are preferred.

Inorganic substances include water-dispersible metal nanoparticles, oxide nanoparticles (silica nanoparticles, titania nanoparticles, iron oxide nanoparticles and the like), semiconductor nanoparticles (quantum dots and the like), water-soluble carbon clusters, boron clusters, metal complexes, and the like. Among these are preferred quantum dots with mean particle sizes of 20 nm or smaller.

In terms of classification according to use, the substance to be encapsulated may be an anticancer agent (for example, a hydrophobic anticancer agent such as doxorubicin or paclitaxel, a metal complex anticancer agent such as cisplatin or the like, or polymer micelles thereof), a gadolinium or iron compound used in diagnostic MRI or the like, an organic luminescent (fluorescent or phosphorescent, for example) dye, quantum dots, or the like.

The molecular weight and particle size of the substance to be encapsulated is not restricted, but the molecular weight of the substance to be encapsulated may usually be 200,000 or lower and especially 100,000 or lower, and the particle size of the substance to be encapsulated may usually be 100 nm or smaller and more preferably 50 nm or smaller, from the viewpoint of efficiently introducing the substance to be encapsulated into the vacant vesicles.

The ratio of the substance to be encapsulated that is used relative to the vacant vesicles may also be adjusted according to the desired amount of the substance to be encapsulated, within a range that does not destroy the vacant vesicle structure or prevent encapsulation of the substance to be encapsulated in the vacant vesicles.

A single type of substance to be encapsulated may be used alone, or two or more types may be used in any proportion and combination.

[B4 Additional Steps]

A post-loading method need only comprise at least a step of preparing vacant vesicles with a prescribed structure and mixing the vacant vesicles with the substance to be encapsulated in an aqueous medium, but it may further have an additional step.

Examples include treatment with a crosslinking agent, filtration, dialysis, lyophilization and the like.

Among these, when the substance-encapsulating vesicle is to be used in a physiological environment or in the presence of a salt such as physiological saline (for example, for use as a DDS), the formed substance-encapsulating vesicles are preferably subjected to treatment with a crosslinking agent as post-treatment, from the viewpoint of preventing increase in the particle sizes with time. That is, in a physiological environment or in the presence of a salt such as physiological saline, the particle sizes of vesicles having no crosslinking agent may tend to increase with time, but treatment with a crosslinking agent can prevent increase in the particle sizes.

The type of crosslinking agent is not restricted, and it may be selected, as appropriate, according to the purpose of use of the vesicles, the type of the first polymer and second polymer and the type of the other membrane component, for example, but from the viewpoint of efficiently accomplishing crosslinking and enhancing the stability of the substance-encapsulating vesicles, the crosslinking agent preferably reacts with charged groups (for example, cationic groups such as amino groups and anionic groups such as carboxyl groups) in the charged segment of the first polymer and the second polymer but does not react with the substance to be encapsulated. Specific examples of crosslinking agents include crosslinking agents that crosslink amino groups (for example, glutaraldehyde, dimethyl suberimidate dihydrochloride (DMS), dimethyl 3,3'-dithiobispropionimidate (DTBP)), crosslinking agents that crosslink amino groups and carboxyl groups by condensation (for example, 1-ethyl-3-(3-dimethylaminopropyl)carbodiimide (EDC)), and crosslinking agents that crosslink phosphate groups (for example, metal ions such as calcium ions), with glutaraldehyde, EDC and the like being preferred and EDC being especially preferred. A single crosslinking agent may be used alone, or two or more crosslinking agents may be used in any combination and proportion.

The amount of crosslinking agent used is not restricted and may be selected, as appropriate, in consideration of the type of crosslinking agent, the number of crosslinking points, the amount of the component to be crosslinked, and the like, and in the case of a crosslinking agent that crosslinks amino groups and carboxyl groups, for example, the amount used is preferably selected so that the CL ratio defined by the following mathematical formula (iii) satisfies the conditions specified below.

CL ratio (molar ratio)=[Number of moles of crosslinking agent]/[number of moles of carboxyl groups of first and second polymers] [Mathematical Formula 3]

From the viewpoint of efficiently accomplishing crosslinking and enhancing the stability of the substance-encapsulating vesicles, the weight ratio of the crosslinking agent and the first and second polymers is preferably adjusted so that the CL ratio is usually 0.1 or greater and preferably 0.5 or greater. On the other hand, when substance-encapsulating vesicles are used as a DDS in drug delivery (for example, when they are used), the amount of crosslinking agent used is preferably not excessive, from the viewpoint of allowing the drug to be efficiently released at the target site, and specifically the weight ratio of the crosslinking agent and the first and second polymers is preferably adjusted so that the CL ratio is usually 10 or lower and preferably 5 or lower. However, this range for the CL ratio is only approximate, and in reality the CL ratio is preferably adjusted as appropriate for the purpose of use of the vesicles, the type of first polymer and second polymer, the type of other membrane component, and other factors.

[B5: Substance-Encapsulating Vesicles]

By encapsulating a substance in vacant vesicles by any of various desired methods including a post-loading method, it is possible to obtain substance-encapsulating vesicles that encapsulate the aforementioned substance to be encapsulated in the cavities of the vacant vesicles.

The substance-encapsulating vesicles each comprise a membrane formed from a first polymer, which is a block copolymer having an uncharged hydrophilic segment and a first charged segment, and a second polymer, which has a second charged segment having a charge opposite to the charge of the first charged segment, a cavity surrounded by the membrane, and a substance encapsulated in the cavity.

The structure of the membranes of the substance-encapsulating vesicles is essentially the same as the structure of the membranes of the vacant vesicles described above. That is, the substance-encapsulating vesicles preferably have a three-layered structure similar to the structural membranes of the vacant vesicles explained using FIGS. 2 to 4, and the shapes thereof will usually be spherical or approximately spherical.

The particle sizes of the substance-encapsulating vesicles obtained by a post-loading method may vary depending on the conditions such as the structure of the vacant vesicles, the type of substance to be encapsulated, the environment surrounding the vesicles (the type of aqueous medium), the mixing conditions, and the like, but usually they will be approximately equal to the particle sizes of the vacant vesicles. Also, regardless of whether a post-loading method or other method is employed, the particle sizes of the obtained substance-encapsulating vesicles are preferably 10 nm or greater and more preferably 50 nm or greater, and preferably 1000 nm or smaller, more preferably 400 nm or smaller and even more preferably 200 nm or smaller. The same also applies for the particle sizes of the different substance-encapsulating vesicles of the invention described below, unless otherwise specified.

The membrane thickness of the substance-encapsulating vesicles obtained by a post-loading method may also vary depending on the conditions such as the structure of the vacant vesicles, the type of substance to be encapsulated, the environment surrounding the vesicles (the type of aqueous medium), the mixing conditions, and the like, but usually it will be approximately equal to the particle sizes and membrane thickness of the vacant vesicles. Also, regardless of whether a post-loading method or other method is employed, the membrane thickness of the obtained substance-encapsulating vesicles is preferably 5 nm or greater and more preferably 10 nm or greater, and preferably 30 nm or smaller and more preferably 15 nm or smaller. The same also applies for the membrane thicknesses of the different substance-encapsulating vesicles of the invention described below, unless otherwise specified.

By conventional methods it has been possible to encapsulate some substances in electrostatically interacting vesicles (PICsome), but there are limitations on the range of application. Moreover, it has been difficult or impossible to later encapsulate substances into vacant vesicles. By a post-loading method, it becomes possible to produce substance-encapsulating and electrostatically interacting vesicles (substance-encapsulating PICsome) allowing a wide range of substances to be encapsulated in electrostatically interacting vesicles (PICsome).

Since substance-encapsulating vesicles stably retain various substances in the cavities of the vesicles formed by polymer self-assembly, it can be effectively used as a DDS for delivery of a drug, or in various uses such as functional materials carrying active ingredients. For example, by using siRNA (small interfering RNA) as a constituent of the substance to be encapsulated or of the vesicle membranes, the substance-encapsulating vesicles obtained can be used as a DDS or the like for RNAi (RNA interference). It is also possible to allow a plurality of drugs to be encapsulated as substances to be encapsulated, or to use the vesicles in a combination drug therapy, by combined use as the substance to be encapsulated and the membrane material.

[C] Substance-Encapsulating Crosslinked Vesicles and their Production Method

<C-1: First Mode: Monodisperse Population of Substance-Encapsulating Crosslinked Vesicles, and their Production Method>

[General Description]

The method according to the first mode is a method of producing substance-encapsulating crosslinked vesicles, comprising a step of mixing a monodisperse population of vacant crosslinked vesicles with a liquid mixture containing both a target substance and an aqueous medium, and forming a monodisperse population of substance-encapsulating crosslinked vesicles having the target substance encapsulated in the inner aqueous phase.

According to the method of the first mode, the concentration of the target substance contained in the liquid mixture is high enough to inhibit the formation of a monodisperse population of substance-encapsulating non-crosslinked vesicles having the target substance encapsulated in the inner aqueous phase, when a monodisperse population of the vacant non-crosslinked vesicles, differing from the monodisperse population of vacant crosslinked vesicles only in that they are non-crosslinked, has been mixed in the same liquid mixture.

When the monodisperse population of vacant non-crosslinked vesicles is mixed in an aqueous medium in the presence of the target substance, and the concentration of the target substance exceeds a certain level, formation of a monodisperse population of substance-encapsulating non-crosslinked vesicles is sometimes inhibited (that is, a polydisperse population is formed). In contrast, when a monodisperse population of vacant crosslinked vesicles is mixed in an aqueous medium in the presence of the target substance, formation of a monodisperse population of the substance-encapsulating crosslinked vesicles is not inhibited even if a certain concentration is exceeded. Consequently, according to the method of the first mode, it is possible to encapsulate the target substance in the vacant crosslinked vesicles while maintaining its monodisperse property even when the concentration of the target substance in the aqueous medium is at a higher concentration than in conventional methods (for example, a concentration at which formation of a monodisperse population of the substance-encapsulating vesicles is inhibited in a post-loading method), thereby allowing production of a monodisperse population of substance-encapsulating vesicles having a higher concentration of target substance enclosed therein than by the prior art.

[Monodisperse Population of Vacant Crosslinked Vesicles]

The mean particle size of the monodisperse population of the vacant crosslinked vesicles will usually be 30 nm or greater, preferably 50 nm or greater and even more preferably 70 nm or greater, and will usually be 10,000 nm or smaller, preferably 1000 nm or smaller and even more preferably 400 nm or smaller.

Each of the vesicles of the monodisperse population of vacant crosslinked vesicles is a vesicle comprising a crosslinked membrane including the first and second polymers, wherein the first and/or second polymers are crosslinked, and an inner aqueous phase surrounded by the crosslinked membrane, without the target substance being encapsulated in the inner aqueous phase.

The first and second polymers of the vacant crosslinked vesicles are as described above under [B2-2: First and second polymers].

The other membrane component of the vacant crosslinked vesicles is as described above under [B2-3: Other membrane component].

The first and/or second polymer in the crosslinked membranes of the vacant crosslinked vesicles are crosslinked. That is, the crosslinked membranes of the vacant crosslinked vesicles include one or more types of crosslinked bonding selected from the group consisting of crosslinked bonding between the first polymer molecules, crosslinked bonding between the second polymer molecules, and crosslinked bonding between the first polymer and second polymer molecules. From the viewpoint of improving the monodisperse property of the substance-encapsulating crosslinked vesicles that are formed, the crosslinked membranes of the vacant crosslinked vesicles preferably include crosslinked bonds formed between the first polymer and second polymer molecules.

The first and/or second polymer in the crosslinked membrane of the vacant crosslinked vesicles are preferably crosslinked by one or more types of crosslinked bonding selected from the group consisting of crosslinked bonding formed between cationic groups, crosslinked bonding formed between anionic groups and crosslinked bonding formed between cationic groups and anionic groups, and more preferably they are crosslinked by crosslinked bonding formed between cationic groups and anionic groups. The cationic groups and anionic groups are charged groups of the first polymer (first charged segment) and second polymer (second charged segment).

The crosslinking rate may be appropriately adjusted depending on the type of target substance, the type of mixing method used for enclosure of the target substance, and the like, in a range in which the monodisperse property of the vacant crosslinked vesicles is maintained when the target substance is enclosed. Here, "crosslinking rate" refers to the proportion of crosslinked bonds formed out of the total moles of cationic groups and/or anionic groups in the crosslinked membrane, or in other words, for crosslinking between cationic groups, it is the proportion of crosslinked bonds formed between cationic groups out of the total moles of cationic groups in the crosslinked membrane, or for crosslinking between anionic groups, it is the proportion of crosslinked bonds formed between anionic groups out of the total moles of anionic groups in the crosslinked membrane, or for crosslinking between cationic groups and anionic groups, it is the proportion of crosslinked bonds formed between cationic groups and anionic groups out of the total moles of cationic groups and anionic groups in the crosslinked membrane.

A higher crosslinking rate of the vacant crosslinked vesicles results in a smaller maximum molecular size (maximum molecular weight) of target substance that can be enclosed in the vacant crosslinked vesicles, while a lower crosslinking rate of the vacant crosslinked vesicles results in a larger maximum molecular size (maximum molecular weight) of target substance that can be enclosed in the vacant crosslinked vesicles. Thus, a smaller molecular size (molecular weight) of the target substance will correspond to a higher upper limit for the crosslinking rate, while a larger molecular size (molecular weight) of the target substance will correspond to a lower upper limit for the crosslinking rate. From the viewpoint of expanding the range of the molecular size (molecular weight) of target substance that can be enclosed and improving the general utility of the method of the first mode, the crosslinking rate of the vacant crosslinked vesicles is preferably lower.

A higher crosslinking rate of the vacant crosslinked vesicles results in greater maximum applied external force that will allow the monodisperse property of the vacant crosslinked vesicles to be maintained, while a lower crosslinking rate of the vacant crosslinked vesicles results in a smaller maximum applied external force that will allow the monodisperse property of the vacant crosslinked vesicles to be maintained. Thus, a greater external force applied to the vacant crosslinked vesicles requires a higher minimum for the crosslinking rate, while a smaller external force applied to the vacant crosslinked vesicles allows a lower minimum for the crosslinking rate. For example, mixing by ultrasonic irradiation applies a greater external force onto the vacant crosslinked vesicles than mixing by stirring, and therefore the minimum for the crosslinking rate is higher. From the viewpoint of expanding the range of mixing methods that can be used for enclosure of the target substance into the vacant crosslinked vesicles, and improving the general utility of the method of the first mode, the crosslinking rate of the vacant crosslinked vesicles is preferably higher.

When stirring is to be used as the mixing method for enclosure of a target substance with a weight-average molecular weight of 10,000 to 40,000 in vacant crosslinked vesicles, the minimum crosslinking rate is preferably 35%, even more preferably 37% and yet more preferably 38%, and when ultrasonic irradiation is used as the mixing method, the minimum crosslinking rate is preferably 50% and even more preferably 55%. In either case, the maximum crosslinking rate is preferably 80% and even more preferably 75%.

The method of measuring the crosslinking rate may be appropriately selected according to the type of crosslinking agent. In the case of an amide condensation type crosslinking agent such as 1-ethyl-3-(3-dimethylaminopropyl)carbodiimide (EDC), an example of a method of calculating the crosslinking rate may be a method of measuring the crosslinking rate based on the consumption of carboxyl groups ($—COO^-$) as determined from the infrared absorption spectrum. A different method may be method of measuring the crosslinking rate based on the amount of increased amide bonds (—CONH—). However, when the first and second charged segments are polyamino acids or derivatives thereof, the crosslinking rate measuring precision can potentially be reduced since the first and second charged segments contain numerous amide bonds. In such cases, therefore, another measuring method (for example, a measuring method based on consumption of carboxyl groups) is preferably used in combination therewith. Yet another method is a method of calculating the crosslinking rate based on the number of amino group residues as quantified using an amino group coloring reagent. Examples of amino group coloring reagents include trinitrobenzenesulfonic acid, fluorescamine and the like.

The spaces surrounded by the crosslinked membranes (cavities) usually include the aqueous medium used during production of the monodisperse population of the vacant crosslinked vesicles, as an inner aqueous phase.

[Method of Producing a Monodisperse Population of Vacant Crosslinked Vesicles]

The method of producing a monodisperse population of the vacant crosslinked vesicles may be, for example, a method of reacting a monodisperse population of vacant non-crosslinked vesicles with a crosslinking agent that can react with the first and/or second polymer.

Each of the vesicles of the monodisperse population of vacant non-crosslinked vesicles includes the first and second polymers, and is a vesicle comprising a non-crosslinked membrane wherein neither the first nor second polymer is crosslinked, and an inner aqueous phase surrounded by the non-crosslinked membrane, without the target substance being encapsulated in the inner aqueous phase.

The structure of each of the vesicles composing the monodisperse population of the vacant non-crosslinked vesicles is as described above under [B2-1: Vacant vesicle structure].

The mean particle size of the monodisperse population of the vacant non-crosslinked vesicles will usually be 30 nm or greater, preferably 50 nm or greater and even more preferably 70 nm or greater, and will usually be 10,000 nm or smaller, preferably 1000 nm or smaller and even more preferably 400 nm or smaller.

The method for producing the monodisperse population of the vacant non-crosslinked vesicles is as described above under [B2-4: Method for producing vacant vesicles].

The crosslinking agent is not particularly restricted so long as it can react with the first and/or second polymer. The crosslinking agent used may be of a single type or a combination of two or more types, and depending on the type of crosslinking agent used, one or more different types of crosslinked bonds are formed from among the group consisting of crosslinked bonds between the first polymer molecules, crosslinked bonds between the second polymer molecules and crosslinked bonds between the first polymer and second polymer molecules. The crosslinking agent that has participated in the crosslinking reaction may either remain or not remain in the crosslinked bonds. For example, 1-ethyl-3-(3-dimethylaminopropyl)carbodiimide (EDC) does not remain in crosslinked bonds, as explained below.

Crosslinking agents that can react with the first and/or second polymer include crosslinking agents that have two or more functional groups that can react with the functional group of the first polymer and can crosslink between the first polymer molecules (hereunder referred to as "first crosslinking agent"), crosslinking agents that have two or more functional groups that can react with the functional group of the second polymer and can crosslink between the second polymer molecules (hereunder referred to as "second crosslinking agent"), and crosslinking agents that have one or more functional groups that can react with the functional group of the first polymer and one or more functional groups that can react with the functional group of the second polymer, and can crosslink between the first polymer and second polymer molecules (hereunder referred to as "third crosslinking agent"), but from the viewpoint of improving the monodisperse property of the substance-encapsulating crosslinked vesicles that are formed, it is preferred to use a third crosslinking agent, either alone or in combination with another crosslinking agent.

The first to third crosslinking agents preferably can react with the charged groups of the charged segments, among the functional groups of the first and/or second polymers. That is, the first crosslinking agent preferably can crosslink between charged groups of the first charged segment, the second crosslinking agent preferably can crosslink between charged groups of the second charged segment, and the third crosslinking agent preferably can crosslink between charged groups of the first charged segment and charged groups of the second charged segment.

Cationic groups that can react with the first to third crosslinking agents are preferably amino groups. Anionic groups that can react with the first to third crosslinking agents may be carboxyl or phosphate groups, for example, and are preferably carboxyl groups.

Functional groups that can react with the first to third crosslinking agents are not charged under neutral conditions, but they are preferably functional groups that are charged under specified conditions, examples of such functional groups including phenol derivatives, pyridine derivatives, imidazole derivatives, thiol derivatives and the like. These functional groups can also be molecularly designed so as to be charged under neutral conditions.

Examples of crosslinking agents that crosslink amino groups include glutaraldehyde, dimethyl suberimidate dihydrochloride (DMS), dimethyl 3,3'-dithiobispropionimidate (DTBP), disuccinimide derivatives such as disuccinimidyl glutarate (DSG) and disuccinimidyl suberate (DSS), difluorobenzene derivatives such as 1,5-difluoro-2,4-dinitrobenzene (DFDNB), and (THPP), and bismaleimide derivatives such as 3-[tris(hydroxymethyl)phosphonio] propionate (THPP).

Examples of crosslinking agents that condense amino and carboxyl groups to produce crosslinking (and therefore the crosslinking agent does not remain in the crosslinked bond) include carbodiimide-based condensation agents such as 1-ethyl-3-(3-dimethylaminopropyl)carbodiimide (EDC), N,N'-dicyclohexanecarbodiimide (DCC) and diisopropylcarbodiimide, N,N'-carbonyldiimidazole (CDI), and 4-(4,6-dimethoxy-1,3,5-triazin-2-yl)-4-methylmorpholinium chloride n-hydrate (DMT-MM).

Crosslinking agents that crosslink amino and phosphoric acid groups include a crosslinking agent based on the combination of EDC and imidazole.

Examples of crosslinking agents that crosslink phosphate groups include metal ions such as calcium ion.

EDC is a preferred crosslinking agent. EDC does not remain in crosslinked bonds. Thus, when the vesicles are to be administered to the body (for example, when they are to be administered to the body as drug delivery vesicles), in vivo degradation of the vesicles does not result in release of the crosslinking agent and cytotoxicity.

The amount of crosslinking agent used may be appropriately adjusted depending on the type of crosslinking agent, the amount of components to be crosslinked, the type of target substance, the type of mixing method used for enclosure of the target substance in the vacant crosslinked vesicles, and the like, so that the desired crosslinking rate is achieved.

Assuming that a crosslinking agent that crosslinks amino groups and carboxyl groups (such as EDC) is used as the crosslinking agent for enclosure of a target substance with a weight-average molecular weight of 10,000 to 40,000 in vacant crosslinked vesicles, the amount of crosslinking agent used is preferably in the following range. Specifically, when the mixing is by stirring during encapsulation, the amount of crosslinking agent used is adjusted so that the CL ratio as specified by formula (iii) above is preferably 0.3 or greater and more preferably 0.5 or greater, and preferably 1.2 or smaller and more preferably 1.0 or smaller. Specifically, when the mixing is to be by ultrasonic waves during enclosure, the amount of crosslinking agent used is adjusted so that the CL ratio as specified by formula (iii) above is preferably 0.8 or greater and more preferably 1.0 or greater, and preferably 4.0 or smaller and more preferably 3.0 or smaller.

[Liquid Mixture]

The liquid mixture contains the target substance together an aqueous medium.

The target substance is the substance that is to be encapsulated in the vesicles, and it may be selected as appropriate according to the purpose of use of the vesicles.

The target substance is as described above under [B3: Substance to be encapsulated], and the aqueous medium is as described above under [B1-3: Other conditions for mixing].

The concentration of the target substance contained in the liquid mixture is a concentration sufficient to inhibit the formation of a monodisperse population of substance-encapsulating non-crosslinked vesicles having the target substance encapsulated in the inner aqueous phase, when a monodisperse population of the vacant non-crosslinked vesicles, differing from the monodisperse population of vacant crosslinked vesicles only in that the first and/or second polymers are not crosslinked, has been mixed in the same liquid mixture.

Each of the vesicles of the monodisperse population of vacant non-crosslinked vesicles includes the first and second polymers, and is a vesicle comprising a non-crosslinked membrane wherein neither the first nor second polymer is crosslinked, and an inner aqueous phase surrounded by the non-crosslinked membrane, without the target substance being encapsulated in the inner aqueous phase.

Each of the vesicles composing the monodisperse population of substance-encapsulating non-crosslinked vesicles includes the first and second polymers, and is a vesicle comprising a non-crosslinked membrane wherein neither the first nor second polymer is crosslinked, and an inner aqueous phase surrounded by the non-crosslinked membrane, with the target substance being encapsulated in the inner aqueous phase.

The monodisperse population of the vacant non-crosslinked vesicles differs from the vacant crosslinked vesicles in that the first and/or second polymers are not crosslinked. The monodisperse population of the vacant non-crosslinked vesicles is preferably essentially identical to the monodisperse population of the vacant crosslinked vesicles in all aspects other than crosslinking, so that whether or not a monodisperse population of substance-encapsulating vesicles is formed depends only on the presence or absence of crosslinking. Furthermore, the conditions during mixing of the monodisperse population of the vacant non-crosslinked vesicles in the liquid mixture (the liquid mixture composition, mixing method, etc.) also are preferably essentially identical to the conditions during mixing of the monodisperse population of the vacant crosslinked vesicles in the liquid mixture, so that whether or not a monodisperse population of substance-encapsulating vesicles is formed depends only on the presence or absence of crosslinking.

When the monodisperse population of vacant non-crosslinked vesicles is mixed in an aqueous medium in the presence of the target substance, and the concentration of the target substance in the liquid mixture exceeds a certain level, formation of a monodisperse population of substance-encapsulating vesicles is inhibited (that is, a polydisperse population is formed). This certain level of concentration differs depending on the type of target substance. For example, when the molecular weight of the target substance is 10,000 to 40,000, it will usually be a concentration above 5 mg/mL, preferably 15 mg/mL and more preferably 40 mg/mL.

When the target substance is a poorly water-soluble substance, an increasing concentration of the poorly water-soluble substance in the liquid mixture will result in a more notable effect of the method of the first mode. That is, when the monodisperse population of vacant non-crosslinked vesicles are mixed in the liquid mixture, and the concentration of the poorly water-soluble substance in the liquid mixture exceeds a certain level, formation of a monodisperse population of substance-encapsulating non-crosslinked vesicles is sometimes inhibited (that is, a polydisperse population is formed). In contrast, when a monodisperse population of vacant crosslinked vesicles is mixed in a liquid mixture, formation of a monodisperse population of the substance-encapsulating crosslinked vesicles is not inhibited even if a certain concentration is exceeded. Consequently, the concentration of the poorly water-soluble substance in the liquid mixture is preferably a concentration such that formation of a monodisperse population of the substance-encapsulating non-crosslinked vesicles is inhibited when the vacant non-crosslinked vesicles are mixed in the same liquid mixture. Such a concentration will usually be higher than the solubility of the poorly water-soluble substance (the poorly water-soluble substance being dispersed or suspended in the liquid mixture in this case). The term "poorly water-soluble" here means poorly soluble or insoluble in aqueous media, and when the aqueous medium is water, for example, it means that the solubility in water at 25° C. is usually no greater than 1.0 mg/mL, preferably no greater than 0.1 mg/mL and more preferably no greater than 0.02 mg/mL.

The concentration of the vacant crosslinked vesicles mixed in the liquid mixture may be appropriately adjusted within a range such that the vesicles do not aggregate. If the concentration of the vacant crosslinked vesicles is too low, substance-encapsulating vesicles may not form after mixing, and therefore the concentration of the vacant crosslinked vesicles is preferably a high concentration within a range such that the vesicles do not aggregate. The concentration of the vacant crosslinked vesicles will usually be 0.1 mg/mL or higher, preferably 1 mg/mL or higher and more preferably 10 mg/mL or higher, and usually 100 mg/mL or lower, preferably 70 mg/mL or lower and more preferably 50 mg/mL or lower. Because the particle sizes of the obtained substance-encapsulating vesicles may depend on the concentration of the vacant crosslinked vesicles, the concentration of the vacant crosslinked vesicles should be determined according to the particle sizes of the substance-encapsulating vesicles that are to be produced.

There is no particular restriction on the pH of the liquid mixture, and it may be appropriately adjusted according to the structure of the vacant crosslinked vesicles, the type of target substance, the concentrations of the vacant crosslinked vesicles and target substance in the liquid mixture, and other factors, but it is preferably pH 5 or higher and more preferably pH 6.5 or higher, and preferably no higher than pH 9 and more preferably no higher than pH 7.5. The pH can be easily adjusted using a buffering solution as the solvent. Adjusting the pH of the liquid mixture is advantageous for maintaining the structure of the vacant crosslinked vesicles and for efficiently encapsulating the target substance in the vacant crosslinked vesicles.

The salt concentration (ionic strength) of the liquid mixture may be appropriately adjusted within a range such that the structure of the vacant crosslinked vesicles does not disintegrate and encapsulation of the target substance in the vacant crosslinked vesicles is not inhibited. However, the method of the first mode has a more notable effect with increased salt concentration (ionic strength) of the liquid mixture. That is, when the monodisperse population of vacant non-crosslinked vesicles is mixed in the liquid mixture, and the salt concentration in the liquid mixture exceeds a certain value, formation of monodisperse population of substance-encapsulating non-crosslinked vesicles is inhibited (that is, a polydisperse population is formed). In contrast, when a monodisperse population of vacant crosslinked vesicles is mixed in a liquid mixture, formation of a monodisperse population of the substance-encapsulating crosslinked vesicles is not inhibited even if the certain value is exceeded. Consequently, the salt concentration in the liquid mixture is preferably a concentration such that formation of a monodisperse population of the substance-encapsulating non-crosslinked vesicles is inhibited when the vacant non-crosslinked vesicles are mixed in the same liquid mixture. The salt concentration of the liquid mixture is preferably 20 mM or higher, more preferably 75 mM or higher and even more preferably 150 mM or higher, in terms of the sodium chloride concentration. The upper limit for the salt concentration of the liquid mixture will usually be 1.0 M and preferably 0.5 M.

The viscosity of the liquid mixture may be appropriately adjusted within a range such that the structure of the vacant crosslinked vesicles does not disintegrate and encapsulation of the target substance in the vacant crosslinked vesicles is not inhibited. However, the method of the first mode has a more notable effect with increased viscosity of the liquid mixture. That is, when the monodisperse population of vacant non-crosslinked vesicles is mixed in the liquid mixture, and the viscosity of the liquid mixture exceeds a certain value, formation of a monodisperse population of substance-encapsulating non-crosslinked vesicles is inhibited (that is, a polydisperse population is formed). In contrast, when a monodisperse population of vacant crosslinked vesicles is mixed in a liquid mixture, formation of a monodisperse population of the substance-encapsulating crosslinked vesicles is not inhibited even if the certain value is exceeded. Consequently, the viscosity of the liquid mixture is preferably a viscosity such that formation of a monodisperse population of the substance-encapsulating non-crosslinked vesicles is inhibited when the vacant non-crosslinked vesicles are mixed in the same liquid mixture. The viscosity of the liquid mixture is preferably 0.05 Pa·s or higher, more preferably 0.1 Pa·s or higher and even more preferably 0.5 Pa·s or higher. The upper limit for the viscosity of the liquid mixture will usually be 1.0 Pa·s and preferably 0.7 Pa·s.

The temperature of the liquid mixture is not restricted, so long as it is in a range that does not destroy the structure of the vacant crosslinked vesicles or inhibit encapsulation of the target substance in the vacant crosslinked vesicles, and it is preferably 4° C. or higher and more preferably 20° C. or higher, and preferably no higher than 80° C. and more preferably no higher than 50° C.

[Mixing Method]

The mixing method is as described above under [B1-2: Mixing of vacant vesicles and substance to be encapsulated].

When the target substance is a poorly water-soluble substance, the mixing method is preferably one employing ultrasonic treatment.

[Additional Steps]

The method according to the first mode may include other steps in addition to the step of mixing a monodisperse population of vacant crosslinked vesicles with a liquid mixture containing both a target substance and an aqueous medium, and forming a monodisperse population of substance-encapsulating crosslinked vesicles having the target substance encapsulated in the inner aqueous phase. For example, it may include as a later step, a step of crosslinking the substance-encapsulating crosslinked vesicles obtained by mixing the vacant crosslinked vesicles in the liquid mixture. The crosslinking agent to be used in such a crosslinking step is a crosslinking agent that can react with the first and/or second polymer, the details of which are the same as described above.

[Monodisperse Population of Substance-Encapsulating Crosslinked Vesicles]

By the method of the first mode there are produced a monodisperse population of substance-encapsulating crosslinked vesicles comprising a crosslinked membrane including the first and second polymers, the first and/or second polymers being crosslinked, and an inner aqueous phase surrounded by the crosslinked membrane, with the target substance being encapsulated in the inner aqueous phase.

In the monodisperse population of the substance-encapsulating crosslinked vesicles, the concentration of the target substance contained in the inner aqueous phase is a concentration sufficient to inhibit the formation of a monodisperse population of substance-encapsulating non-crosslinked vesicles having the target substance encapsulated in the inner aqueous phase, when a monodisperse population of the vacant non-crosslinked vesicles, differing from the monodisperse population of substance-encapsulating crosslinked vesicles in that the first and/or second polymers are not crosslinked and the target substance is not encapsulated, has been mixed in a liquid mixture containing the target substance at the same concentration as the inner aqueous phase of the substance-encapsulating crosslinked vesicles, together with an aqueous medium.

Stated differently, the substance-encapsulating crosslinked vesicles produced by the method of the first mode have a higher monodisperse property than substance-encapsulating non-crosslinked vesicles obtained by mixing a monodisperse population of vacant non-crosslinked vesicles in a liquid mixture containing the target substance at the same concentration as the inner aqueous phase of the substance-encapsulating crosslinked vesicles, together with an aqueous medium.

The inner aqueous phase of the substance-encapsulating crosslinked vesicles varies depending on the liquid mixture used in the method of the first mode. For example, when the salt concentration of the liquid mixture is 20 mM or higher in terms of the sodium chloride concentration, the salt concentration of the inner aqueous phase will be as well. Also, when the viscosity of the liquid mixture is 0.05 Pa·s or higher, the viscosity of the inner aqueous phase will be as well. Furthermore, when the liquid mixture contains a target substance with a weight-average molecular weight of 10,000 to 40,000 at a concentration exceeding 5 mg/mL, the inner aqueous phase will as well. In addition, when the liquid mixture contains a poorly water-soluble substance at a higher concentration than its solubility, the inner aqueous phase will as well.

The crosslinking rate of the substance-encapsulating crosslinked vesicles will vary depending on the crosslinking rate of the vacant crosslinked vesicles used in the method of the first mode, and the presence or absence of a crosslinking step carried out as a later step. For example, in the vacant crosslinked vesicles, the first and/or second polymer are crosslinked by one or more types of crosslinked bonding selected from the group consisting of crosslinked bonding formed between cationic groups, crosslinked bonding formed between anionic groups and crosslinked bonding formed between cationic groups and anionic groups, and more preferably they are crosslinked by crosslinked bonding formed between cationic groups and anionic groups, and when the proportion of crosslinked bonds formed is 35% or more of the total moles of cationic groups and/or anionic groups in the crosslinked membrane, the crosslinking rate of the substance-encapsulating crosslinked vesicles obtained by mixing the vacant crosslinked vesicles in the liquid mixture will be the same as that of the vacant crosslinked vesicles, so that the crosslinking rate will increase compared to the vacant crosslinked vesicles when a crosslinking step is carried out as a later step.

<C-2: Second Mode: Multiple Different Substance-Encapsulating Crosslinked Vesicles, and their Production Method>
[General Description]

The method according to the second mode is a method of producing multiple different substance-encapsulating crosslinked vesicles, comprising a step of mixing first substance-encapsulating crosslinked vesicles in which a first target substance has been encapsulated, with a liquid mixture containing a second target substance having a smaller molecular weight than the first target substance, together with an aqueous medium, and forming second substance-encapsulating crosslinked vesicles in which the first and second target substances have been encapsulated.

When the first substance-encapsulating crosslinked vesicles in which the first target substance has been encapsulated is mixed in the aqueous medium in the presence of the second target substance, the second target substance becomes enclosed in the first substance-encapsulating crosslinked vesicles, while maintaining enclosure of the first target substance. According to the method of the second mode, therefore, it is possible to enclose the first and second target substances while controlling their enclosure amounts, thereby allowing production of substance-encapsulating vesicles with controlled enclosure amounts of the first and second target substances.

[First Substance-Encapsulating Crosslinked Vesicles]

The first substance-encapsulating crosslinked vesicles are vesicles comprising a crosslinked membrane that includes the first and second polymers, the first and/or second polymers being crosslinked, and an inner aqueous phase surrounded by the crosslinked membrane, with the first target substance being encapsulated in the inner aqueous phase.

The construction of the first substance-encapsulating crosslinked vesicles is the same as the construction of the substance-encapsulating crosslinked vesicles in the method of the first mode, except that the target substance is the first target substance.

The first substance-encapsulating crosslinked vesicles preferably form a monodisperse population. By using monodisperse population as the first substance-encapsulating crosslinked vesicles, it is possible to produce second substance-enclosing crosslinked vesicles as their monodisperse population.

The mean particle size of the monodisperse population of the first substance-encapsulating crosslinked vesicles will usually be 30 nm or greater, preferably 50 nm or greater and even more preferably 70 nm or greater, and will usually be 10,000 nm or smaller, preferably 1000 nm or smaller and even more preferably 400 nm or smaller.

[Method of Producing First Substance-Encapsulating Crosslinked Vesicles]

Examples of methods for producing the first substance-encapsulating crosslinked vesicles include a method in which vacant crosslinked vesicles comprising a crosslinked membrane that includes the first and second polymers, the first and/or second polymers being crosslinked, and an inner aqueous phase surrounded by the crosslinked membrane, without the first and second target substances being encapsulated in the inner aqueous phase, are mixed in a liquid mixture containing a first target substance together with an aqueous medium, and after mixing, if necessary, reacting them with a crosslinking agent that can react with the first and/or second polymer (hereunder referred to as "method 1"), or a method in which substance-encapsulating non-crosslinked vesicles comprising a non-crosslinked membrane that includes the first and second polymers, neither the first nor second polymer being crosslinked, and an inner aqueous phase surrounded by the non-crosslinked membrane, with the first target substance encapsulated in the inner aqueous phase, are reacted with a crosslinking agent that can react with the first and/or second polymer (hereunder referred to as "method 2").

Method 1 may be carried out in the same manner as the method of the first mode, except that the first target substance is used as the target substance.

The substance-encapsulating non-crosslinked vesicles used in method 2 may be produced, for example, by a simultaneous mixing method or a post-loading method. A simultaneous mixing method is a method of mixing the first polymer, second polymer and target substance in an aqueous medium, while a post-loading method is a method of mixing the vacant vesicles in a liquid mixture containing the first substance together with an aqueous medium.

The crosslinking agent used in method 2 is the same as the crosslinking agent used in the method of the first mode.

Both method 1 and method 2 allow production of first substance-encapsulating crosslinked vesicles as their monodisperse population.

When method 1 is used as the method of producing the first substance-encapsulating crosslinked vesicles, preferably the vacant crosslinked vesicles form their monodisperse population, and the first substance-encapsulating crosslinked vesicles form their monodisperse population. When the vacant crosslinked vesicles used form their monodisperse population, an effect similar to that of the method of the first mode is obtained if the concentration of the first target substance contained in the liquid mixture is a concentration sufficient to inhibit the formation of a monodisperse population of substance-encapsulating non-crosslinked vesicles having the first target substance encapsulated in the inner aqueous phase, when a monodisperse population of the vacant non-crosslinked vesicles, differing from the monodisperse population of vacant crosslinked vesicles only in that the first and/or second polymers are not crosslinked, has been mixed in the same liquid mixture.

[Liquid Mixture]

The liquid mixture contains a second target substance having a smaller molecular weight than the first target substance, together with an aqueous medium.

The second target substance is not particularly restricted so long as its molecular weight is lower than that of the first target substance, and it may be appropriately selected according to the purpose of use of the vesicles. Specific examples for the first and second target substances include the same specific examples for the target substance to be used in the method of the first mode.

A preferred example for the second target substance is a crowding agent. A crowding agent produces a molecular crowding environment (a crowded molecular environment). A crowding agent is a water-soluble molecule that does not interact with the first target substance and has sufficient solubility to produce a molecular crowding environment, and specific examples thereof include hydrophilic polymers such as polyethylene glycol, sugar polymers (dextran, Ficoll$^R$) and albumin protein, and hydrophilic low molecular weight compounds such as glycerol, ethylene glycol and diethylene glycol.

The aqueous solvent is the same as the aqueous medium used in the method of the first mode.

The liquid mixture composition, pH, salt concentration (ionic strength), viscosity, etc. are the same as for the liquid mixture used in the method of the first mode.

When the vacant crosslinked vesicles used form their monodisperse population, an effect similar to that of the method of the first mode is obtained if the concentration of the second target substance contained in the liquid mixture is a concentration sufficient to inhibit the formation of a monodisperse population of second substance-encapsulating non-crosslinked vesicles having the first and second target substances encapsulated in the inner aqueous phase, when a monodisperse population of the first substance-encapsulating non-crosslinked vesicles, differing from the a monodisperse population of first substance-encapsulating crosslinked vesicles only in that the first and/or second polymers are not crosslinked, has been mixed in the liquid mixture.

[Mixing Method]

The mixing method is the same as in the method of the first mode.

[Substance-Encapsulating Crosslinked Vesicles]

By the method of the second mode there are produced substance-encapsulating crosslinked vesicles comprising a crosslinked membrane including the first and second polymers, the first and/or second polymers being crosslinked, and an inner aqueous phase surrounded by the crosslinked membrane, with the first and second target substances being encapsulated in the inner aqueous phase.

As an application for substance-encapsulating crosslinked vesicles having first and second target substances encapsulated therein, there may be mentioned the goal of stabilizing the first target substance, by using the second target substance to create a molecular crowding environment. That is, according to one mode of the substance-encapsulating crosslinked vesicles, the first target substance is more stable than when it is present in the inner aqueous phase in the absence of the second target substance. Such stabilization of the first target substance can be achieved by controlling the amount of enclosure of the second target substance. In this case a crowding agent is preferably used as the second target substance. By using a crowding agent as the second target substance, it is possible to increase the pH stability of the first target substance, for example.

[D] Adsorbent-Encapsulating Vesicles and their Production Method

Another mode of the invention relates to vesicles encapsulating adsorbent particles (or "adsorbent-encapsulating vesicles") and their production method.

As a result of ardent research, the present inventors have found that by encapsulating particles having a substance-adsorbing property (adsorbent particles) in electrostatically interacting vesicles formed by self-assembly of two different polymers having opposite electrical charges, it is possible to obtain novel substance-encapsulating vesicles (adsorbent-encapsulating vesicles) encapsulating relatively large particles with respect to the sizes of the vesicles. In addition, it was found that by mixing one of the two types of polymer with the adsorbent particles and then mixing the other polymer, such adsorbent-encapsulating vesicles can be very efficiently obtained. This mode is based on the aforementioned finding.

The adsorbent-encapsulating vesicles of the invention comprise vesicles composed of a membrane comprising a first polymer, which is block copolymer having an uncharged hydrophilic segment and a first charged segment, and a second polymer, which has a second charged segment having a charge opposite to the charge of the first charged segment, and adsorbent particles encapsulated in the vesicles, wherein either or both of the first and second polymers are adsorbed onto the adsorbent particles.

The first and second polymers are as described above under [B].

As used herein, "adsorbent particles" refers to particles having activity of adsorbing substances. Here, "adsorption" refers to the phenomenon in which the concentration of a substance increases at the interface of two phases (in this case, solid particles and their surrounding liquid phase), compared to the surroundings. There is no restriction on the type of adsorption action of the adsorbent particles, and it may be physical adsorption (adsorption by physical interaction) or chemical adsorption (adsorption with chemical bonding), or a combination thereof. With physical adsorption, the physical interaction on which it is based may be ion-ion interaction, dipole-dipole interaction, van der Waals forces, or the like, or two or more of these in combination.

With chemical adsorption, the chemical bonding on which it is based may be hydrogen bonding, covalent bonding, coordination bonding, ionic bonding or the like, or two or more of these in combination.

However, the adsorbent particles are preferably particles having surface electric charge and exhibiting dispersibility in aqueous media. If the adsorbent particles have such properties, the first and/or second polymer as the constituent elements of the vesicles will be easily adsorbed onto the adsorbent particles by electrostatic interaction, presumably promoting formation of vesicles near the adsorbent particle surfaces. Specifically, the absolute value of the zeta potential of the particle surfaces is usually 10 mV or greater, preferably 20 mV or greater and more preferably 30 mV or greater. The zeta potential of the particle surfaces can be measured, for example, using an electrophoresis method such as light scattering electrophoresis.

Also, from the viewpoint of increasing the adsorption capacity, the adsorbent particles are preferably particles with a large area-to-weight ratio. Particles with a large area-to-weight ratio include various types of porous particles. For porous particles, the pore volume of the particles is 0.1 $cm^3/g$ or greater and preferably 0.5 $cm^3/g$ or greater. The area-to-weight ratio of the particle surfaces and the pore properties such as the pore volume of porous particles can be measured by the BET method, for example.

The type of adsorbent particles is not restricted, and examples include particles made of materials including different metal oxides such as silica, calcium phosphate, calcium carbonate, alumina, zeolite and iron oxide; simple metals such as gold, platinum and palladium; and synthesis or natural resins such as polystyrene resin, styrene-divinylbenzene resin, ion exchange resins, polyacrylic acid fine particles, polylactic acid fine particles, and lactic acid-glycolic acid copolymer fine particles. Preferred among these are silica, calcium phosphate, gold and polyacrylic acid fine particles.

The nature of the adsorbent particles is not restricted, and although they may be solid particles, they may instead form a colloid or gel in the aqueous medium. Also, they may be of a substance that is not an adsorbent or particulate at first, but is converted to adsorbent particles after having been encapsulated in the vesicles. An example of such a mode will be described below.

There is no restriction on the sizes of the adsorbent particles, but according to the present invention even large-sized particles (for example, larger than 30 nm) that have been difficult to encapsulate in conventional electrostatically interacting vesicles can be encapsulated, and such large-sized adsorbent particles are preferred for use. Of these, adsorbent particles having sizes of usually 40 nm or larger, 50 nm or larger or even 60 nm or larger are preferred. There is no restriction on the upper limit for the mean particle size, but it will usually be no greater than about 10 µm. The mean particle size of the adsorbent particles will depend on the type of adsorbent, but normally it can be measured by a method such as dynamic light scattering (DLS), transmission electron microscopy (TEM), scanning electron microscopy (SEM), laser diffraction or the Coulter counter method.

The adsorbent-encapsulating vesicles of the invention can encapsulate relatively large adsorbent particles with respect to the sizes of the vesicles. For example, in Example 1 described below, the mean particle size of the adsorbent particles to be encapsulated (mesoporous silica nanoparticles: MSN) is about 80 nm, whereas the mean particle size of the obtained adsorbent-encapsulating vesicles is about 100 nm, and therefore despite the very large particle sizes of the adsorbent particles with respect to the vesicle particle sizes, adsorbent-encapsulating vesicles were obtained that encapsulate them with high encapsulation efficiency. While the reason is not completely understood, it is thought that the first and/or second polymer may undergo self-assembly while adsorbed onto the adsorbent particles, thus efficiently forming vesicles around the adsorbent particles.

The adsorbent-encapsulating vesicles of the invention can be produced by mixing the first and second polymers together with the adsorbent particles, in any desired order, and usually in an aqueous medium.

However, from the viewpoint of increasing the encapsulation efficiency of the adsorbent particles in the vesicles, they are preferably produced by a method including at least (a) a step of mixing either one of the first and second polymers with the adsorbent particles in an aqueous medium, and adsorbing it onto the adsorbent particles, and (b) adding the other polymer to the mixture containing the aqueous medium and mixing it therewith to form vesicles comprising membranes containing the first and second polymers surrounding the adsorbent particles (i.e., the method of producing adsorbent-encapsulating vesicles of the invention). By this production method it is possible to vastly increase the encapsulation efficiency for adsorbent particles and efficiently create desired adsorbent-encapsulating vesicles.

In step (a), the polymer adsorbed onto the adsorbent particles first may be either one (the first or second polymer). From the viewpoint of production efficiency for the adsorbent-encapsulating vesicles, however, the polymer having a charge opposite to the surface charge of the adsorbent particles is preferably contacted with the adsorbent particles first. For example, when the surface charge of the adsorbent particles is positive, it is preferably the polymer with a negative charge (that is, the polymer having an anionic segment), and when the surface charge of the adsorbent particles is negative, it is preferably the polymer with a positive charge (that is, the polymer having a cationic segment). When the positive and negative charges are mixed on the adsorbent particle surfaces, the positivity or negativity may be judged by comprehensively considering the overall surface charge of the adsorbent particles. However, as already stated, it is possible to obtain adsorbent-encapsulating vesicles of the invention with contact of either of the polymers with the adsorbent particles first.

The type of aqueous medium, the concentrations of the first and second polymers and the adsorbent particles, the mixing method, and other conditions for production, may be the same conditions described above under [B], or those conditions with appropriate modifications.

By this production method, vesicles are formed that comprise membranes containing the first and second polymers surrounding adsorbent particles, whereby adsorbent-encapsulating vesicles are obtained. When charged particles are used as the adsorbent particles, the adsorbent-encapsulating vesicles and the adsorbent particles that are not encapsulated in the vesicles can be distinguished by their surface zeta potential, for example. Specifically, charged adsorbent particles have a large absolute value for the surface zeta potential while the adsorbent-encapsulating vesicles having adsorbent particles encapsulated by vesicles have their charge canceled out by electrostatic interaction of the first and second polymers, and therefore have a small absolute value for the surface zeta potential. Thus, it is possible to confirm formation of adsorbent-encapsulating vesicles by confirming reduction in the absolute value of the surface zeta potential, and considering the particle properties as determined by DLS measurement and the results of TEM observation and the like.

While the reason for the increase in encapsulation efficiency of adsorbent particles by this method is not completely understood, our conjecture is as follows. Specifically, in this production method, the adsorbent particles are not encapsulated in the vesicles after self-assembly but rather the first or second polymer is adsorbed onto the adsorbent particles to be encapsulated, and then the other polymer is added, thereby forming the membranes of the vesicles near the adsorbent particle surfaces. In other words, it is believed that by using the adsorbent particles as templates at the time of vesicle formation, the concentration of the charged polymer (either the first or second polymer) is selectively increased in the microenvironment near the adsorbent particles (presumably a type of adsorption), such that when the polymer having the opposite charge (the other of the first or second polymer) is added, selective self-assembly takes place near the surfaces of the adsorbent particles. As a result, substances that normally can only be enclosed to a percentage corresponding to the number density in the solution can be encapsulated with very high encapsulation efficiency. Also, even when adsorbent particles with relatively large sizes are to be encapsulated, it is believed that, for the same reason, the polymers undergo self-assembly while adsorbed onto the adsorbent particle surfaces, efficiently forming vesicles surrounding the adsorbent particles and thus allowing encapsulation to be accomplished.

In the production method for adsorbent-encapsulating vesicles according to the invention, steps other than those described above may be carried out in addition. A preferred example is crosslinking of the first and/or second polymer in the vesicles after formation of the adsorbent-encapsulating vesicles. Crosslinking can increase the stability of the vesicles. By crosslinking the polymer it is possible to stably maintain the vesicles even under physiological conditions, when the adsorbent-encapsulating vesicles are to be used as a DDS, for example. The method for crosslinking the first and/or second polymer will be explained separately.

Also, a step of surface treatment of the adsorbent may be carried out before, during or after formation of the adsorbent-encapsulating vesicles. Carrying out surface treatment can provide different functional groups on the adsorbent surfaces, or modify the various properties of the adsorbent surfaces. The type of surface treatment is not particularly restricted, and when silica particles are used as the adsorbent, for example, treatment may be with various forms of silane coupling agents or the like. There are no particular restrictions on types of silane coupling agents, and examples include treatment with an aminated silane coupling agent such as 3-aminopropyltrimethoxysilane or 3-aminopropyltriethoxysilane, for example, when a cationic group is to be provided on the surface. Also, when an anionic group is to be provided on the surface, for example, treatment with a mercaptized silane coupling agent such as 3-mercaptopropyltrimethoxysilane or 3-mercaptopropylmethyldimethoxysilane may be followed by oxidation of the mercapto group for conversion to a sulfonate sulfonate group. Alternatively, surface treatment may be carried out using p-styryltrimethoxysilane, vinyltrimethoxysilane, vinyltriethoxysilane, 3-acryloxypropyltrimethoxysilane, 3-methacryloxypropyltrimethoxysilane or the like, which can provide aromatic ring hydrophobicity, π electron interaction and the like. Naturally, the surface treatment is not limited to these types of treatment, and any desired surface treatment may be selected as appropriate depending on the desired properties and purpose of use, the type of adsorbent to be used, the type of substance to be adsorbed onto the adsorbent (described below), and the like.

Furthermore, according to the invention, another substance may also be adsorbed onto the adsorbent particles that have been encapsulated in the vesicles. In particular, even compounds with low molecular weights (for example, 5000 Da and smaller), which have been difficult to stably encapsulate with conventional electrostatically interacting vesicles, can be stably encapsulated in vesicles according to the invention while in a state of being adsorbed and carried on the adsorbent particles. This allows the adsorbent-encapsulating vesicles of the invention to be suitably used for purposes such as carrying and release of low molecular weight compounds such as various drugs. In particular, by using particles that have a surface charge and exhibit dispersibility in aqueous medium as the adsorbent particles, as described above, it is possible to realize an excellent DDS that can stably exist under physiological conditions, while also being able to release a low molecular weight compound such as any of various drugs carried on adsorbent particles, under physiological conditions. Furthermore, depending on the type of low molecular weight compound, such as a drug, that is to be carried, the adsorption and carrying properties can be improved by surface treatment of the adsorbent as described above.

Adsorption and loading of the low molecular weight compound on the adsorbent particles may be carried out either before or after encapsulation of the adsorbent particles in the vesicles, but since the physicochemical properties of the adsorbent particles will also be affected by the physicochemical properties of the low molecular weight compound to be adsorbed, it is considered preferable to be after encapsulation of the adsorbent particles in the vesicles.

As a modified example of this mode, substance-encapsulating vesicles may be prepared having introduced therein a substance that can form an adsorbent (adsorbent precursor), subsequently converting the adsorbent precursor to an adsorbent for formation of adsorbent-encapsulating vesicles. Examples of adsorbent precursors include charged polymers that can form matrices such as gels, or precipitates, micelles or the like. This appropriately cancels out the electrostatic interaction so that the charged polymer becomes hydrophobicized, producing an adsorbent such as a matrix, such as a gel or precipitate, micelles or the like inside the vesicles, while also forming drug-carrying adsorbent-encapsulating vesicles having the drug trapped inside the adsorbent, such as the matrix, precipitate or micelles. Such drug carrying adsorbent-encapsulating vesicles are also useful as a sustained-release agent for sustained release of the drug.

[E] Poorly Water-Soluble Substance-Encapsulating Vesicles and their Production Method Yet another mode of the invention relates to a method of producing substance-encapsulating vesicles that allows production of vesicles encapsulating a poorly water-soluble substance (hereunder appropriately referred to as "poorly water-soluble substance-encapsulating vesicles"), and to novel poorly water-soluble substance-encapsulating vesicles produced by the method.

As a result of ardent research, the present inventors have found that it is possible to accomplish efficient encapsulation by preparing enzyme-encapsulating vesicles in which an enzyme that can convert a precursor with higher water solubility than a target substance to the target substance is encapsulated in vesicles, and the precursor is allowed to penetrate into enzyme-encapsulating vesicles for conversion to the target substance by the enzyme in the vesicles, precipitating the target substance and encapsulating it in the vesicles. This mode is based on the aforementioned finding.

The method of producing substance-encapsulating vesicles according to this mode is a method in which substance-encapsulating vesicles are produced having a target substance encapsulated in vesicles that comprise a membrane that includes a first polymer, which is a block copolymer having an uncharged hydrophilic segment and a first charged segment, and a second polymer which has a second charged segment having a charge opposite to the charge of the first charged segment, and the method includes the following steps.

(a) A step of preparing enzyme-encapsulating vesicles wherein an enzyme that can convert a precursor having higher water solubility than the target substance into the target substance, is encapsulated in vesicles comprising a membrane that includes the first and second polymers.

(b) A step of allowing the precursor to penetrate into the enzyme-encapsulating vesicles under conditions which produce lower solubility for the target substance than for the precursor, and converting the precursor into the target substance by the enzyme, to precipitate the target substance and encapsulate it in the enzyme-encapsulating vesicles, to produce poorly water-soluble substance-encapsulating vesicles.

The target substance to be encapsulated in the vesicles of this mode is a substance that can be converted from a highly water-soluble precursor by the enzyme. Any desired type of substance may be utilized as the target substance, so long as a precursor with high water solubility than the target substance exists and an enzyme exists that can produce conversion from the precursor to the target substance.

Stated differently, the target substance to be encapsulated in the vesicles according to this mode is a substance that has reduced solubility in water by enzyme action. In this case, the substance in a state with relatively high solubility in water before undergoing enzyme action is the precursor, and the substance in a state with relatively low solubility in water after undergoing enzyme action is the target substance. Thus, the combination of the precursor and the target substance may be not only combinations of substances with different chemical formulas and chemical compositions, but also substances having the same chemical formula or chemical composition, but with different solubilities in water with changes in spatial configuration or the like.

For this mode, the ratio of the solubility of the target substance with respect to the solubility of the precursor is preferably low. Specifically, though this is not limitative, when the solubilities in water at 25° C. are compared, the ratio of the solubility of the target substance with respect to the solubility of the precursor is usually preferred to be no greater than 90%, especially no greater than 80% and more especially no greater than 70%.

Also, the difference in the water solubilities of the precursor and the target substance is preferably large, although this will depend on the respective water solubilities of the precursor and target substance and on the purpose of use. Specifically, when the solubilities in water at 25° C. are compared, it may be preferred for the precursor to have solubility that is usually 10 mg/mL or more, especially 20 mg/mL or more and more especially 30 mg/mL or more higher than that of the target substance.

Furthermore, the target substance preferably has low water solubility. Specifically, the solubility in water at 25° C. is usually preferred to be no higher than 1.0 mg/mL, preferably no higher than 0.3 mg/mL and more preferably no higher than 0.1 mg/mL.

Various combinations are known for target substances and precursors according to this definition, as well as their combination with enzymes that mediate their conversion, and any may be used according to the invention. As an example, considering use of the produced vesicles as a DDS or the like, there may be mentioned various enzyme prodrugs and the like that are converted to active drugs by different enzymes.

For this mode, first there are prepared enzyme-encapsulating vesicles in which an enzyme is encapsulated in vesicles comprising a membrane that contains the first and second polymers. Such enzyme-encapsulating vesicles are prepared by encapsulating an enzyme in vesicles using any desired method such as one of the different methods of producing substance-encapsulating vesicles described above under [B] (post-loading method, simultaneous mixing method, etc.) or the method of producing substance-encapsulating vesicles described above under [C].

The precursor is then allowed to penetrate into the enzyme-encapsulating vesicles under conditions that produce lower solubility for the target substance than for the precursor. The method for allowing penetration of the precursor into the enzyme-encapsulating vesicles may be any desired method, but usually this is accomplished by mixing the enzyme-encapsulating vesicles and the precursor in a solvent. In this case, solutions containing the enzyme-encapsulating vesicles and precursor in different solvents are separately prepared, and thoroughly mixed, and either the enzyme-encapsulating vesicles or the precursor may be directly added to a solution containing the other in a solvent. The enzyme-encapsulating vesicles and precursors may also be contacted in a continuous phase such as a liquid (for example, use in vivo as described below falls under this case).

The conditions producing lower solubility for the target substance than for the precursor are preferably conditions that allow the precursor to generally exist in a dissolved state in the solvent, but wherein the target substance either partially or totally precipitates from the solvent. This can be achieved by selecting an appropriate solvent in consideration of the different water solubilities of the precursor and the target substance. For example, when the target substance is a substance with low water solubility according to the aforementioned definition and the precursor is the substance that is water-soluble according to the aforementioned definition, such conditions can be achieved by using a common aqueous medium. Also, the aforementioned conditions can be achieved by controlling the solubility of the solvent by dissolving various organic or inorganic electrolytes in the solvent, to adjust the solubility, or adjusting the various environmental factors such as temperature.

By allowing the precursor to penetrate into the enzyme-encapsulating vesicles under such conditions, the precursor is converted to the target substance by the enzyme. It is preferred to select appropriate conditions according to the combination of target substance/precursor/enzyme so that the conversion reaction from the precursor to the target substance by the enzyme proceeds in a satisfactory manner. As the precursor is converted to the target substance by the enzyme in this manner, the target substance precipitates from the solvent and is encapsulated in the enzyme-encapsulating vesicles, forming substance-encapsulating vesicles.

The other conditions for production may be the same conditions described above under [B], or those conditions with appropriate modifications.

In the production method for substance-encapsulating vesicles according to this mode, steps other than those described above may also be carried out in addition. An example is addition of a step of crosslinking the first and/or second polymer before and/or after allowing the precursor to penetrate into the enzyme-encapsulating vesicles. Particularly from the viewpoint of preventing loss of the enzyme from the enzyme-encapsulating vesicles and stabilizing the vesicles, crosslinking of the first and/or second polymer in the enzyme-encapsulating vesicles is preferably before penetration of the water-soluble precursor into the enzyme-encapsulating vesicles. By crosslinking the polymer it is possible to stably maintain the vesicles even under physiological conditions, when this mode is to be used as a DDS, for example. The method of crosslinking the first and/or second polymer may employ the same conditions described above under [C], or those conditions with appropriate modifications.

In the method of producing substance-encapsulating vesicles according to this mode, the enzyme-encapsulating vesicles that are used have an enzyme previously enclosed in the vesicles, so that the location where the target substance is produced is presumably limited only to the interiors of the vesicles, thereby allowing the target substance to be efficiently encapsulated in the vesicles. As a result, substances that normally can only be enclosed to a percentage corresponding to the number density in the solution can be encapsulated with very high encapsulation efficiency. In addition, by changing the amount of precursor added to the enzyme-encapsulating vesicles, it is possible to also control the amount of encapsulation of the target substance in the vesicles. Furthermore, it is believed that the target substance encapsulated in the vesicles can be released from the vesicles because the vesicles have the property of semipermeable membranes.

Moreover, in method of producing substance-encapsulating vesicles according to this mode it is possible to form vesicles that encapsulate even poorly water-soluble substances, that have conventionally been very difficult or impossible to encapsulate in vesicles. That is, according to this mode, poorly water-soluble substance-encapsulating vesicles are obtained having a poorly water-soluble substance (with an enzyme) encapsulated in vesicles comprising a membrane containing the first and second polymers. Such poorly water-soluble substance-encapsulating vesicles also conform to the gist of the present invention. In such vesicles, the poorly water-soluble substance is preferably encapsulated at a concentration exceeding the solubility of the poorly water-soluble substance in the inner aqueous phase. Also in such vesicles, preferably first and/or second polymers are crosslinked.

Furthermore, while formation of the substance-encapsulating vesicles by the production method of this mode can be accomplished artificially in vitro, the combination of target substance/precursor/enzyme can be appropriately selected to allow design so that the same is achieved in vivo. Such a mode will be described below.

[F] Other Modifications

Various modes of the invention were explained above, but the invention is not limited to these modes, and various modifications may be implemented as desired. For example, a monodisperse population of substance-encapsulating crosslinked vesicles as described above under <C-1>, multiple different substance-encapsulating crosslinked vesicles as described above under <C-2>, adsorbent-encapsulating crosslinked vesicles as described above under [D] or poorly water-soluble substance-encapsulating vesicles as described above under [E] may be used to carry a drug, for use as a pharmaceutical composition or in a drug delivery system. Such a pharmaceutical composition or drug delivery system containing various substance-encapsulating vesicles according to the invention also fall within the scope of the invention. The target to which such a pharmaceutical composition or drug delivery system is applied (which may be any living organism but is preferably an animal, more preferably a mammal, and yet more preferably a human), the disease and the drug, etc. may be selected as appropriate. Moreover, the various conditions such as the route of administration, indications, dosage, etc. for such a pharmaceutical composition or drug delivery system may also be appropriately selected according to the target, disease, drug and the like.

Furthermore, while formation of the substance-encapsulating vesicles by the production method described above under [E] can be accomplished artificially in vitro, the combination of target substance/precursor/enzyme can be appropriately selected to allow design so that the same is achieved in vivo. Specifically, a precursor that exhibits solubility (water solubility) in physiological solutions such as blood or body fluids is introduced into the body, the enzyme-encapsulating vesicles are separately introduced into the body, and the enzyme-encapsulating vesicles are contacted with the precursor at a desired site in the body to allow penetration of the precursor into the enzyme-encapsulating vesicles. Thus, the precursor may be converted to the target substance that exhibits low solubility (low water solubility) in physiological solutions to form substance-encapsulating vesicles containing the target substance in vivo. Here, if the combination of drug and its enzyme prodrug as described above is employed as the combination of target substance and precursor, the prodrug will be converted to the drug and encapsulated in the vesicles at the site of a desired organ or tissue in the body, and the drug will be released from the formed drug-encapsulating vesicles, thus allowing an excellent DDS to be obtained.

In addition, substance-encapsulating vesicles having an enzyme with action of converting a drug precursor (prodrug) to a drug, encapsulated as a substance to be encapsulated in substance-encapsulating crosslinked vesicles according to [C] above (enzyme-encapsulating crosslinked vesicles), or substance-encapsulating vesicles having the enzyme adsorbed and carried on an adsorbent in adsorbent-encapsulating vesicles according to [D] above (enzyme-carrying adsorbent-encapsulating vesicles), may be prepared and used. In this case, the prodrug is introduced into the body while the enzyme-encapsulating crosslinked vesicles or enzyme-carrying adsorbent-encapsulating vesicles are separately introduced into the body, and the enzyme-encapsulating crosslinked vesicles or enzyme-carrying adsorbent-encapsulating vesicles contact with the prodrug at the desired site in the body, allowing the prodrug to penetrate into the vesicles. By action of the enzyme on the prodrug in this manner for conversion to a drug, it is possible to produce a drug from the prodrug in the body.

This mode, incidentally, can be accomplished not only using various substance-encapsulating vesicles according to the invention, but even using any other desired substance-encapsulating vesicles. That is, any desired substance-encapsulating vesicles having an enzyme encapsulated and carried (enzyme-carrying vesicles) may be prepared for use. In this case, the prodrug is introduced into the body while the enzyme-carrying vesicles are separately introduced into the body, and the enzyme-carrying vesicles contact with the prodrug at the desired site in the body, allowing the prodrug to penetrate into the vesicles. By action of the enzyme on the prodrug in this manner for conversion to a drug, it is possible to produce a drug from the prodrug in the body.

According to these modes, there is no restriction on the relationship between the solubilities of the drug and prodrug, and any desired combination of drug/prodrug/enzyme may be used.

Specific examples of such drug/prodrug/enzyme combinations include those shown in the following table, but these are merely examples, and the drug/prodrug/enzyme combinations to be applied for the invention are not limited to these combinations.

TABLE 1

| Precursor (prodrug) | Target substance (drug) | Enzyme |
| --- | --- | --- |
| Irinotecan | SN-38 | Carboxyesterase |
| Amprenavir | Amprenavir | Alkali phosphatase |
| Fosphenytoin | Phenytoin | Alkali phosphatase |
| Fospropofol | Propofol | Alkali phosphatase |
| Chloramphenicol succinate | Chloramphenicol | Esterase |
| Valaciclovir | Aciclovir | Esterase |
| Dipivefrine | Adrenaline | Esterase |
| Risperidone | Paliperidone | CYP2D6 |
| 5-Fluorocytosine | 5-Fluorouracil | Cytosine deaminase |

That is, according to the invention there is further provided a method for delivery of a drug to a target, wherein the method includes the following steps.

(a) A step in which enzyme-encapsulating vesicles are prepared having an enzyme that can convert a drug precursor (prodrug) to a drug, encapsulated in vesicles that comprise a membrane comprising a first polymer, which is a block copolymer having an uncharged hydrophilic segment and a first charged segment, and a second polymer which has a second charged segment having a charge opposite to the charge of the first charged segment.

(b) A step in which the precursor is allowed to penetrate into the enzyme-encapsulating vesicles at a prescribed target site, for conversion of the precursor into the drug by the enzyme, to form the drug.

Step (b) of this method is accomplished by causing the enzyme-encapsulating vesicles and the precursor to be copresent at the prescribed target site. The prescribed target site may be any desired one and may be determined according to the target of drug delivery, the type of drug, the disease to be treated, etc., but usually it will be a prescribed target organ, tissue or cells. The method for causing the enzyme-encapsulating vesicles to be copresent at the prescribed target site may also be as desired, but usually the enzyme-encapsulating vesicles may be administered by any of various publicly known methods of administration so that they reach the prescribed target site. The method of administration may be oral or parenteral, and for parenteral administration, the route of administration may be intravenous, intramuscular, subcutaneous, transdermal, nasal, transpulmonary, or the like.

In step (b) of this method, a precursor can be converted to a drug by an enzyme that is encapsulated in enzyme-encapsulating vesicles. This allows the converted drug to be released from the vesicles and be delivered the prescribed target site. From the viewpoint of allowing the drug to be stably delivered for prolonged periods, however, preferably the drug precipitates so as to become encapsulated in the enzyme-encapsulating vesicles, forming drug-encapsulating vesicles.

The other conditions such as dosage and indications may be determined as appropriate according to the target of drug delivery, the type of drug, the disease to be treated, etc.

Furthermore, the drug delivery system and pharmaceutical composition used in the method described above (including the enzyme-encapsulating vesicles) also fall within the scope of the invention.

EXAMPLES

The present invention will now be explained in greater detail with reference to examples. The examples that follow are only for illustrative purposes and do not limit the present invention in any way.

The terms "solution" and "dispersion" used throughout the following explanation, unless otherwise specified, indicate a "solution" or "dispersion" using 10 mM phosphate buffer (pH 7.4) as the solvent or dispersing medium.

Also, the "vortex mixer" used in the following explanation was an Eppendorf MixMate, unless otherwise specified.

The "mean particle size", the "polydispersity index" (PDI) and the "zeta potential" in the following explanation were measured with a Zetasizer Nano-ZS manufactured by Malvern, unless otherwise specified.

Also, the "transmission electron microscope images" referred to in the following explanation were taken using a JEM-1400 by JEOL Corp., unless otherwise specified.

[Example Group I] Substance-Encapsulating Vesicles and their Production Method

[Example I-1] Enclosure of FITC-Dex40k into Vacant Crosslinked Vesicles (1) Preparation of Vacant Vesicles As the first polymer there was used the anionic block copolymer PEG-P(Asp), comprising polyethylene glycol (weight-average molecular weight: approximately 2000) (hereunder also referred to as "PEG") as an uncharged hydrophilic segment and polyaspartic acid (polymerization degree: approximately 75) as an anionic segment. Some of the polyaspartic acid N-terminals were fluorescently labeled with Cy3.

As the second polymer there was used the cationic homopolymer Homo-P(Asp-AP), comprising a poly(diaminopentane structure-containing asparagine derivative) (polymerization degree: approximately 82) (hereunder also referred to as "P(Asp-AP)").

The first and second polymers were each dissolved in a 10 mM phosphate buffer (pH 7.4) (aqueous medium) to a polymer concentration of 1.0 mg/mL. The obtained first polymer solution and second polymer solution were placed in an Eppendorf tube to an equal charge ratio (i.e. a C/A ratio of 1.0) and mixed, and the mixture was then stirred using a vortex mixer at 2000 rpm for 2 minutes to obtain a solution containing the vesicles (vacant vesicles) formed by self-assembly of the first and second polymers.

The obtained vacant vesicle-containing solution was measured by dynamic light scattering to determine the particle size distribution, mean particle size and polydispersity index (PDI). As a result, it was confirmed that the formed monodisperse vesicle particles had a mean particle size of 101.4 nm and a PDI of 0.070.

(2) Crosslinking of Vacant Vesicles

A 0.5 mL portion of the obtained vacant vesicle-containing solution was added to a solution containing EDC (product of Dojindo Laboratories) at 0.5 equivalent with respect to the carboxyl groups in the PEG-P(Asp) (in 10 mM phosphate buffer (0 mM NaCl) at pH 7.4), and the mixture was allowed to stand at room temperature for 12 hours, for crosslinking of the vacant vesicles to obtain a vacant crosslinked vesicle-containing solution.

(3) Enclosure of FITC-Dex40k into Vacant Crosslinked Vesicles

As the substance to be encapsulated there was used fluorescein isothiocyanate-dextran (product of Sigma-Aldrich, hereunder also referred to as "FITC-Dex40k") (weight-average molecular weight: 40,000).

To 0.5 mL of the obtained vacant crosslinked vesicle-containing solution there was added FITC-Dex40k solution (in an amount for a post-mixing FITC-Dex40k concentration or 5 to 50 mg/mL and a charged polymer (first and second polymer) concentration of 1.0 mg/mL), and a vortex mixer was used for stirring at 2000 rpm for 2 minutes to enclose the FITC-Dex40k into the vacant crosslinked vesicles and obtain an FITC-Dex40k-encapsulating crosslinked vesicle-containing solution. The obtained solution was transparent.

To 1.0 mL of solution obtained by mixing under sufficient external force application conditions (stirring at 2000 rpm for 2 minutes), there was added a solution containing EDC at 10 equivalents with respect to the carboxyl groups in the PEG-P(Asp) (in 10 mM phosphate buffer (0 mM NaCl) at pH 7.4), and the mixture was allowed to stand at room temperature for 12 hours for sufficient crosslinking of FITC-Dex40k-encapsulating crosslinked vesicles.

FITC-Dex40k remaining in the free state in the solution without being encapsulated in the vesicles was removed by centrifugal ultrafiltration (VIVASPIN 20, product of Sartorius Stedium Biotech, using a molecular cutoff of 300,000) (centrifugal ultrafiltration conditions: 300 rpm, 4° C.) for purification, after which measurement was performed by dynamic light scattering to determine the particle size distribution, mean particle size and polydispersity index (PDI). As a result, the particle size distribution, mean particle size and polydispersity index (PDI) of the FITC-Dex40k-encapsulating crosslinked vesicles were virtually unchanged from the vacant vesicles, confirming that FITC-Dex40k had been enclosed in the vacant vesicles while maintaining the monodisperse property. For example, the mean particle size of the FITC-Dex40k-encapsulating crosslinked vesicles obtained by stirring and mixing a 50 mg/mL FITC-Dex40k solution was 97.2 nm and the PDI was 0.087 (the mean particle size of the vacant vesicles was 101.4 nm and the PDI was 0.070); the transmission electron microscope (TEM) image was as shown in FIG. 5A.

Fluorescence correlation spectroscopy (FCS) measurement was then performed at room temperature using a confocal fluorescent microscope (LSM510) manufactured by Carl Zeiss. Fluorescent dextran was excited by an argon laser (488 nm), the objective lens used being a water immersion lens with a 40-fold magnification, and analysis was performed with Confocor 3 software to determine the autocorrelation function $G(\tau)$. The number of FITC-Dex40k molecules per FITC-Dex40k-encapsulating vesicle was estimated from the $G(\tau)$ value. The autocorrelation function $G(\tau)$ is a function for evaluating the fluctuation in fluorescent intensity after time $\tau$, and it attenuates with time and converges after elapse of a sufficient time. The longer the time until convergence (slower attenuation), the more gradual the fluctuation is, in other words, the slower the movement of the fluorescent object being measured. Also, since the fluctuation is reduced with a greater number of molecules in the observation field, it is possible to estimate the number of molecules from the value of the correlation function.

The numbers of FITC-Dex40k molecules per FITC-Dex40k-encapsulating vesicle are shown in Table 2.

As shown in Table 2, the number of FITC-Dex40k molecules per FITC-Dex40k-encapsulating vesicle increased as the concentration of the FITC-Dex40k solution mixed with the vacant crosslinked vesicles increased.

TABLE 2

| | | FITC-Dex40k solution concentration | | | |
|---|---|---|---|---|---|
| | | 5 mg/mL | 10 mg/mL | 20 mg/mL | 50 mg/mL |
| FITC-Dex40k count | Example I-1 | 12.4 ± 1.8 | 20.0 ± 2.5 | 30.1 ± 5.6 | 29.9 ± 3.2 |
| | Comp. Example I-1 | 4.8 ± 1.9 | — | — | — |
| | Comp. Example I-2 | 5.2 ± 1.2 | — | — | — |

These results demonstrated that by mixing a monodisperse population of vacant vesicles, after their crosslinking, in an FITC-Dex40k solution under conditions with sufficient external force application, a monodisperse population of FITC-Dex40k-encapsulating vesicles is produced which have FITC-Dex40k enclosed in the vacant vesicles while maintaining their monodisperse property.

Furthermore, comparison between Example I-1 and Comparative Examples I-1 and I-2 (below) demonstrated that, only in Example I-1, a monodisperse population of FITC-Dex40k-encapsulating vesicles is formed even if the FITC-Dex40k concentration in the aqueous medium exceeded 5 mg/mL.

[Comparative Example I-1] Enclosure of FITC-Dex40k by Simultaneous Mixing Method Similar to Example I-1, the first and second polymers were each dissolved in a 10 mM phosphate buffer (pH 7.4) (aqueous medium) to a polymer concentration of 2.0 mg/mL. At that time, the prescribed FITC-Dex40k was added to the first polymer to a final concentration of FITC-Dex40k of 5 to 50 mg/mL and a final concentration of charged polymers (first and second polymers) of 1.0 mg/mL, after mixing with the solution of the second polymer.

The obtained first polymer/FITC-Dex40k mixed solution and second polymer solution were placed in an Eppendorf tube to an equal charge ratio of the first polymer and second polymer (i.e. a C/A ratio of 1.0) and mixed, and the mixture was then stirred using a vortex mixer at 2000 rpm for 2 minutes to obtain a solution containing the self-assembly aggregates of the first and second polymers.

To 0.5 mL of the obtained solution there was added a solution containing EDC at 10 equivalents with respect to the carboxyl groups in the PEG-P(Asp) (in 10 mM phosphate buffer (0 mM NaCl) at pH 7.4), and the mixture was allowed to stand at room temperature for 12 hours. The FITC-Dex40k remaining in a free state in the solution was removed by centrifugal ultrafiltration similar to Example I-1, and the obtained self-assembly aggregates were evaluated by DLS and TEM.

Figure 5B:
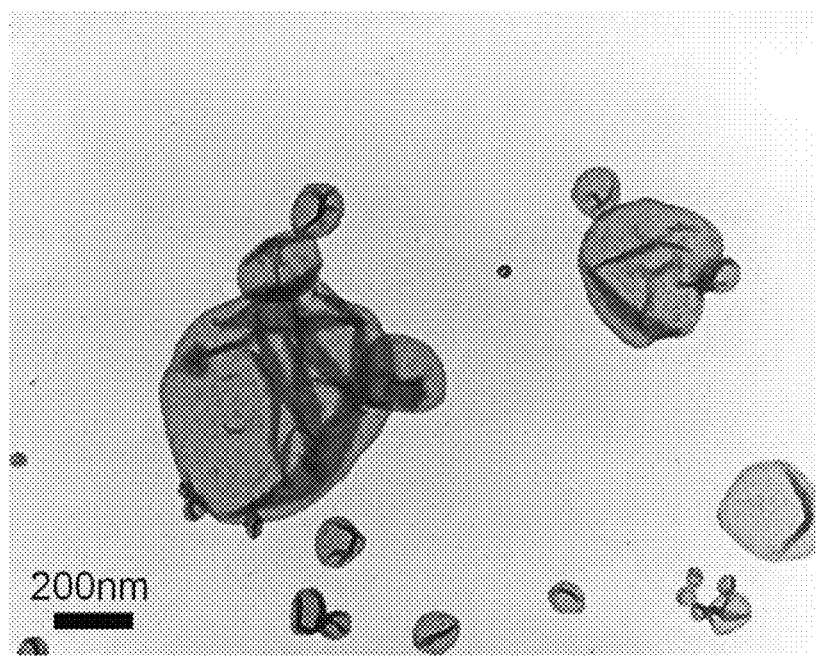
FIG. 5B is a transmission electron microscopic (TEM) image of the non-crosslinked vesicles encapsulating FITC-Dex40k obtained in Comparative Example I-1 (simultaneous mixing method).

As shown in FIG. 5B, the self-assembly aggregates obtained with an FITC-Dex40k final concentration of 50 mg/mL were unilamellar vesicles, but a notable tendency toward increased particle size was observed. The results of DLS also showed an increase in size, loss of unimodality and marked increase in PDI (mean particle size: approximately 630 nm, PDI: approximately 0.62). This suggests that the vesicle-forming process (especially the state of stirring and mixing) was affected by the solution viscosity, thereby producing a wide particle size distribution. On the other hand, with self-assembly aggregates obtained when the final concentration of FITC-Dex40k was 5 mg/mL, monodisperse vesicle particles with particle sizes of about 100 nm were formed, allowing estimation of FITC-Dex40k enclosure by FCS (Table 2).

[Comparative Example I-2] Enclosure of FITC-Dex40k by Post-Loading Method

Similar to Example I-1, the first and second polymers were each dissolved in a 10 mM phosphate buffer (pH 7.4) (aqueous medium) to a polymer concentration of 1.0 mg/mL. The obtained first polymer solution and second polymer solution were placed in an Eppendorf tube to an equal charge ratio of the first polymer and second polymer (i.e. a C/A ratio of 1.0) and mixed, and the mixture was then stirred using a vortex mixer at 2000 rpm for 2 minutes to obtain a solution containing the self-assembly aggregates of the first and second polymers. Based on the results of DLS, the mean particle size was 101.8 nm and the PDI was 0.081.

To 0.5 mL of the obtained solution there was added a prescribed FITC-Dex40k solution for a post-mixing final FITC-Dex40k concentration of 5 to 50 mg/mL and a charged polymer (first and second polymer) concentration of 1.0 mg/mL, and a vortex mixer was again used for stirring at 2000 rpm for 2 minutes. Next, there was added a solution containing EDC at 10 equivalents with respect to the carboxyl groups in the PEG-P(Asp) (in 10 mM phosphate buffer (0 mM NaCl) at pH 7.4), and the mixture was allowed to stand at room temperature for 12 hours. The dextran remaining in a free state in the solution was removed by centrifugal ultrafiltration similar to Example I-1, and the obtained self-assembly aggregates were evaluated by DLS and TEM.

Figure 5C:
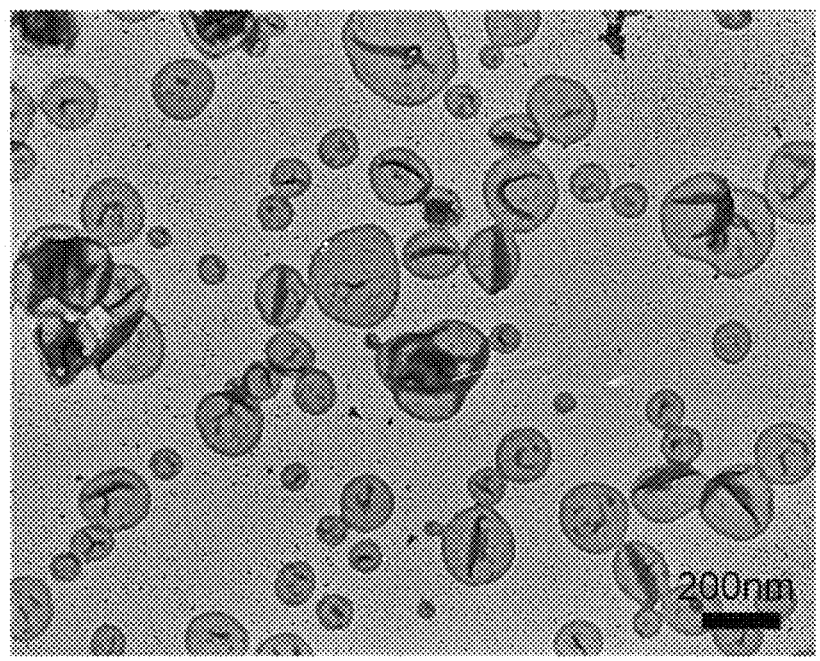
FIG. 5C is a transmission electron microscopic (TEM) image of the non-crosslinked vesicles encapsulating FITC-Dex40k obtained in Comparative Example I-2 (post-carrying method).

As shown in FIG. 5C, the self-assembly aggregates obtained with an FITC-Dex40k final concentration of 50 mg/mL were unilamellar vesicles, but a notable tendency toward increased particle size was observed. The results of DLS also showed an increase in size, loss of unimodality and marked increase in PDI (mean particle size: approximately 560 nm, PDI: approximately 0.57). On the other hand, with self-assembly aggregates obtained when the final concentration of FITC-Dex40k was 5 mg/mL, monodisperse vesicle particles with particle sizes of about 100 nm were formed, allowing estimation of enclosure by FCS (Table 2).

[Reference Example I-1] FITC-Dex40k Release from FITC-Dex40k-Encapsulating Vesicles Similar to Example I-1, the first and second polymers were each dissolved in a 10 mM phosphate buffer (pH 7.4) (aqueous medium) to a polymer concentration of 1.0 mg/mL. The obtained first polymer solution and second polymer solution were placed in an Eppendorf tube to an equal charge ratio of the first polymer and second polymer (i.e. a C/A ratio of 1.0) and mixed, and the mixture was then stirred using a vortex mixer at 2000 rpm for 2 minutes to obtain a solution containing the self-assembly aggregates of the first and second polymers.

To 0.5 mL of the obtained solution there was added prescribed FITC-Dex40k for a post-mixing final FITC-Dex40k concentration of 4 mg/mL and a charged polymer (first and second polymer) concentration of 1.0 mg/mL, and stirring was again performed with a vortex mixer at 2000 rpm for 2 minutes. Next, there was added a solution containing EDC at 10 equivalents (in 10 mM phosphate buffer (0 mM NaCl) at pH 7.4), and the mixture was allowed to stand at room temperature for 12 hours. The dextran remaining in a free state in the solution without being encapsulated in the vesicles was removed by centrifugal ultrafiltration in the same manner as Example I-1. The purified FITC-Dex40k-encapsulating vesicles were allowed to stand under conditions of 37° C., 150 mM NaCl.

Figure 6:
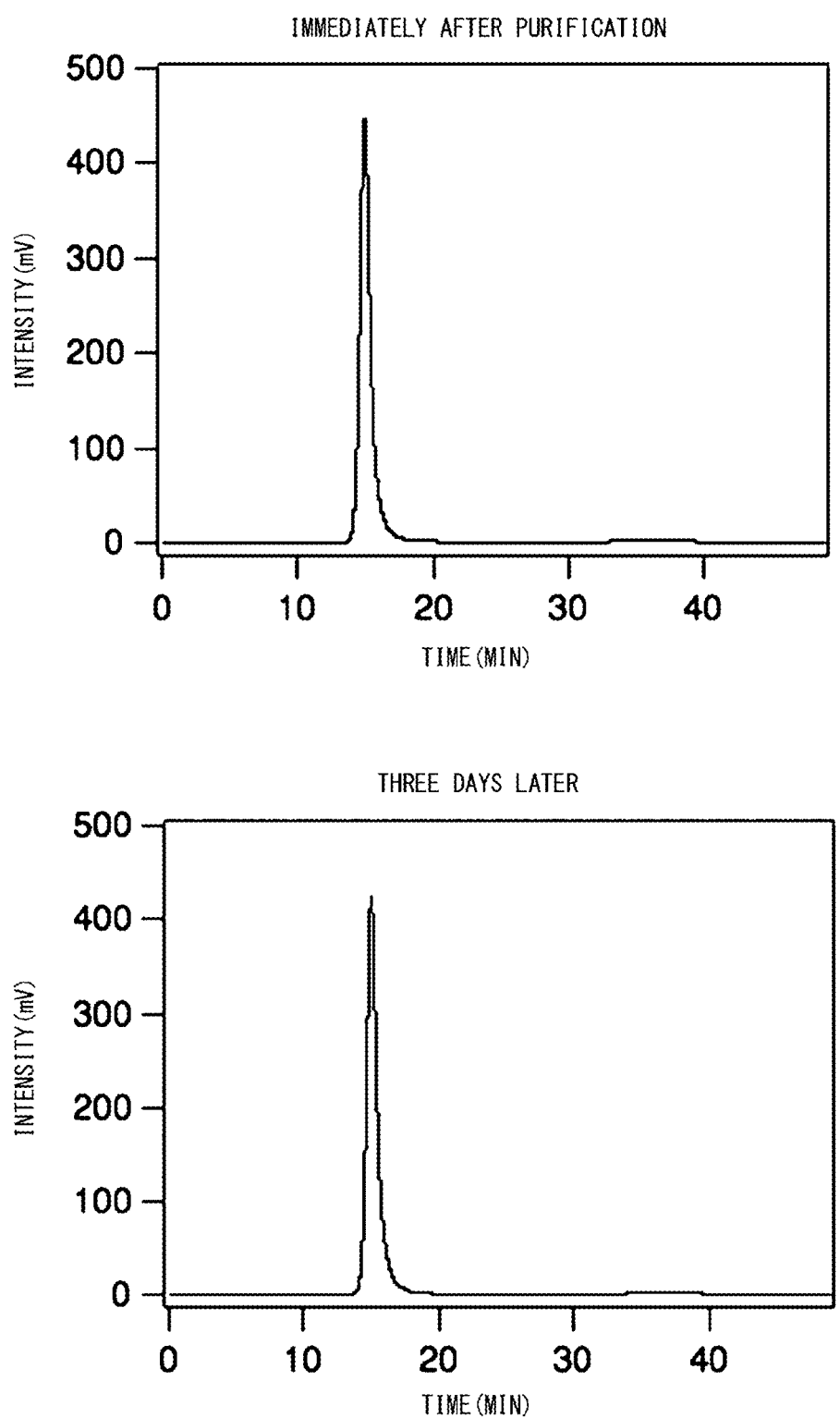
FIG. 6 is a graph showing the measurement results by gel permeation chromatography (GPC) carried out in order to confirm the release profile of FITC-Dex40k encapsulated in the vesicles.

The release behavior of the FITC-Dex40k enclosed inside the vesicles was confirmed using GPC (gel permeation chromatograph, product of JASCO Corp.). As shown in FIG. 6, no significant difference was seen in the chromatograms, immediately after purification and 3 days thereafter, and no release of FITC-Dex40k was confirmed. This result suggests that when external force is not applied by mixing or the like, transfer of FITC-Dex40k into and out of the vesicles does not take place.

[Reference Example I-2] Relationship Between FITC-Dex Concentration and Viscosity Since it was suggested in Comparative Example I-1 that the vesicle-forming process (especially the state of stirring and mixing) is affected by the solution viscosity, the relationship between the concentration and viscosity of FITC-Dex (weight-average molecular weights: 4000, 10,000, 40,000) was examined.

The viscosity was measured using a rotating rheometer (Physica MCR302, product of Anton Paar).

The measurement results for the viscosity (Pa·s) are shown in Table 3.

TABLE 3

| | | Weight-average molecular weight | | |
|---|---|---|---|---|
| | | 4000 | 10000 | 40000 |
| Concentration | 1 mg/mL | N.D. | N.D. | N.D. |
| | 4 mg/mL | N.D. | 0.0504 | 0.0513 |
| | 10 mg/mL | 0.0097 | 0.1271 | 0.1377 |
| | 50 mg/mL | — | — | 0.5481 |

[Example I-2] Enclosure of FITC-Dex4k into Cytochrome c-Encapsulating Crosslinked Vesicles (1) Preparation of Cytochrome c-Encapsulating Crosslinked Vesicles Cytochrome c (product of Sigma-Aldrich, molecular weight: 12,327 Da) was enclosed into vacant vesicles in the same manner as Comparative Example I-2. The specific method was as follows.

The first and second polymers were each dissolved in a 10 mM phosphate buffer (pH 7.4) (aqueous medium) to a polymer concentration of 2.0 mg/mL. The obtained first polymer solution and second polymer solution were placed in an Eppendorf tube to an equal charge ratio of the first polymer and second polymer (i.e. a C/A ratio of 1.0) and mixed, and the mixture was then stirred using a vortex mixer at 2000 rpm for 2 minutes to obtain a solution containing the vesicles (vacant vesicles) formed by self-assembly of the first and second polymers. Based on the results of DLS, the mean particle size was 102 nm and the PDI was 0.045.

To 0.96 mL of the obtained vacant vesicle-containing solution there was added 0.5 mL of a 1 mg/mL cytochrome c solution, and a vortex mixer was again used for stirring at 2000 rpm for 2 minutes, to obtain a cytochrome c-encapsulating vesicle-containing solution.

To 0.5 mL of the obtained cytochrome c-encapsulating vesicle-containing solution there was added a solution containing EDC at 0.5 equivalent with respect to the carboxyl groups in the PEG-P(Asp) (in 10 mM phosphate buffer (0 mM NaCl) at pH 7.4), and the mixture was allowed to stand at room temperature for 12 hours, for crosslinking of the cytochrome c-encapsulating vesicles to obtain a cytochrome c-encapsulating crosslinked vesicle-containing solution.

The cytochrome c remaining in a free state in the solution without encapsulation in the vesicles was removed by centrifugal ultrafiltration (molecular cutoff: 300,000) in the same manner as Example I-1, for purification of the vesicles. At that time, the mean particle size was 99.5 nm and the PDI was 0.032. GPC measurement confirmed that cytochrome c (absorption maximum: 409 nm wavelength) was enclosed in the vesicles (FIG. 7). In FIG. 7, (a) shows the GPC measurement results for the vacant vesicles, and (b) shows the GPC measurement results for the cytochrome c-encapsulating crosslinked vesicles after purification.

(2) Enclosure of FITC-Dex4k into Cytochrome c-Encapsulating Crosslinked Vesicles To 0.5 mL of the obtained cytochrome c-encapsulating crosslinked vesicle-containing solution there was added FITC-Dex4k solution (weight-average molecular weight: 4000, concentration: 50 mg/mL, volume: 0.5 mL), and a vortex mixer was used for stirring at 2000 rpm for 2 minutes to enclose the FITC-Dex4k into the cytochrome c-encapsulating crosslinked vesicles and obtain a cytochrome c- and FITC-Dex4k-encapsulating crosslinked vesicle-containing solution.

To the cytochrome c- and FITC-Dex4k-encapsulating crosslinked vesicle-containing solution there was added a solution containing EDC at 10 equivalents with respect to the carboxyl groups in the PEG-P(Asp) (in 10 mM phosphate buffer (0 mM NaCl) at pH 7.4), and the mixture was allowed to stand at room temperature for 12 hours, for sufficient crosslinking of the cytochrome c- and FITC-Dex4k-encapsulating crosslinked vesicles.

Figure 8:
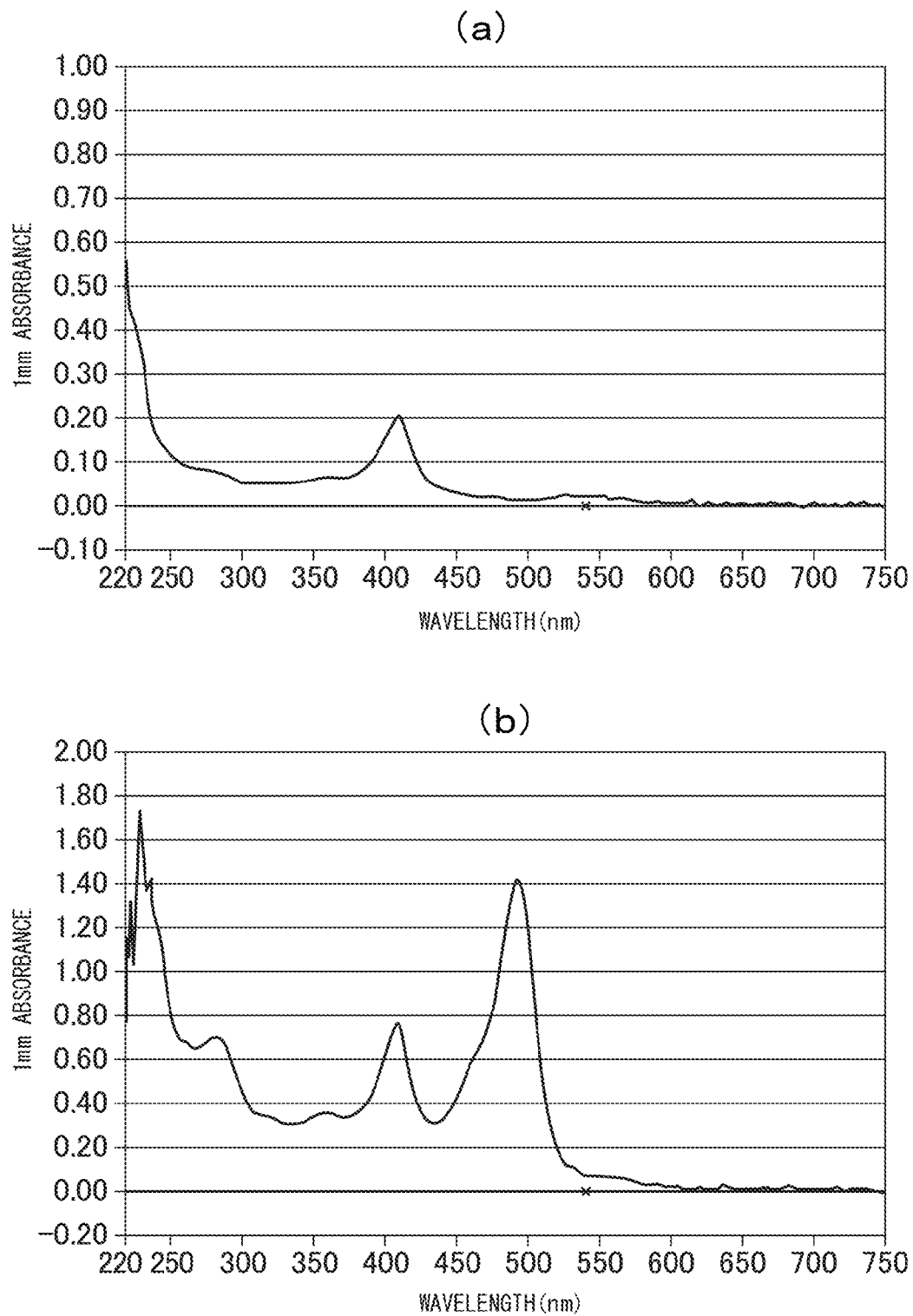
FIG. 8 (a) is an absorption spectrum of the crosslinked vesicles encapsulating cytochrome c obtained in Example I-2, (b) is an absorption spectrum of the crosslinked vesicles encapsulating cytochrome c and FITC-Dex40k obtained in Example I-2.

The FITC-Dex4k remaining in a free state in the solution without being encapsulated in the vesicles was removed by centrifugal ultrafiltration in the same manner as Example I-1. Based on the results of DLS measurement, the mean particle size was 101 nm and the PDI was 0.078. By the absorption spectrum of the obtained vesicles, it was confirmed that when cytochrome c and FITC-Dex4k were enclosed in the vesicles, i.e. when FITC-Dex4k was enclosed in cytochrome c-encapsulating crosslinked vesicles, the FITC-Dex4k was enclosed without release of the cytochrome c (FIG. 8). In FIG. 8, (a) shows the absorption spectrum for cytochrome c-encapsulating crosslinked vesicles, and (b) shows the absorption spectrum for cytochrome c- and FITC-Dex4k-encapsulating crosslinked vesicles.

The concentration of the FITC-Dex4k solution was changed to 1 to 100 mg/mL, cytochrome c- and FITC-Dex4k-encapsulating crosslinked vesicles were prepared in the same manner as above, FCS measurement was performed in the same manner as Example I-1, and the number of FITC-Dex4k molecules per vesicle was estimated. The results are shown in Table 4. As shown in Table 4, the number of FITC-Dex4k molecules per vesicle increased as the concentration of the FITC-Dex4k solution increased.

TABLE 4

| | FITC-Dex4k solution concentration | | | |
|---|---|---|---|---|
| | 1 mg/mL | 10 mg/mL | 50 mg/mL | 100 mg/mL |
| FITC-Dex4k count | 1.5 ± 1.1 | 5.9 ± 2.5 | 17.2 ± 6.1 | 16.8 ± 2.8 |

Figure 9:
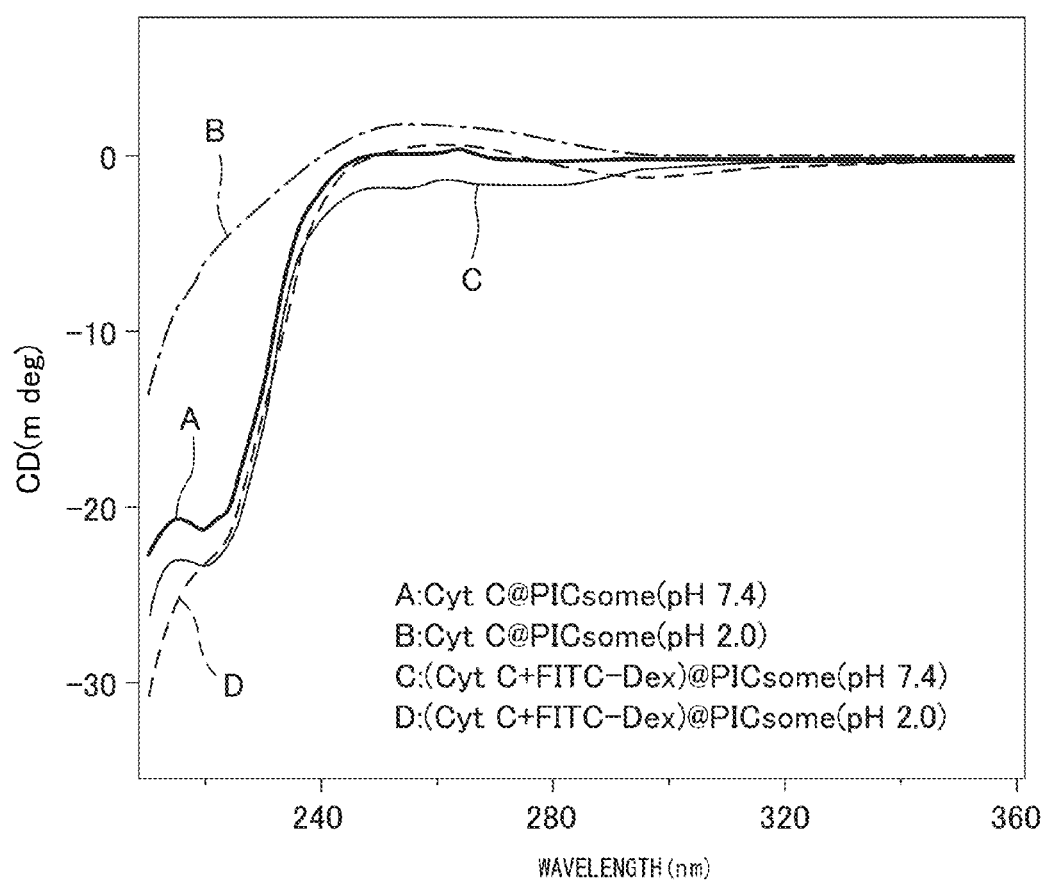
FIG. 9 is a graph showing the measurement results of circular dichroism spectrums.

Next, the spatial configuration stability of cytochrome c in an acidic environment was evaluated based on the circular dichroism spectrum, using a published reference [K. Sasahara, et al. J. Mol. Biol. (2003) 326, 1227-1237]. According to this reference, the spatial configuration of cytochrome c is lost from pH 2.0, as it loses its characteristic α-helix structure. However, loss of the structure can be prevented in the presence of a high concentration of dextran. Based on the circular dichroism spectrum (FIG. 9), when Dex was not copresent in the vesicles, absorption near 222 nm was lost when the pH fell to 2.0, whereas when Dex was copresent in the vesicles, no significant change was observed. This result suggests that a molecular crowding environment with Dex copresent at a high concentration had been created in the vesicles. In FIG. 9, "(A) Cyt C@PICsome (pH 7.4)" denotes the circular dichroism spectrum of cytochrome c-encapsulating crosslinked vesicles at pH 7.4, "(B) Cyt C@PICsome (pH 2.0)" denotes the circular dichroism spectrum of cytochrome c-encapsulating crosslinked vesicles at pH 2.0, "(C) (Cyt C+FITC-Dex)@PICsome (pH 7.4)" denotes the circular dichroism spectrum of cytochrome c- and FITC-Dex4k-encapsulating crosslinked vesicles at pH 7.4, and "(D) (Cyt C+FITC-Dex)@PICsome (pH 7.4)" denotes the circular dichroism spectrum of cytochrome c- and FITC-Dex4k-encapsulating crosslinked vesicles at pH 7.4.

[Example I-3] Enclosure of AlPcS2a into Vacant Crosslinked Vesicles

To vacant vesicles prepared in the same manner as Example I-1 there was added EDC at 1.0 equivalent with respect to the carboxyl groups in the PEG-P(Asp), to produce vacant crosslinked vesicles. At that time, the mean particle size was 101 nm and the PDI was 0.084. A dispersion of sulfonated phthalocyanine (AlPcS2a) (product of Frontier Scientific) was prepared to different concentrations (0, 1, 2, 10, 20 and 50 mg/mL), and was mixed with the vacant crosslinked vesicles to a vesicle concentration of 1 mg/mL, and then subjected to ultrasonic irradiation for 2 minutes. The vesicle concentration was quantified by the fluorescent label Cy3.

AlPcS2a is a drug (photosensitizer) utilized in photodynamic therapy, and it has the following structure.

[Chemical Formula 10]

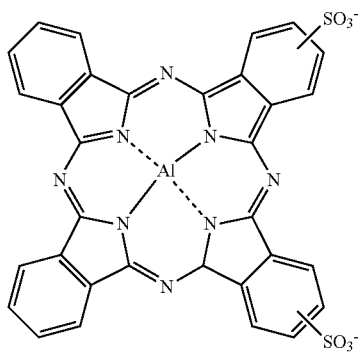

Following ultrasonic treatment, purification was performed with a PD-10 column (product of GE Healthcare) and centrifugal ultrafiltration (VIVASPIN20, product of Sartorius Stedium Biotech, using molecular cutoff of 300,000), to remove the AlPcS2a remaining in a free state in the solution. According to DLS measurement, the purified vesicles maintained both their particle sizes and monodisperse property, with a mean particle size of about 110 nm and a PDI of about 0.05 to 0.08, regardless of the AlPcS2a concentration. Also, the purified vesicles were subjected to a color test based on the absorption color of AlPcS2a. As shown in FIG. 10(A), the AlPcS2a-attributed blue was stronger with increasing contacting AlPcS2a concentration.

Comparative Example I-3

Similar to Comparative Example I-2, the first and second polymers were each dissolved in a 10 mM phosphate buffer (pH 7.4) (aqueous medium) to a polymer concentration of 2.0 mg/mL. The obtained first polymer solution and second polymer solution were placed in an Eppendorf tube to an equal charge ratio of the first polymer and second polymer (i.e. a C/A ratio of 1.0) and mixed, and the mixture was then stirred using a vortex mixer at 2000 rpm for 2 minutes to obtain a solution containing the self-assembly aggregates of the first and second polymers. To 0.5 mL of the obtained solution there was added prescribed AlPcS2a solution for a post-mixing AlPcS2a concentration of 2.0 mg/mL and a charged polymer concentration of 1.0 mg/mL, and stirring was again performed with a vortex mixer at 2000 rpm for 2 minutes. Next, there was added a solution containing EDC at 10 equivalents with respect to the carboxyl groups in the PEG-P(Asp) (in 10 mM phosphate buffer (0 mM NaCl) at pH 7.4), and the mixture was allowed to stand at room temperature for 12 hours. The AlPcS2a remaining in a free state in the solution without being encapsulated in the vesicles was removed by centrifugal ultrafiltration in the same manner as Example I-1. Based on the results of DLS measurement, the mean particle size was 104 nm and the PDI was 0.062. When the amount of AlPcS2a enclosed was compared with the results of Example I-3 based on the color test shown in FIG. 10(A), it was found that Example I-3 had a greater amount enclosed, even with the same concentration of AlPcS2a contacted. Furthermore, it was difficult to maintain the particle size and PDI when the post-mixing AlPcS2a concentration was greater than 2.0 mg/mL.

Figure 10B:
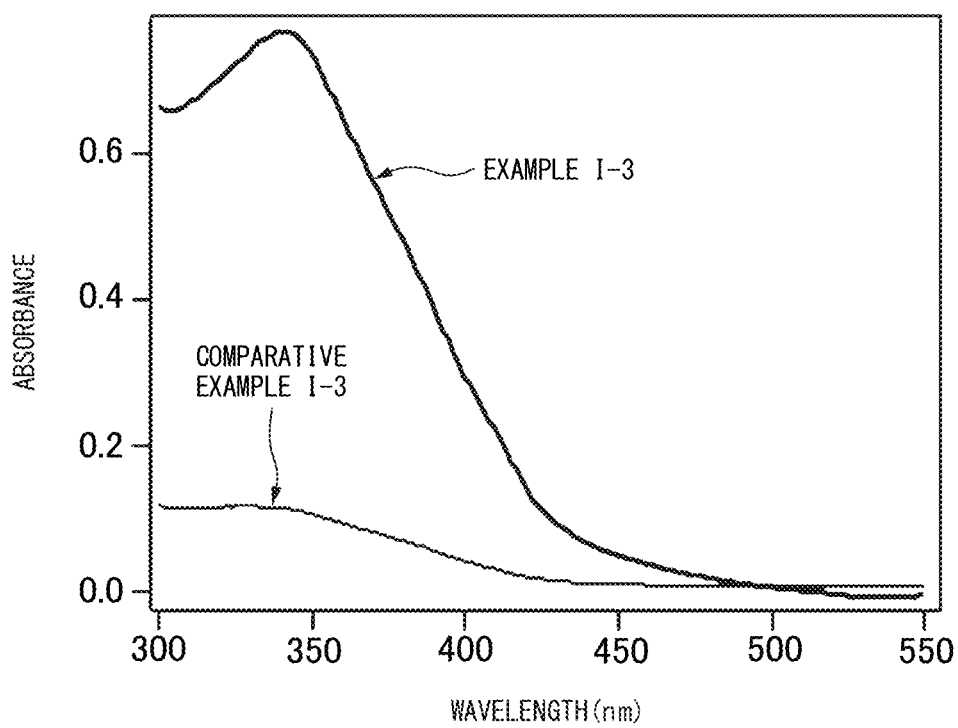
FIG. 10(B) is a graph showing adsorbance spectrums of the vesicles obtained in Example I-3 and Comparative Example I-3.

Also, the vesicle solutions of Example I-3 and Comparative Example I-3 (both with AlPcS2a concentrations of 20 mg/mL) were each diluted to a charged polymer concentration of 0.5 mg/mL and the absorption spectra were measured with a spectrophotometer. The results are shown in FIG. 10(B). As expected, it was found that Example I-3 had a greater amount enclosed than Comparative Example I-3, even with the same concentration of AlPcS2a contacted.

[Reference Example I-3] Effect of NaCl Concentration on Vacant Vesicles

As the first polymer there was used the anionic block copolymer PEG-P(Asp), comprising polyethylene glycol (weight-average molecular weight: approximately 2300) (hereunder also referred to as "PEG") as an uncharged hydrophilic segment and polyaspartic acid (polymerization degree: approximately 79) as an anionic segment. As the second polymer there was used the cationic homopolymer Homo-P(Asp-AP), comprising a poly(diaminopentane structure-containing asparagine derivative) (polymerization degree: approximately 71) (hereunder also referred to as "P(Asp-AP)"). The first and second polymers were each dissolved in a 10 mM phosphate buffer (pH 7.4; aqueous medium) to a polymer concentration of 1.0 mg/mL. A 35.5 µL portion of the obtained first polymer solution and a 50 µL portion of the second polymer solution were placed in an Eppendorf tube to an equal charge ratio (i.e. a C/A ratio of 1.0) and mixed, and the mixture was then stirred using a vortex mixer at 2000 rpm for 2 minutes to obtain a solution containing the vesicles (vacant vesicles) formed by self-assembly of the first and second polymers. To this there was added 10 mM phosphate buffer (pH 7.4) containing NaCl in prescribed amounts for final concentrations of 5, 10, 20 and 150 mM, and each was allowed to stand overnight.

Each obtained vacant vesicle-containing solution was measured by dynamic light scattering to determine the particle size distribution, mean particle size, polydispersity index (PDI) and zeta potential. The vacant vesicles having a mean particle size of 126 nm and a PDI of 0.049 before the NaCl addition exhibited the respective values shown in Table 5 after NaCl addition. In particular, a large value of about 0.2 was exhibited for the PDI in the presence of 20 mM NaCl, and even in the TEM image there was seen formation of polydisperse vesicles including numerous components with particle sizes exceeding 200 nm diameters (FIG. 11). Also, when 150 mM NaCl was added, the vacant vesicle solution immediately became opaque, suggesting increased sizes and polydispersity.

TABLE 5

| NaCl concentration (mM) | Particle size (nm) | | PDI | |
| --- | --- | --- | --- | --- |
| | Before NaCl addition | After NaCl addition | Before NaCl addition | After NaCl addition |
| 5 | 126 | 135 | 0.049 | 0.059 |
| 10 | 126 | 148 | 0.049 | 0.076 |
| 20 | 126 | 215 | 0.049 | 0.195 |

Next, as the first polymer there was used the anionic block copolymer PEG-P(Asp), comprising polyethylene glycol (weight-average molecular weight: approximately 2300) (hereunder also referred to as "PEG") as an uncharged hydrophilic segment and polyaspartic acid (polymerization degree: approximately 79) as an anionic segment. As the second polymer there was used the cationic homopolymer Homo-P(Asp-AP), comprising a poly(diaminopentane structure-containing asparagine derivative) (polymerization degree: approximately 71) (hereunder also referred to as "P(Asp-AP)"). The first and second polymers were each dissolved in a 10 mM phosphate buffer (pH 7.4; 3 different types prepared: NaCl-free and 10 and 20 mM NaCl; aqueous medium) to a polymer concentration of 1.0 mg/mL. The obtained first polymer solution and second polymer solution were placed in an Eppendorf tube to an equal charge ratio (i.e. a C/A ratio of 1.0) and mixed, in the same manner as described above, and the mixture was then stirred using a vortex mixer at 2000 rpm for 2 minutes to obtain particles formed by self-assembly of the first and second polymers. When the particle sizes and their distribution were evaluated by dynamic light scattering, results with the same trend as described above were obtained (Table 6), suggesting a PDI of 0.2 and increased polydispersity in the presence of 20 mM NaCl.

TABLE 6

| NaCl concentration (mM) | Particle size (nm) | PDI |
|---|---|---|
| 0 | 132 | 0.058 |
| 10 | 151 | 0.065 |
| 20 | 190 | 0.2 |

[Reference Example I-4] Determining Crosslinking Rate

As the first polymer there was used the anionic block copolymer PEG-P(Asp), comprising polyethylene glycol (weight-average molecular weight: approximately 2000) (hereunder also referred to as "PEG") as an uncharged hydrophilic segment and polyaspartic acid (polymerization degree: approximately 75) as an anionic segment. The anionic polymer ends were labeled with Cy3 (labeling 10% of the number of anionic polymers). As the second polymer there was used the cationic homopolymer Homo-P(Asp-AP), comprising a poly(diaminopentane structure-containing asparagine derivative) (polymerization degree: approximately 82) (hereunder also referred to as "P(Asp-AP)"). Each was dissolved to 1 mg/mL in $D_2O$ with pD=7.4.

Both solutions were mixed to equal charge ratios, and the mixture was subjected to vortex mixing (2000 rpm, 2 minutes) to prepare a vacant vesicle-containing solution.

An EDC solution ($D_2O$, pD=7.4) was added at equivalent portions of 10, 5, 1, 0.5 and 0.1 with respect to the carboxyl groups of the Cy3-PEG-P(Asp) in the system, to prepare vacant crosslinked vesicle-containing solutions.

A centrifugal ultrafiltration membrane with a molecular cutoff of 300,000 (Vivaspin, product of GE Healthcare) was used for purification. The centrifugation conditions were 2000 rpm, 25° C.×10, with addition of fresh $D_2O$ for purification.

A 100 μL portion of a 10 mg/mL vacant crosslinked vesicle-containing solution (solvent: $D_2O$) was subjected to attenuated total reflection infrared spectroscopy (FTIR-6300, product of JASCO Corp.).

The peak at 1550-1600 cm$^{-1}$ obtained by attenuated total reflection infrared spectroscopy was separated using analysis software (IGOR Pro), and the crosslinking rate was calculated by quantifying the decrease in area corresponding to COO$^-$ (Table 7).

TABLE 7

| Amount of crosslinking agent used (eq.) | Crosslinking rate (%) |
|---|---|
| 0 | 0 |
| 0.1 | 9.5 |
| 0.5 | 38.6 |
| 1 | 55.9 |
| 5 | 74.2 |
| 10 | 89.9 |

[Reference Example I-5] Enclosure of FITC-Dex4k into Vacant Non-Crosslinked Vesicles In the same manner as Example I-1, fluorescein isothiocyanate-dextran (weight-average molecular weight: 4000) (product of Sigma-Aldrich, hereunder also referred to as "FITC-Dex4k") was enclosed in vacant vesicles prepared in the same manner as Example I-1, and the obtained FITC-Dex4k-encapsulating non-crosslinked vesicles were measured for particle size distribution, mean particle size and polydispersity index (PDI) by dynamic light scattering. As a result, when the FITC-Dex4k concentration was 10 mg/mL, the mean particle size was 107.4 nm and the PDI was 0.067, and when the FITC-Dex4k concentration was 15 mg/mL the mean particle size was 109.2 nm and the PDI was 0.078, (vacant vesicle mean particle size: 101.4 nm, PDI: 0.070), confirming that FITC-Dex4k had been enclosed in the vacant vesicles while maintaining their monodisperse property.

[Reference Example I-6] Ultrasonic Treatment of Vacant Non-Crosslinked Vesicles

Vacant vesicles prepared in the same manner as Example I-1 were subjected to ultrasonic treatment (2 min), and the ultrasonic-treated vesicles were measured for particle size distribution, mean particle size and polydispersity index (PDI) by dynamic light scattering. As a result, when ultrasonic treatment was conducted on an ice bath the mean particle size was 112.8 nm and the PDI was 0.098, and no problems were seen in the vesicle solution, but when ultrasonic treatment was not conducted in an ice bath, the mean particle size was 3606 nm and the PDI was 0.301, and the vesicle solution was opaque. This result suggests that it is preferred to conduct ultrasonic treatment of vesicles in such a manner that the vesicles are not excessively heated (for example, to conduct ultrasonic treatment in a non-continuous manner, or to cool the vesicles if ultrasonic treatment is conducted in a continuous manner).

[Example I-4] Production of Cytosine Deaminase-Enclosing Crosslinked Vesicles

Preparation and Evaluation of Cytosine Deaminase-Enclosing Crosslinked Vesicles

Crosslinked vesicles enclosing cytosine deaminase (CD) (cytosine deaminase ammonium sulfate suspension, product of Calzyme) were produced by the following procedure. CD is an enzyme that converts 5-fluorocytosine (hereunder also abbreviated as "5-FC") to 5-fluorouracil (hereunder also abbreviated as "5-FU").

To vacant vesicles prepared in the same manner as Example I-1 there was added EDC at 1.0 equivalent with respect to the carboxyl groups in the PEG-P(Asp), for crosslinking to prepare vacant crosslinked vesicles. A 500

μL portion of an approximately 3 mg/mL (as PEG-P(Asp)) dispersion of vacant crosslinked vesicles and a 500 μL portion of a 1 mg dispersion of cytosine deaminase (CD) were mixed and stirred with a vortex mixer (2000 rpm) for 2 minutes, to load the CD into the crosslinked vesicles. Next, EDC was added to 9.0 equivalents with respect to the carboxyl groups in the PEG-P(Asp), the mixture was left overnight at 4° C. for further crosslinking and purified by ultrafiltration under centrifugation at 4° C., 2000 rpm (molecular cutoff: 300,000, in PBS), to obtain 1 mL of a dispersion of CD-enclosing crosslinked vesicles.

Figure 12:
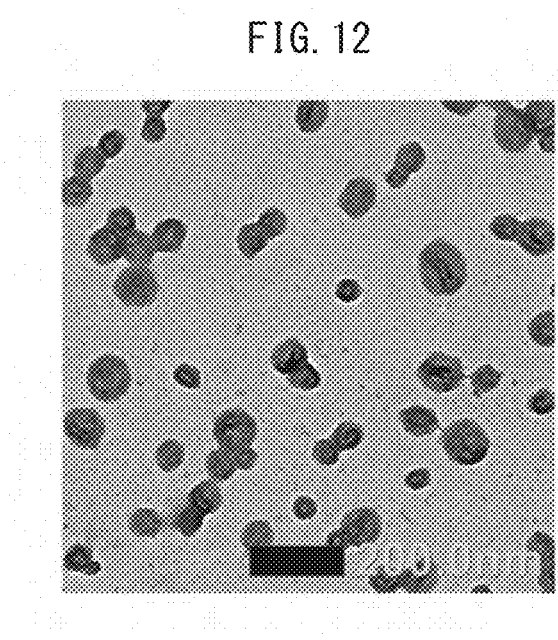
FIG. 12 is a transmission electron microscopic (TEM) image of the crosslinked vesicles encapsulating CD obtained in Example I-4.

The vacant crosslinked vesicles and the CD-enclosing crosslinked vesicles were measured by dynamic light scattering (DLS), and the mean particle size and polydispersity index (PDI) were determined. The results are shown in Table 8 below. Also, a transmission electron microscope photograph of the CD-enclosing crosslinked vesicles is shown in FIG. 12.

TABLE 8

|  | Mean particle size (nm) | PDI |
| --- | --- | --- |
| Vacant crosslinked vesicles | 98.6 | 0.045 |
| CD-enclosing crosslinked vesicles | 96.8 | 0.092 |

Figure 13:
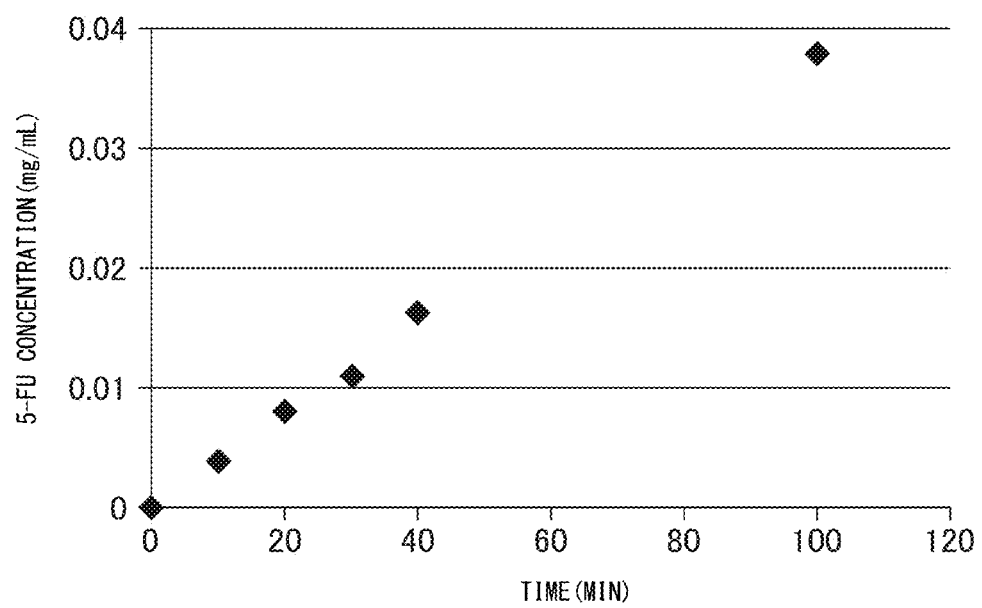
FIG. 13 is a graph showing the conversion rate of 5-FC into 5-FU by the crosslinked vesicles encapsulating CD obtained in Example I-4.

Conversion from 5-FC to 5-FU with Cytosine Deaminase-Enclosing Crosslinked Vesicles The conversion efficiency from 5-FC to 5-FU with CD-enclosing crosslinked vesicles was evaluated by the following procedure. A 0.15 mL portion of a dispersion of the CD-enclosing crosslinked vesicles prepared by the procedure described above was mixed with 0.15 ml of a 0.01 mg/mL 5-FC solution, and the 5-FU concentration of the liquid mixture was continuously monitored by liquid chromatography. The results are shown in the graph of FIG. 13. The 5-FC was converted to 5-FU by CD enclosed in the crosslinked vesicles. The conversion rate (enzyme activity) was 0.03 U/mL.

Figure 14:
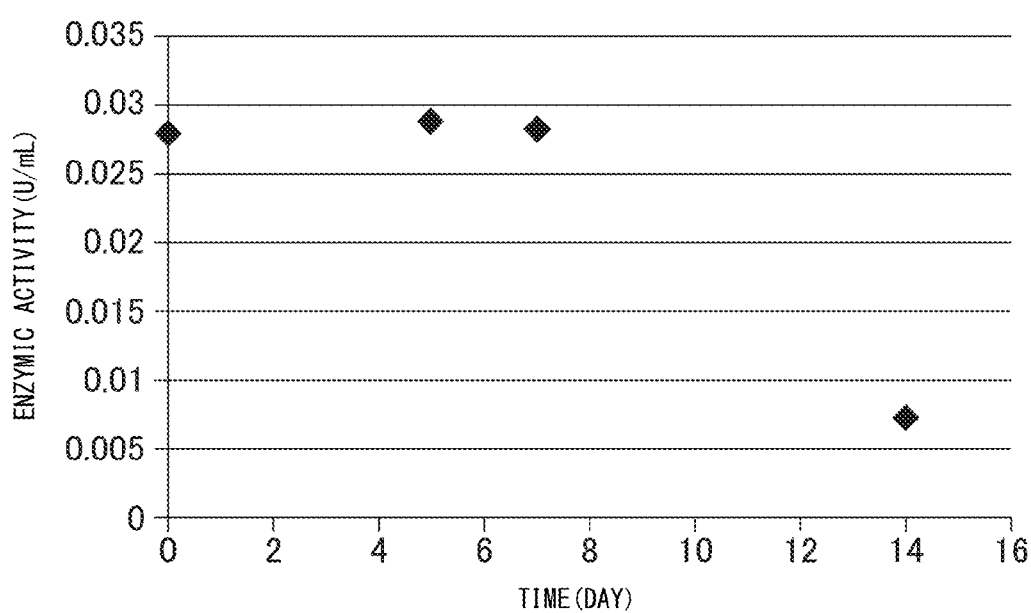
FIG. 14 is a graph showing stability in the enzyme activity of converting 5-FC into 5-FU by the crosslinked vesicles encapsulating CD obtained in Example I-4.

Stability of Enzyme Activity With Cytosine Deaminase-enclosing Crosslinked Vesicles The stability of enzyme activity with CD-enclosing crosslinked vesicles was evaluated by the following procedure. CD-enclosing crosslinked vesicles prepared by the procedure described above were stored in 10 mM PBS (pH 7.4, 150 mM NaCl) at 4° C. At days 0, 5, 7 and 14 after preparation, it was mixed with a 5-FC solution under the same conditions as above, and the 5-FU concentration in the liquid mixture after 40 minutes was measured by the method described above. The results are shown in the graph of FIG. 14. Enzyme activity was maintained at least for 7 days after preparation.

Tumor Treatment Effect by Cytosine Deaminase-Enclosing Crosslinked Vesicles

Mouse colon cancer cell line C26-transplanted BALB/c mice (6-week-old) were divided into 8 groups of 5 each (groups 1 to 8), and each group was intravenously administered 200 μL each of CD-enclosing crosslinked vesicles (0.5 U/mL) prepared by the procedure described above, 5-FC, 5-FU or PBS, at the timing shown in Table 9 below. The 5-FC and 5-FU were prepared for 10 mg/kg (body weight) or 80 mg/kg (body weight), based on the mouse body weight. Following administration, the tumor volume was measured during the survival period of each mouse, over a maximum period of 28 days, and the body weight of each mouse was also measured. The tumor volume was measured by measuring the long diameter and short diameter of the tumor using a caliper, and the calculation was performed by the following formula.

$$V = (a^2 \times b)/2$$

V: Tumor volume, a: long diameter, b: short diameter

TABLE 9

| Group | Day 0 | Day 3 | Day 7 | Day 10 | Day 14 |
| --- | --- | --- | --- | --- | --- |
| 1 | CD-enclosing crosslinked vesicles | 5-FC 10 mg/kg | 5-FC 10 mg/kg | 5-FC 10 mg/kg | 5-FC 10 mg/kg |
| 2 | CD-enclosing crosslinked vesicles | 5-FC 80 mg/kg | 5-FC 80 mg/kg | 5-FC 80 mg/kg | 5-FC 80 mg/kg |
| 3 | — | 5-FU 10 mg/kg | 5-FU 10 mg/kg | 5-FU 10 mg/kg | 5-FU 10 mg/kg |
| 4 | — | 5-FU 80 mg/kg | 5-FU 80 mg/kg | 5-FU 80 mg/kg | 5-FU 80 mg/kg |
| 5 | CD-enclosing crosslinked vesicles | — | — | — | — |
| 6 | — | 5-FC 10 mg/kg | 5-FC 10 mg/kg | 5-FC 10 mg/kg | 5-FC 10 mg/kg |
| 7 | — | 5-FC 80 mg/kg | 5-FC 80 mg/kg | 5-FC 80 mg/kg | 5-FC 80 mg/kg |
| 8 | — | PBS | PBS | PBS | PBS |

Figure 15:
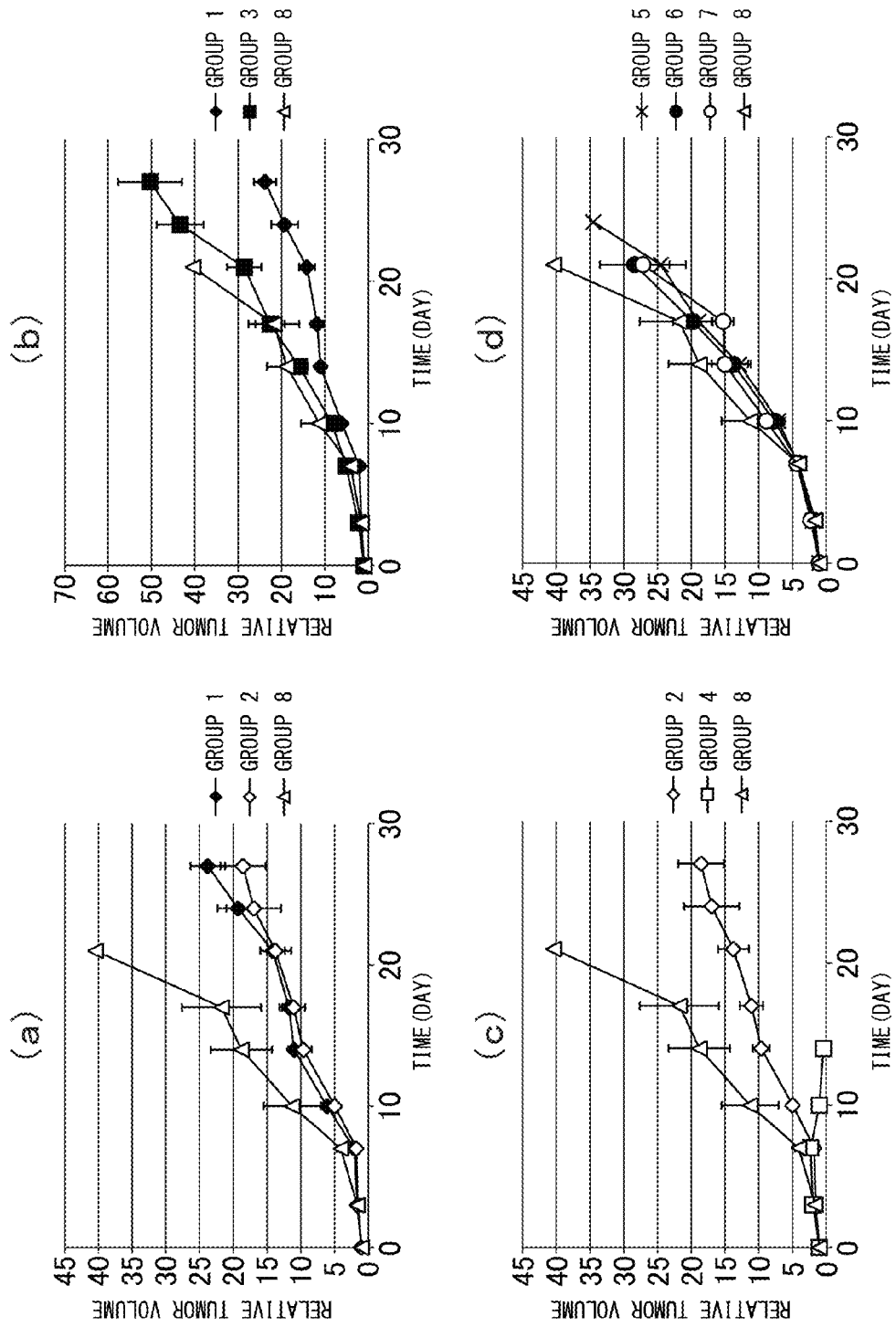
FIGS. 15 (a) to (d) are graphs showing the inhibitory effect of tumor growth by a therapy using the crosslinked vesicles encapsulating CD obtained in Example I-4.

The measurement results for tumor volume are shown in FIG. 15. The CD-enclosing crosslinked vesicle and 5-FC administered groups (Group 1: 10 mg/kg; Group 2: 80 mg/kg) exhibited significant antitumor effects compared to the non-treated group (Group 8), regardless of 5-FC dose (FIG. 15(*a*)). When the CD-enclosing crosslinked vesicle and 5-FC administered groups (Group 1: 10 mg/kg; Group 2: 80 mg/kg) and the 5-FU administered groups (Group 3: 10 mg/kg; Group 4: 80 mg/kg) were compared by dose, it was found that at a dose of 10 mg/kg, the 5-FU administered group (Group 3) only exhibited a very weak antitumor effect, whereas the CD-enclosing crosslinked vesicle and 5-FC administered group (Group 1) exhibited a significantly superior antitumor effect (FIG. 15(*b*)). At a dose of 80 mg/kg, the 5-FU administered group (Group 4) exhibited an antitumor effect that shrunk the tumor, but all of the individuals died by the 17th day after the initial administration due to side-effects, whereas in the CD-enclosing crosslinked vesicle and 5-FC administered group (Group 2), an antitumor effect was exhibited without side-effects, and all but one of the individuals survived even by the 28th day after the administration (FIG. 15(*c*)). In the CD-enclosing crosslinked vesicle only administered group (Group 5) and the 5-FC only administered group (Group 6: 10 mg/kg group; Group 7: 80 mg/kg group), no significant antitumor effect or toxicity was observed compared to the non-treated group (Group 8) (FIG. 15(*d*)).

Figure 16:
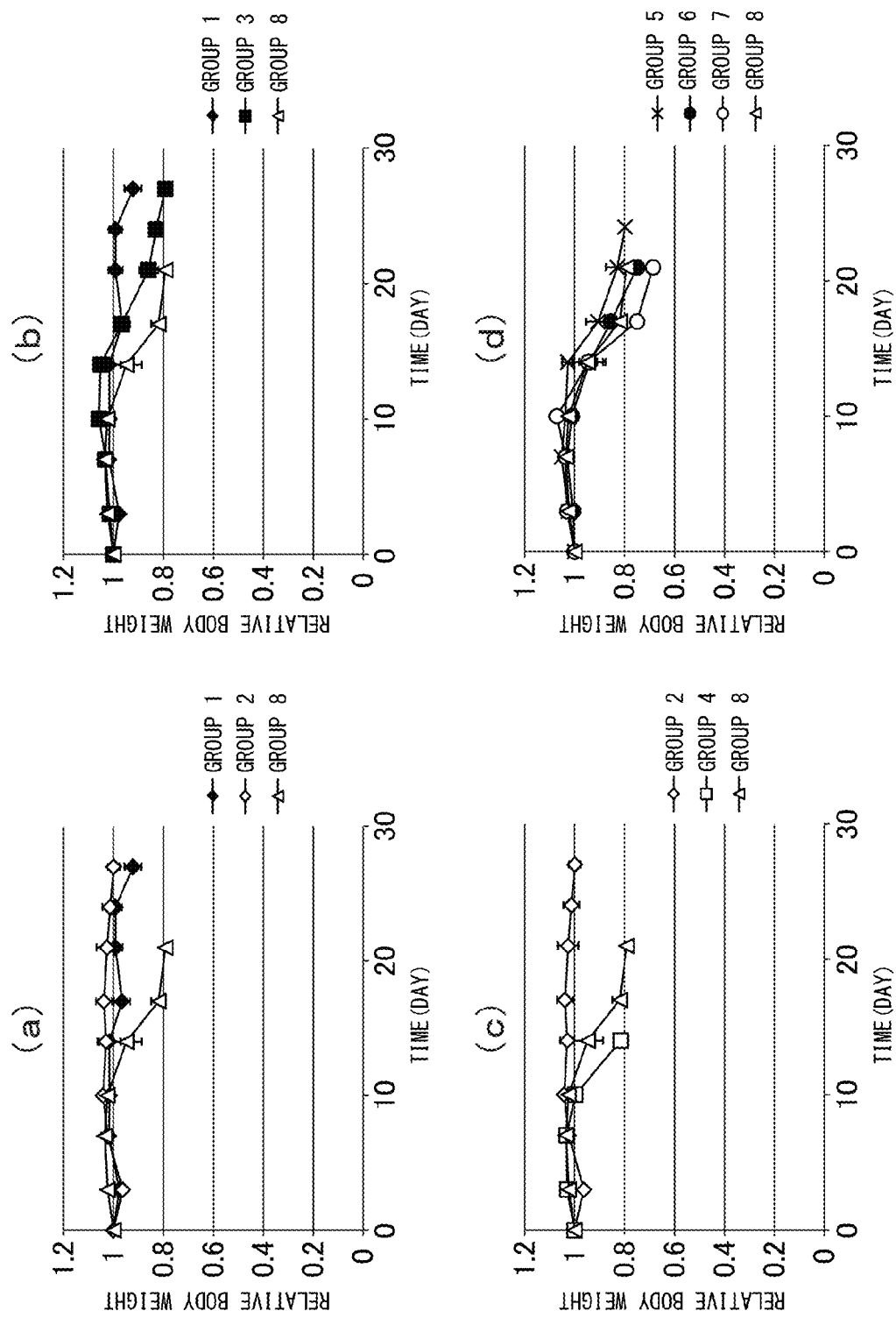
FIGS. 16 (a) to (d) are graphs showing the side effects (body weight loss) involved in a therapy using the crosslinked vesicles encapsulating CD obtained in Example I-4.

The measurement results for body weight change are shown in FIG. 16. In the CD-enclosing crosslinked vesicle and 5-FC administered groups (Group 1: 10 mg/kg; Group 2: 80 mg/kg), the relative body weight did not fall below 0.8 even by the 28th day after administration (FIG. 16(*a*)), but all of the other groups experienced a fall below 0.8 or death (FIG. 16(*b*) to (*d*)).

Figure 17:
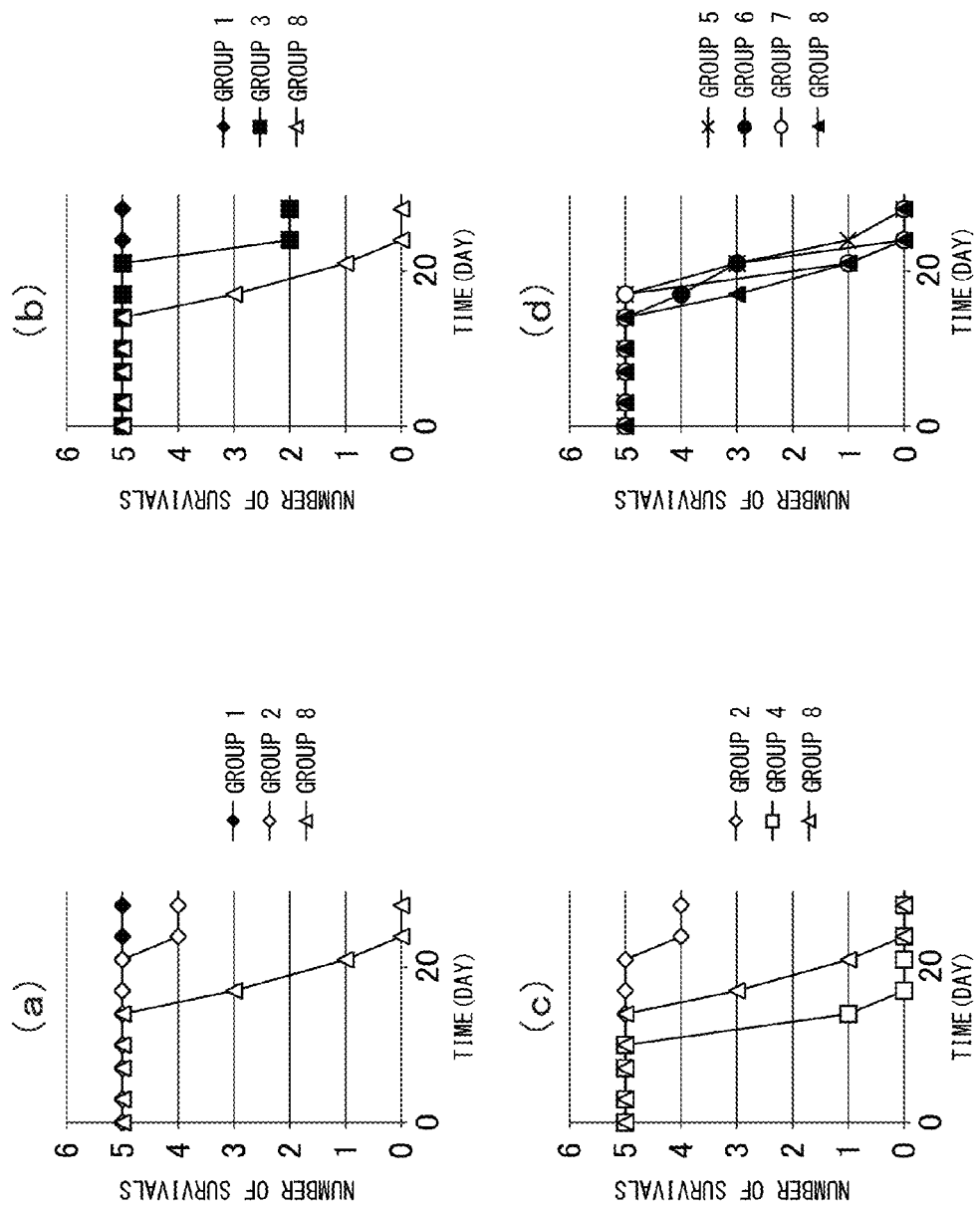
FIGS. 17 (a) to (d) are graphs showing the number of subjects who survived via a therapy using the crosslinked vesicles encapsulating CD obtained in Example I-4.

The summary results for survival number are shown in FIG. 17. In the CD-enclosing crosslinked vesicle and 5-FC administered groups (Group 1: 10 mg/kg; Group 2: 80 mg/kg), all individuals except one in Group 2 (80 mg/kg) survived even to the 28th day after administration (FIG. 17(*a*)), but 3 individuals in the 5-FU 10 mg/kg administered group (Group 3) and all in the other groups died by the 28th day after administration (FIG. 17(*b*) to (*d*)).

Evaluation of Blood Retention of Cytosine Deaminase-Enclosing Crosslinked Vesicles Three mouse colon cancer cell line C26-transplanted BALB/c mice (7-week-old) were prepared, and were intravenously administered 200 μL of Cy5-labeled CD-enclosing crosslinked vesicles (0.5 U/mL). At 24 hours and 72 hours after administration, the blood CD levels were measured based on Cy5 labeling.

Figure 18:
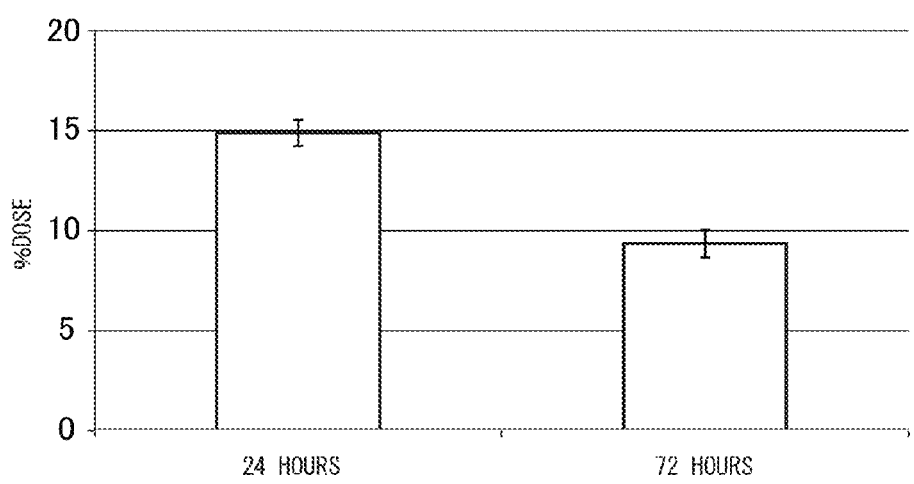
FIG. 18 is a graph showing the blood retention of the crosslinked vesicles encapsulating CD obtained in Example I-4.

The measurement results for the blood CD levels are shown in the graph of FIG. 18. With the CD-enclosing crosslinked vesicles, CD remained at a high concentration in the blood at both 24 hours and 72 hours after administration. This demonstrated that the CD-enclosing crosslinked vesicles have excellent blood retention.

[Comparative Example I-4] Introduction of CD into Non-Crosslinked Vesicles by Post-Loading Method A CD dispersion was added to a vacant vesicle dispersion before crosslinking, prepared in the same manner as Example I-1, and a vortex mixer was used for stirred mixing at 2000 rpm for 2 minutes, to prepare a vesicle dispersion having a charged polymer (first and second polymer) concentration of approximately 0.9 mg/mL and a post-mixing CD final concentration of 1 mg/mL. The dispersion was measured by dynamic light scattering (DLS) to determine the mean particle size and polydispersity index (PDI), but uniform particle formation could not be confirmed and the state was opaque.

[Example Group II] Adsorbent-Encapsulating Vesicles and their Production Method

[Example II-1] MSN-Encapsulating Vesicles 1

Materials:

As the first polymer there was used an anionic block copolymer PEG-P(Asp); zeta potential: −30.6 mV) comprising polyethylene glycol (PEG; molecular weight: approximately 2000) as an uncharged hydrophilic segment, and polyaspartic acid (P(Asp); polymerization degree: approximately 75) as an anionic segment.

As the second polymer there was used a cationic homopolymer (Homo-P(Asp-AP; zeta potential: +16.3 mV) comprising poly(diaminopentane structure-containing asparagine derivative) (P(Asp-AP); polymerization degree: approximately 82) as a cationic segment.

As adsorbent particles to be encapsulated there were used mesoporous silica nanoparticles (MSN), produced by the method described in Kim et al., Angew. Chem. Int. Ed. 2008, 47, 8438-8441. According to this reference, the obtained mesoporous silica nanoparticles have a total pore volume of 1.07 $cm^3/g$. Also, the mean particle size was about 50 nm and the zeta potential was −37 mV.

Preparation and Evaluation of MSN-Encapsulating Vesicles

The first and second polymers were each dissolved in a 10 mM phosphate buffer (pH 7.4) (aqueous medium), and 1.0 mg/mL of solutions with different polymer concentrations were prepared. Also, the MSN was dispersed in 10 mM phosphate buffer (pH 7.4) (aqueous medium) using ultrasonic irradiation, to prepare a dispersion with an MSN concentration of 1.0 mg/mL. The MSN dispersion was added to the solution of the second polymer in an Eppendorf tube, to an MSN concentration of 20 w/w % of the total polymer concentration (total concentration of first and second polymers), and the mixture was stirred with a vortex mixer at approximately 2000 rpm for 2 minutes, and then allowed to stand for 8 minutes. The first polymer solution was added to and mixed with the obtained dispersion in the Eppendorf tube, to an equal charge ratio with the second polymer (i.e. a C/A ratio of 1.0), and the mixture was then stirred using a vortex mixer at about 2000 rpm for 2 minutes to obtain a solution containing MSN-encapsulating vesicles (adsorbent-encapsulating vesicles) formed by self-assembly of the first and second polymers.

The obtained MSN-encapsulating vesicle-containing solution was measured by DLS to determine the particle size distribution, mean particle size and PDI. Formation of monodisperse particles with a mean particle size of 111 nm was confirmed. The PDI was 0.092.

Preparation and Evaluation of Crosslinked MSN-Encapsulating Vesicles

The MSN-encapsulating vesicle-containing solution was added to a solution containing EDC (product of Dojindo Laboratories, WSC) at 10 equivalents with respect to the carboxyl groups in the PEG-P(Asp), and the mixture was allowed to stand overnight for crosslinking by EDC reaction. The reaction by-product was removed by centrifugal ultrafiltration (VIVASPIN 20, product of Sartorius Stedium Biotech, molecular cutoff: 300,000; 2000 rpm, 25° C.) for purification, to obtain a solution containing crosslinked MSN-encapsulating vesicles.

Figure 19:
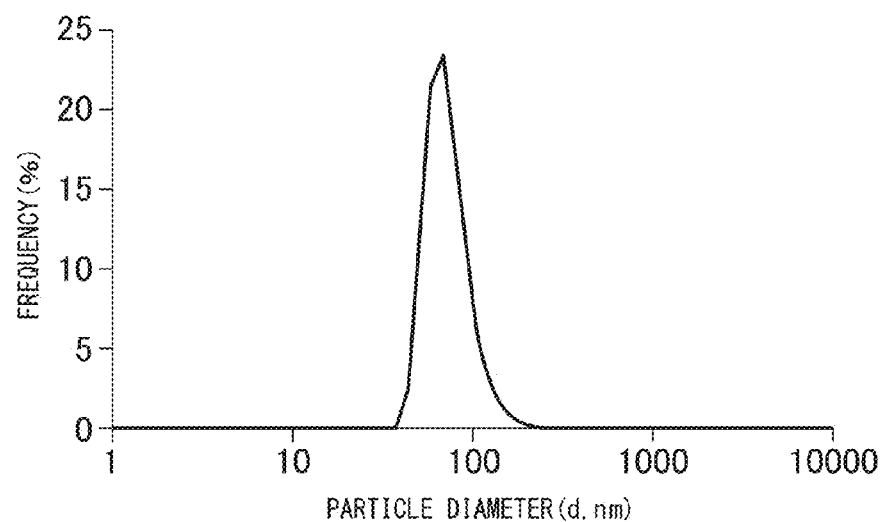
FIG. 19 is a graph showing the particle size distribution in a solution containing the crosslinked vesicles encapsulating MSN obtained in Example II-1.

The obtained crosslinked MSN-encapsulating vesicle-containing solution was measured by DLS to determine the particle size distribution, mean particle size and PDI. A graph of the particle size distribution is shown in FIG. 19. Formation of monodisperse particles with a mean particle size of 102 nm was confirmed. The PDI was 0.077 and the zeta potential was −17 mV.

Figure 20:
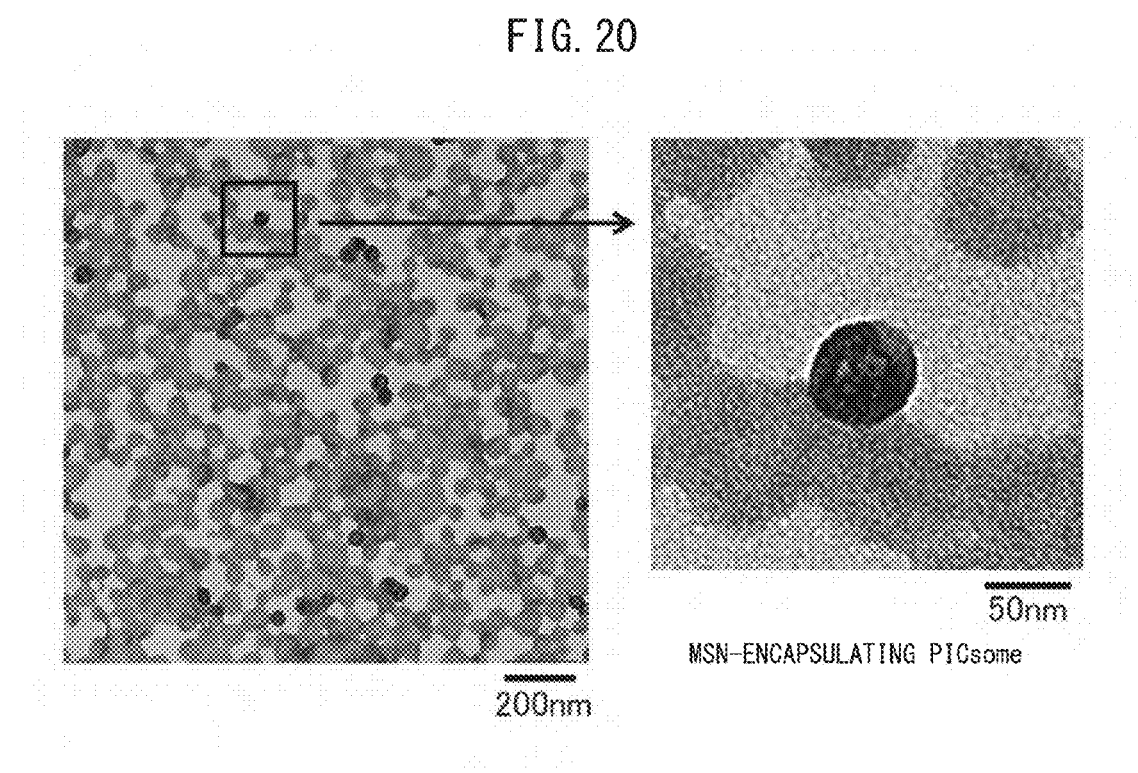
FIG. 20 is a TEM image of the crosslinked vesicles encapsulating MSN obtained in Example II-1.

Also, the morphology of the crosslinked MSN-encapsulating vesicle-containing solution was observed with a transmission electron microscope (TEM, JEM-1400 by JEOL Corp., same hereunder), confirming the validity of the DLS measurement results. The obtained TEM photograph is shown in FIG. 20. The particle size of the MSN-encapsulating vesicles (particles with high contrast in the photograph) was 60 to 70 nm, and the particle size of the simultaneously formed vacant vesicles (vesicles not encapsulating MSN) was approximately 100 nm. No MSN was observed that was not enclosed in vesicles.

Figure 21:
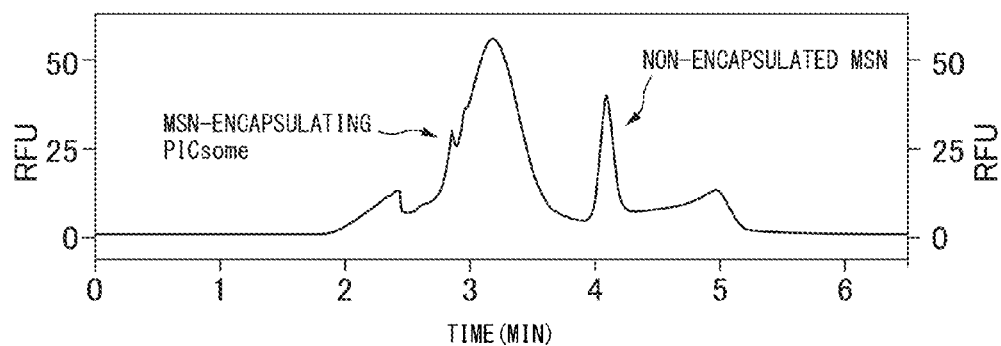
FIG. 21 is a capillary electrophoretic chromatogram of the crosslinked vesicles encapsulating MSN obtained in Example II-1.

Measurement of MSN Encapsulation Efficiency:

The following experiment was also carried out to examine the MSN encapsulation efficiency of the MSN-encapsulating vesicles. FITC-labeled MSN, having fluorescein isothiocyanate (FITC) adsorbed onto MSN, was used to prepare a solution containing crosslinked MSN-encapsulating vesicles, by the same method described above. The obtained crosslinked MSN-encapsulating vesicle-containing solution was measured by capillary electrophoresis (P/ACE MDQ, product of Beckman Coulter Inc.). The detector used was a fluorescence detector, the capillary used was one with an inner diameter of 75 μm (TSP075375 by Polymicro Technology), and the electrophoresis solution used was a 200 mM glycine-sodium hydroxide buffering solution (pH 8.0). The MSN-encapsulating vesicles and the MSN not encapsulated in vesicles were separated by capillary electrophoresis, based on the difference in surface charge. The obtained chromatogram is shown in FIG. 21. According to these results, 85% of the MSN was encapsulated in the vesicles.

Evaluation of Blood Retention:

The blood retention of the MSN-encapsulating vesicles was evaluated by the following procedure.

First, the following samples (i) to (iv) were prepared.

(i) Cy5-labeled MSN sample: Solution containing MSN adsorbing fluorescent dye Cy5 (Cy5 proportion of 0.4% with respect to MSN).

(ii) Cy5-labeled MSN-encapsulating vesicle sample: MSN-encapsulating vesicle-containing solution prepared by the same procedure as above, except for using the Cy5-labeled MSN used in (i) above instead of MSN.

(iii) MSN-encapsulating Cy5-labeled vesicle sample: MSN-encapsulating vesicle-containing solution prepared by the same procedure as above, except for using Cy5-labeled PEG-P(Asp) (Cy5 proportion of 10 mol % with respect to PEG-P(Asp)) instead of PEG-P(Asp).

Each of the samples (i) to (iv) above were injected into the tail vein of BALB/c mice (female, 6-week-old, 3 mice per sample) (0.2 mg/g body weight, as PEG-P(Asp)). After 1 hour, blood was collected and the fluorescent dye concentration of the obtained blood was measured using a fluorescent spectrometer (FP-7700 by JASCO Corp.). The obtained results (average for the 3 individuals administered each sample) are shown in Table 10 below.

TABLE 10

| | (i) Cy5-labeled MSN | (ii) Cy5-labeled MSN-encapsulating vesicles | (iii) MSN-encapsulating Cy5-labeled vesicles |
|---|---|---|---|
| Blood retention (%) | 24% | 87% | 86% |

[Example II-2] MSN-Encapsulating Vesicles 2

A solution containing vesicles encapsulating MSN (MSN-encapsulating vesicles: adsorbent-encapsulating vesicles) was obtained by the same procedure as in Example II-1, except that in the procedure of Example II-1, the mixing order of each solution of the first and second polymers and the MSN dispersion was changed, mixing the first polymer solution with the MSN dispersion first, and mixing the second polymer solution with the obtained liquid mixture.

The obtained MSN-encapsulating vesicle-containing solution was measured by DLS to determine the particle size distribution, mean particle size and PDI. Formation of monodisperse particles with a mean particle size of 103 nm was confirmed. The PDI was 0.059.

The obtained MSN-encapsulating vesicle-containing solution was used for crosslinking by the same procedure as in Example II-1, to obtain a solution containing crosslinked MSN-encapsulating vesicles.

Figure 22:
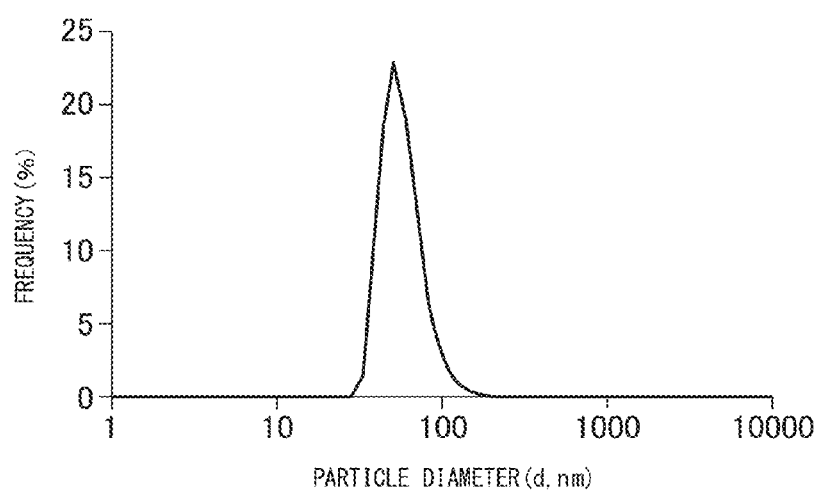
FIG. 22 is a graph showing the particle size distribution in a solution containing the crosslinked vesicles encapsulating MSN obtained in Example II-2.

The obtained crosslinked MSN-encapsulating vesicle-containing solution was measured by DLS to determine the particle size distribution, mean particle size and PDI. A graph of the particle size distribution is shown in FIG. 22. Formation of particles with a mean particle size of 101 nm was confirmed. The PDI was 0.152.

Figure 23:
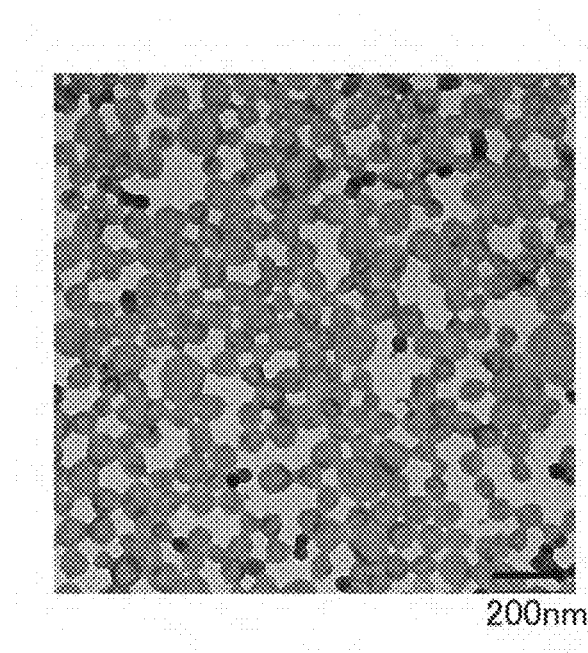
FIG. 23 is a TEM image of the crosslinked vesicles encapsulating MSN obtained in Example II-2.

Also, the morphology of the crosslinked MSN-encapsulating vesicle-containing solution was observed with a TEM, confirming the validity of the DLS measurement results. The obtained TEM photograph is shown in FIG. 23. The particle size of the MSN-encapsulating vesicles (particles with high contrast in the photograph) was 60 to 70 nm, and the particle size of the simultaneously formed vacant vesicles (vesicles not encapsulating MSN) was approximately 100 nm. Also, a slight amount of MSN was observed that was not enclosed in vesicles.

Figure 24:
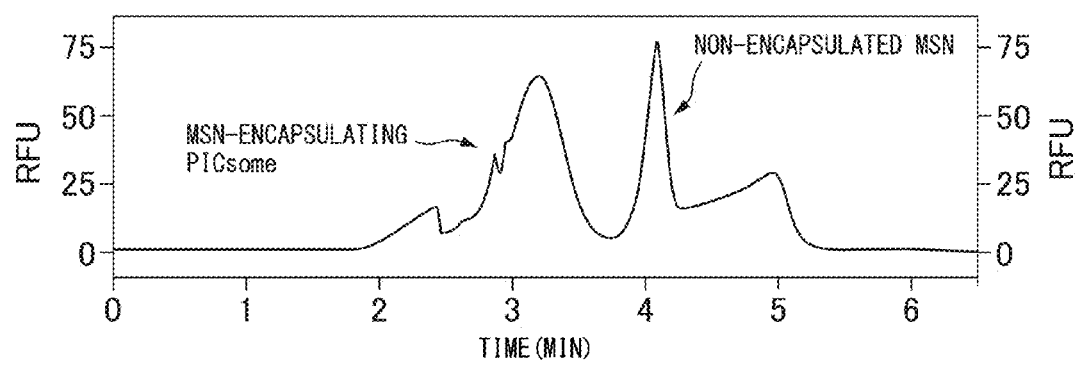
FIG. 24 is a capillary electrophoretic chromatogram of the crosslinked vesicles encapsulating MSN obtained in Example II-2.

In addition, in order to examine the MSN encapsulation efficiency, measurement was performed by capillary electrophoresis using the same procedure as in Example II-1. The obtained chromatogram is shown in FIG. 24. According to these results, 72% of the MSN was encapsulated in the vesicles.

[Reference Example II-1] MSN-Encapsulating Vesicles 3

A solution containing vesicles encapsulating MSN (MSN-encapsulating vesicles: adsorbent-encapsulating vesicles) was obtained by the same procedure as in Example II-1, except that in the procedure of Example II-1, the mixing order of each solution of the first and second polymers and the MSN dispersion was changed, mixing the first polymer solution and the second polymer solution first, and then mixing the MSN dispersion with the obtained liquid mixture.

The obtained MSN-encapsulating vesicle-containing solution was measured by DLS to determine the particle size distribution, mean particle size and PDI. Formation of monodisperse particles with a mean particle size of 104 nm was confirmed. The PDI was 0.049.

The obtained MSN-encapsulating vesicle-containing solution was used for crosslinking by the same procedure as in Example II-1, to obtain a solution containing crosslinked MSN-encapsulating vesicles.

Figure 25:
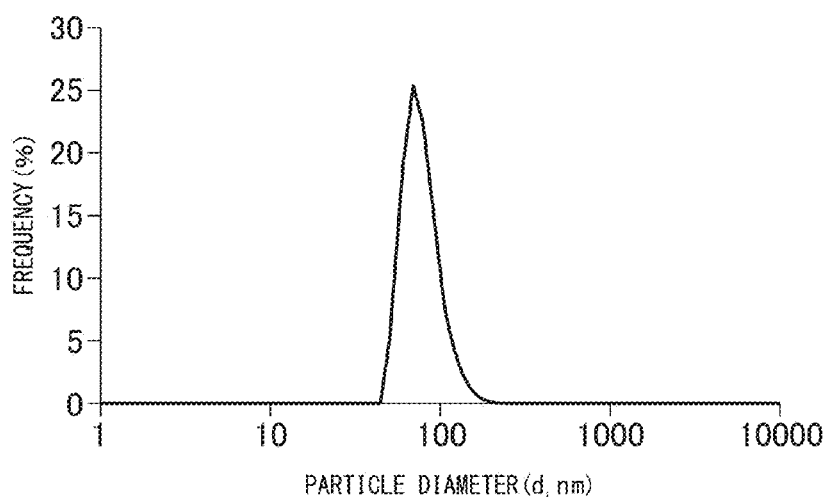
FIG. 25 is a graph showing the particle size distribution in a solution containing the crosslinked vesicles encapsulating MSN obtained in Reference Example II-1.

The obtained crosslinked MSN-encapsulating vesicle-containing solution was measured by DLS to determine the particle size distribution, mean particle size and PDI. A graph of the particle size distribution is shown in FIG. 25. Formation of particles with a mean particle size of 100 nm was confirmed. The PDI was 0.057.

Figure 26:
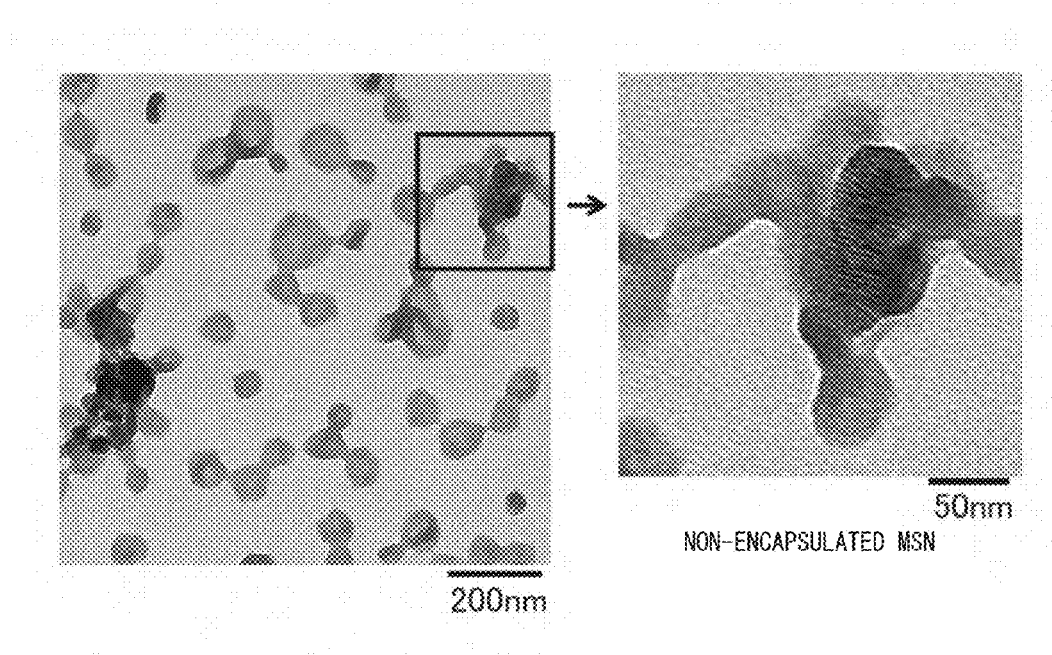
FIG. 26 is a TEM image of the crosslinked vesicles encapsulating MSN obtained in Reference Example II-1.

Also, the morphology of the crosslinked MSN-encapsulating vesicle-containing solution was observed with a TEM, confirming the validity of the DLS measurement results. The obtained TEM photograph is shown in FIG. 26. The particle size of the MSN-encapsulating vesicles (particles with high contrast in the photograph) was 60 to 70 nm, and the particle size of the simultaneously formed vacant vesicles (vesicles not encapsulating MSN) was approximately 100 nm. Also, some MSN was observed that was not enclosed in vesicles.

Figure 27:
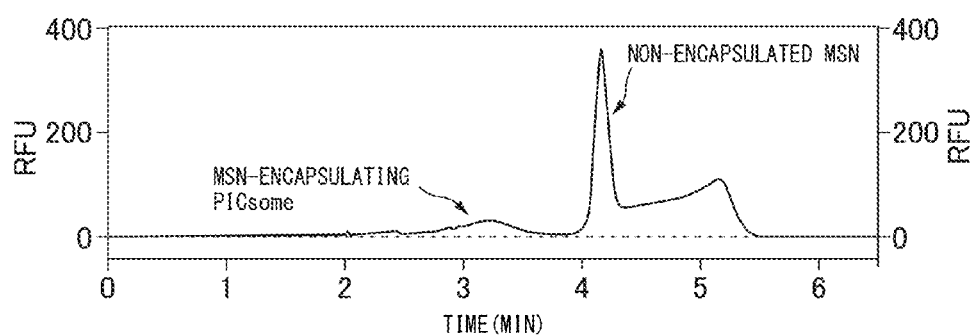
FIG. 27 is a capillary electrophoretic chromatogram of the crosslinked vesicles encapsulating MSN obtained in Reference Example II-1.

In addition, in order to examine the MSN encapsulation efficiency, measurement was performed by capillary electrophoresis using the same procedure as in Example 1. The obtained chromatogram is shown in FIG. 27. According to these results, 21% of the MSN was encapsulated in the vesicles.

[Example II-3A] Aminated MSN-Encapsulating Vesicles

Preparation of Aminated MSN-Encapsulating Vesicles:

A 50 µL portion of (3-aminopropyl)trimethoxysilane (APTS) was stirred with 4 mL of distilled water at ordinary temperature for 1 hour to dissolution. Next, 1 mL of a 10 mg/mL dispersion of MSN-encapsulating vesicles obtained by the same procedure as in Example II-1 described above (adsorbent-encapsulating vesicles) was added, and stirring was continued for 24 hours for surface treatment of the encapsulated MSN with APTS. It was then purified by ultrafiltration (molecular cutoff: 300,000, 20% ethanol×3, followed by 10 mM PBS (pH 7.4)×5), to obtain aminated MSN-encapsulating vesicles.

Evaluation of Aminated MSN-Encapsulating Vesicles—Mean Particle Size and PDI:

The untreated MSN-encapsulating vesicles before surface treatment and the aminated MSN-encapsulating vesicles were measured by dynamic light scattering (DLS), and the mean particle sizes and polydispersity indexes (PDI) were determined. The results are shown in Table 11 below. Also, transmission electron microscope photographs of the untreated MSN-encapsulating vesicles and aminated MSN-encapsulating vesicles are shown in FIGS. 28(a) and (b), respectively.

TABLE 11

|  | Mean particle size (nm) | PDI |
|---|---|---|
| Untreated MSN-encapsulating vesicles | 100.5 | 0.078 |
| Aminated MSN-encapsulating vesicles | 107.9 | 0.117 |

Evaluation of Aminated MSN-Encapsulating Vesicles—Surface Amino Groups:

The amounts of amino groups of the untreated MSN-encapsulating vesicles and aminated MSN-encapsulating vesicles were measured by TNBS assay. Specifically, 200 µL of buffer comprising 0.15 M sodium borate and 0.01 M aqueous sodium sulfite, 50 µL of a 0.1% aqueous solution of 2,4,6-trinitrobenzenesulfonic acid (TNBS), and 50 µL of a 2 mg/mL dispersion of untreated MSN-encapsulating vesicles or aminated MSN-encapsulating vesicles were mixed, the mixture was allowed to stand overnight at 37° C., and then the ultraviolet ray (UV) adsorbance was measured at a wavelength of 420 nm. The number of amino groups present in each of the MSN-encapsulating vesicles was determined from the obtained adsorbance. As a result, $8.14 \times 10^{19}$ more amino groups were detected per 1 mg of MSN in the aminated MSN-encapsulating vesicles than in the untreated MSN-encapsulating vesicles.

[Example II-3B] Mercaptized and Sulfonated MSN-Encapsulating Vesicles

Preparation of Mercaptized and Sulfonated MSN-Encapsulating Vesicles:

A 50 µL portion of (3-mercaptopropyl)trimethoxysilane (MPTS) was stirred with 4 mL of a 1% acetic acid aqueous solution at ordinary temperature for 1 hour to dissolution. Next, 1 mL of a 10 mg/mL dispersion of MSN-encapsulating vesicles obtained by the same procedure as in Example II-1 described above (adsorbent-encapsulating vesicles) was added, and stirring was continued for 24 hours to accomplish surface treatment of the encapsulated MSN with MPTS. Next, purification was performed by ultrafiltration (molecular cutoff: 300,000, 1% acetic acid aqueous solution×3, followed by water×5), to obtain mercaptized MSN-encapsulating vesicles. Next, 1 mL of a 30% aqueous hydrogen peroxide solution and 10 µL of concentrated sulfuric acid were added to the dispersion of mercaptized MSN-encapsulating vesicles, and the mixture was stirred for 12 hours for oxidation of the mercapto groups to convert them to sulfonate groups. It was then neutralized with a 5 M sodium hydroxide aqueous solution and diluted with water, and then purified by ultrafiltration (molecular cutoff: 300,000, 10 mM PBS (pH 7.4)×5), to obtain sulfonated MSN-encapsulating vesicles.

Evaluation of Mercaptized and Sulfonated MSN-Encapsulating Vesicles—Mean Particle Size and PDI:

The untreated MSN-encapsulating vesicles before surface treatment, the mercaptized MSN-encapsulating vesicles and the sulfonated MSN-encapsulating vesicles were measured by dynamic light scattering (DLS), and the mean particle sizes and polydispersity indexes (PDI) were determined. The results are shown in Table 12 below. Also, transmission electron microscope photographs of the untreated MSN-encapsulating vesicles and sulfonated MSN-encapsulating vesicles are shown in FIGS. 29(a) and (b), respectively.

TABLE 12

|  | Mean particle size (nm) | PDI |
|---|---|---|
| Untreated MSN-encapsulating vesicles | 100.5 | 0.078 |
| Mercaptized MSN-encapsulating vesicles | 106.6 | 0.122 |
| Sulfonated MSN-encapsulating vesicles | 109.1 | 0.113 |

Figure 30:
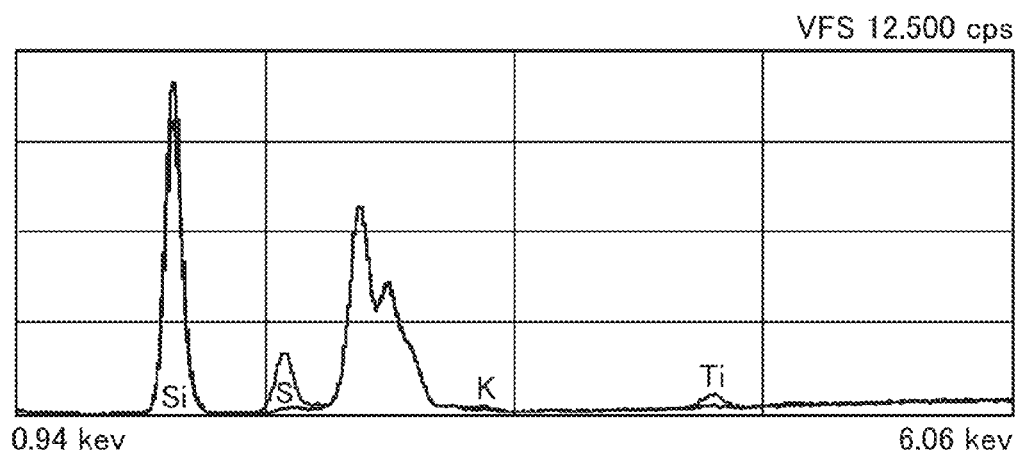
FIG. 30 indicates X-ray analysis spectrums of the untreated vesicles encapsulating MSN used in Example II-3B and the resultant sulfonated vesicles encapsulating MSN.

Evaluation of Sulfonated MSN-Encapsulating Vesicles—MSN Surface Sulfate Groups:

In addition, the presence of sulfate groups on the untreated MSN-encapsulating vesicles and sulfonated MSN-encapsulating vesicles was confirmed using an X-ray analysis microscope (XGT-5200WR by Horiba, Ltd.). The obtained X-ray analysis spectrum is shown in FIG. 30. With the sulfonated MSN-encapsulating vesicles, an S peak corresponding to sulfate groups was confirmed, whereas no S peak was confirmed with the untreated MSN-encapsulating vesicles.

[Example II-4A] Rose Bengal-Adsorbed Aminated MSN-Encapsulating Vesicles

Preparation of Rose Bengal-Adsorbed Aminated MSN-Encapsulating Vesicles:

Rose bengal (hereunder also abbreviated as "RB") was added to and mixed with the dispersion of aminated MSN-encapsulating vesicles obtained in Example II-3A, for adsorption of the rose bengal onto the aminated MSN-encapsulating vesicles. The non-adsorbed rose bengal was removed by ultrafiltration (molecular cutoff: 300,000). The RB content of the obtained RB-adsorbed aminated MSN-encapsulating vesicles was 3.2 w/w %. The chemical formula of rose bengal is shown below.

[Chemical Formula 11]

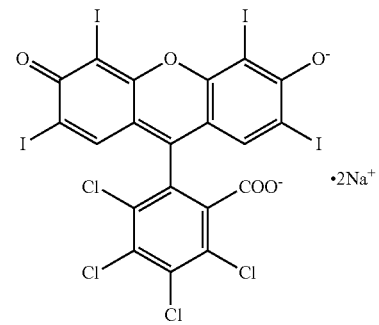

Figure 31:
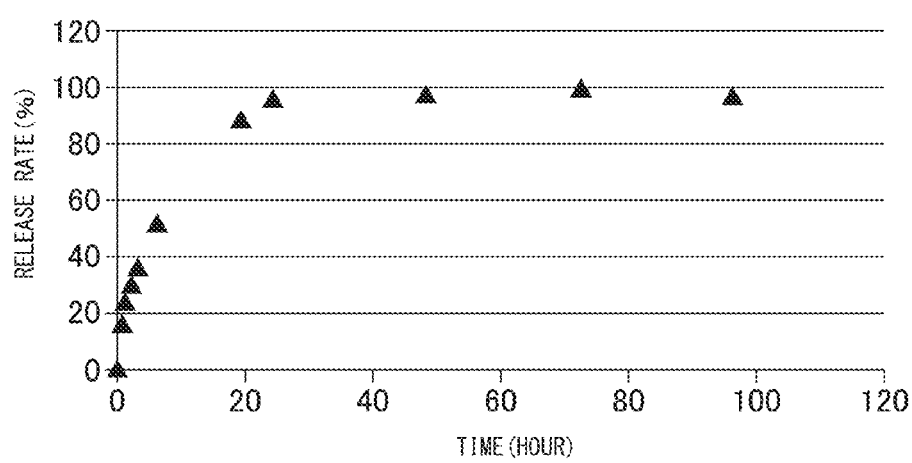
FIG. 31 is a graph showing the release profile of rose bengal from the aminated vesicles encapsulating MSN adsorbing rose bengal obtained in Example II-4A.

Evaluation of Rose Bengal-Adsorbed Aminated MSN-Encapsulating Vesicles—Release Property:

The RB-adsorbed aminated MSN-encapsulating vesicles were measured for Rose Bengal release property in 10 mM PBS (pH 7.4, 150 mM NaCl) at 37° C. The obtained results are shown in the graph of FIG. 31. Approximately 95% of the Rose Bengal was released by 24 hours.

[Example II-4B] Gemcitabine-Adsorbed Sulfonated MSN-Encapsulating Vesicles

Preparation of Gemcitabine-Adsorbed Sulfonated MSN-Encapsulating Vesicles:

Gemcitabine (hereunder also abbreviated as "GEM") was added to and mixed with the dispersion of sulfonated MSN-encapsulating vesicles obtained in Example II-3B, for adsorption of the gemcitabine onto the sulfonated MSN-encapsulating vesicles. The non-adsorbed gemcitabine was removed by ultrafiltration (molecular cutoff: 300,000). The GEM contents of the obtained GEM-adsorbed sulfonated MSN-encapsulating vesicles were 7.9 w/w % (10 mM PBS sample) and 8.1 w/w % (simulated body fluid sample).

Figure 32:
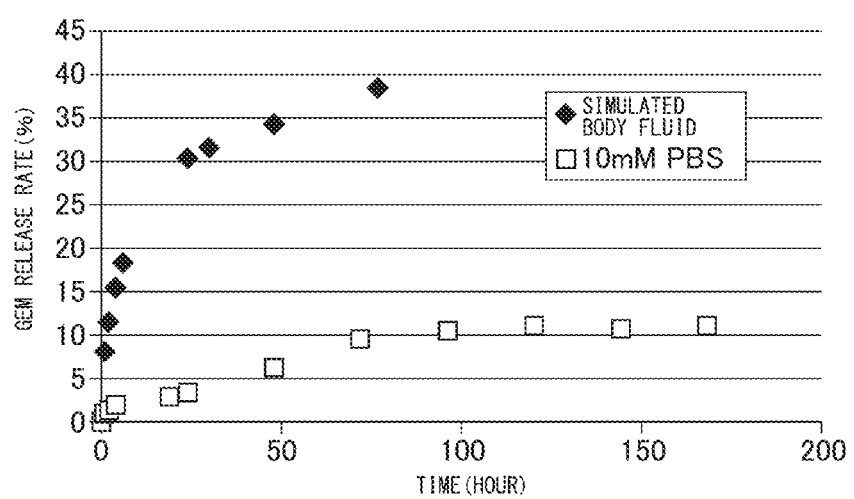
FIG. 32 is a graph showing the release profile of gemcitabine from the sulfonated vesicles encapsulating MSN adsorbing gemcitabine obtained in Example II-4B.

Evaluation of Gemcitabine-Adsorbed Sulfonated MSN-Encapsulating Vesicles—Release Property:

The obtained GEM-adsorbed sulfonated MSN-encapsulating vesicles were measured for gemcitabine release property in 10 mM PBS (pH 7.4, 150 mM NaCl) or simulated body fluid (SBF) at 37° C. The simulated body fluid was prepared as described in T. Kokubo, H. Kushitani, S. Sakka, T. Kitsugi and T. Yamamuro, "Solutions able to reproduce in vivo surface-structure changes in bioactive glass-ceramic A-W", J. Biomed. Mater. Res., 24, 721-734 (1990). The obtained results are shown in the graph of FIG. 32. Significantly differing gemcitabine release properties were obtained in the 10 mM PBS and in the simulated body fluid. This may be due to the differences in ionic strength or ion species.

Evaluation of Gemcitabine-Adsorbed Sulfonated MSN-Encapsulating Vesicles—Cell Uptake Property and Cytotoxic Effect on A549 Cells:

The cell uptake property and cytotoxic effect of the GEM-adsorbed sulfonated MSN-encapsulating vesicles on A549 cells (adenocarcinomic human alveolar basal epithelial cells) were evaluated by the following procedure, using the following samples.

Sample No. 1: GEM-adsorbed sulfonated MSN-encapsulating vesicles
Sample No. 2: Sulfonated MSN-encapsulating vesicles
Sample No. 3: GEM-adsorbed sulfonated MSN
Sample No. 4: Sulfonated MSN
Sample No. 5: Vacant vesicles
Sample No. 6: GEM alone Specifically, the GEM-adsorbed sulfonated MSN-encapsulating vesicles obtained by the procedure described above (sample No. 1), the sulfonated MSN-encapsulating vesicles used as material for the foregoing (Example II-3A) (sample No. 2) and the vacant vesicles used as material for the foregoing (Example II-1) (sample No. 5) were each labeled with Cy3 (labeling 25% of the number of anionic polymers), and then A549 cells were added to each well of a plate having a density of 2.2×10³ cells/well in RPMI-1640 medium, prior to culturing at 37° C. The amount of GEM-adsorbed sulfonated MSN-encapsulating vesicles (sample No. 1) added was an amount for a gemcitabine concentration of 0.5 µg/mL in the medium, the amounts of sulfonated MSN-encapsulating vesicles (sample No. 2) and vacant vesicles (sample No. 5) added were adjusted to be the same as the amount of GEM-adsorbed sulfonated MSN-encapsulating vesicles (sample No. 1) in terms of MSN-encapsulating vesicles.

Also, for comparison, sulfonated MSN (sample No. 4) obtained by sulfonating the MSN used as material for each of the MSN-encapsulating vesicles, by the same procedure as Example II-3A (mercaptization by MPTS surface treatment followed by oxidation), GEM-adsorbed sulfonated MSN (GEM content: 8.1 w/w %) (sample No. 3) obtained by adsorption of gemcitabine onto MSN, and gemcitabine alone (sample No. 6), were each added to the cells, which were then cultured. The GEM-adsorbed sulfonated MSN (sample No. 3) and gemcitabine alone (sample No. 6) were added to a gemcitabine concentration of 0.5 µg/mL in the medium, and amount of sulfonated MSN (sample No. 4) added was adjusted to be the same as the amount of GEM-adsorbed sulfonated MSN (sample No. 3) in terms of MSN.

The cell uptakes of the MSN-encapsulating vesicle samples (sample Nos. 1, 2 and 5) at 48 hours and 72 hours after the start of culturing were evaluated by the following procedure. Specifically, the cytoplasm of the cultured cells was stained with calcein (Calcein, AM, product of Invitrogen) and the cell nuclei were stained with Hoechst (Hoechst33342, product of Invitrogen), and then the Cy3 fluorescence due to MSN-encapsulating vesicles in the cells was observed at an excitation wavelength of 550 nm, using an InCell Analyzer 1000 (product of GE Healthcare Bioscience). The obtained results are shown in FIG. 33(a). In addition, Trypan blue (Trypan blue stain, 0.4%, product of Invitrogen) was used to distinguish the fluorescent substance not taken up into the cells, and the Cy3 fluorescence due to each of the MSN-encapsulating vesicles being taken up into the cells was observed in the same manner. The obtained results are shown in FIG. 33(b). It was found that the virtually none of the vacant vesicles (sample No. 5) were taken up into cells, whereas the GEM-adsorbed sulfonated MSN-encapsulating vesicles (sample No. 1) and sulfonated MSN-encapsulating vesicles (sample No. 2) were both taken up into cells.

Also, the cytotoxic effects of each of the samples (sample Nos. 1 to 6) at 48 hours and 72 hours after the start of culturing were evaluated by the following procedure. Specifically, using a Cell Counting Kit-8 (product of Dojindo) according to the manufacturer's instructions, reagent was added to each well and culturing was conducted for 1 hour, after which the viable cell count was measured. The results after 48 hours of culturing are shown in FIG. 34(a), and the results after 72 hours of culturing are shown in FIG. 34(b). The GEM-adsorbed sulfonated MSN-encapsulating vesicles (sample No. 1) were found to have a powerful cytotoxic effect equivalent to that of GEM-adsorbed sulfonated MSN (sample No. 3) and gemcitabine alone (sample No. 6). Also, while a weak cytotoxic effect was found for the sulfonated MSN (sample No. 4), no cytotoxic effect was found for the sulfonated MSN-encapsulating vesicles (sample No. 2) or vacant vesicles (sample No. 5).

Evaluation of Gemcitabine-Adsorbed Sulfonated MSN-Encapsulating Vesicles—Cell Uptake Property and Cytotoxic Effect on C26 Cells:

In addition, using C26 cells (a murine colon adenocarcinoma cell line) instead of A549 cells, the cell uptake property and cytotoxic effect were evaluated by the same procedure described above, except for the points mentioned below. The amounts of GEM-adsorbed sulfonated MSN-encapsulating vesicles (sample No. 1), GEM-adsorbed sulfonated MSN (sample No. 3) and gemcitabine alone (sample No. 6) added were amounts for a gemcitabine concentration of 0.1 µg/mL in the medium, the amounts of sulfonated MSN-encapsulating vesicles (sample No. 2) and vacant vesicles (sample No. 5) added were adjusted to be the same as the amount of GEM-adsorbed sulfonated MSN-encapsulating vesicles (sample No. 1) in terms of MSN-encapsulating vesicles, and the amount of sulfonated MSN (sample No. 4) added was adjusted to be the same as the amount of GEM-adsorbed sulfonated MSN (sample No. 3) in terms of MSN.

As the evaluation results for cell uptake, the measurement results for total intracellular Cy3 fluorescence quantity in the absence of Trypan blue are shown in FIG. 35(*a*), and the measurement results for live cell intracellular Cy3 fluorescence quantity with Trypan blue staining are shown in FIG. 35(*b*). For all of the MSN-encapsulating vesicle samples, cell uptake was less in the C26 cells compared to the A549 cells. Thus, the different amounts of cell uptake were attributed to the difference in cell type.

Also, as the evaluation results for cytotoxic action, the results after 48 hours of culturing are shown in FIG. 36(*a*), and the results after 72 hours of culturing are shown in FIG. 36(*b*). For C26 cells as well, similar to A549 cells, the GEM-adsorbed sulfonated MSN-encapsulating vesicles (sample No. 1) were found to have a powerful cytotoxic effect equivalent to that of GEM-adsorbed sulfonated MSN (sample No. 3) and gemcitabine alone (sample No. 6). Also, while a weak cytotoxic effect was found for the sulfonated MSN (sample No. 4), no cytotoxic effect was found for the sulfonated MSN-encapsulating vesicles (sample No. 2) or vacant vesicles (sample No. 5).

Evaluation of Gemcitabine-Adsorbed Sulfonated MSN-Encapsulating Vesicles—Tumor Treatment Effect Using Mice:

Human pulmonary carcinoma cell line A549-transplanted BALB/c nude mice (7-week-old, for each sample) were divided into 7 groups of 5 each, among which 6 of the groups were intravenously administered samples 1 to 6 (Groups 1 to 6), respectively. The dose of each sample was 200 µL, and the concentration of each sample of the GEM-adsorbed sulfonated MSN-encapsulating vesicles (sample No. 1), the GEM-adsorbed sulfonated MSN (sample No. 3) and the gemcitabine alone (sample No. 6) was adjusted for a gemcitabine concentration of 5 mg/kg of mouse body weight, while the amounts of sulfonated MSN-encapsulating vesicles (sample No. 2) and vacant vesicles (sample No. 5) added were adjusted to be the same as the amount of GEM-adsorbed sulfonated MSN-encapsulating vesicles (sample No. 1) in terms of MSN-encapsulating vesicles, and the amount of sulfonated MSN (sample No. 4) added was adjusted to be the same as the amount of GEM-adsorbed sulfonated MSN (sample No. 3) in terms of MSN. To the remaining group there was administered 200 µL of PBS (Group 7). The tumor volumes were measured for 28 days after administration. Tumor volume was measured by measuring the long diameter and short diameter of the tumor using a caliper, and calculation was performed by the following formula.

$$V=(a^2 \times b)/2$$

V: Tumor volume, a: long diameter, b: short diameter

The measurement results for tumor volume are shown in the graph of FIG. 37. The sulfonated MSN-encapsulating vesicle-administered group (Group 2), the GEM-adsorbed sulfonated MSN-administered group (Group 3), the sulfonated MSN-administered group (Group 4) and the vacant vesicle-administered group (Group 5) all exhibited no significant difference from the PBS-administered group (Group 7), and no significant antitumor effect was seen. Also, while some suppression of tumor growth occurred in the GEM alone-administered group (Group 6), the difference was not significant compared to the PBS-administered group (Group 7), and no significant antitumor effect was seen. On the other hand, in the GEM-adsorbed sulfonated MSN-encapsulating vesicle-administered group (Group 1), tumor growth was significantly suppressed not only compared to the PBS-administered group (Group 7) but even compared to the GEM alone-administered group (Group 6), and therefore a significant antitumor effect was found. This demonstrated that GEM-adsorbed sulfonated MSN-encapsulating vesicles according to the invention (sample 1) can effectively deliver GEM to tumor sites, and can exhibit high antitumor effects at low doses even compared to GEM alone.

Evaluation of Gemcitabine-Adsorbed Sulfonated MSN-Encapsulating Vesicles—Blood Retention and Tumor Distribution Evaluation Using Mice:

Human pulmonary carcinoma cell line A549-transplanted BALB/c nude mice (7-week-old, for each sample) were divided into 4 groups of 3 each. Two of the groups were intravenously administered GEM-adsorbed sulfonated MSN-encapsulating vesicles wherein MSN was labeled with Cy5 (sample No. 1) (Groups A1 and A2), while the other two groups were intravenously administered GEM-adsorbed sulfonated MSN labeled with Cy5 (sample No. 3) (Groups B1 and B2). The dose of each sample was 200 µL, and the concentration of each sample was adjusted for a gemcitabine concentration of 5 mg/kg (body weight) with respect to the body weight of the mice. The animals were slaughtered at 24 hours (Groups A1 and B1) and 72 hours (Groups A2 and B2) after administration, and the blood concentrations and tumor concentrations of GEM-adsorbed sulfonated MSN-encapsulating vesicles and GEM-adsorbed sulfonated MSN were measured based on Cy5 fluorescence quantity, by the same method described above.

Figure 38:
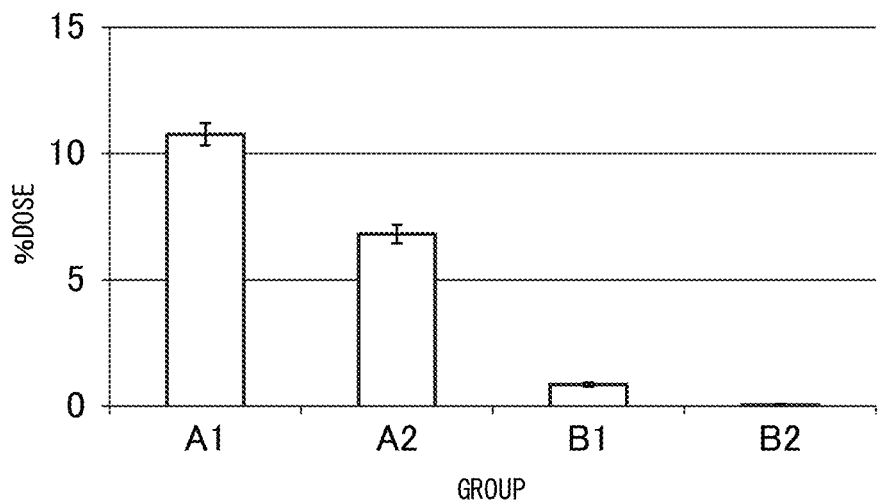
FIG. 38 is a graph showing the blood retention rate of the sulfonated vesicles encapsulating MSN adsorbing gemcitabine obtained in Example II-4B.

The measurement results of the blood concentrations of the GEM-adsorbed sulfonated MSN-encapsulating vesicles and GEM-adsorbed sulfonated MSN are shown in the graph in FIG. 38. In the GEM-adsorbed sulfonated MSN-encapsulating vesicle-administered groups (Groups A1 and A2), the blood concentrations were much higher at both 24 hours and 72 hours after administration compared to the GEM-adsorbed sulfonated MSN-administered groups (Groups B1 and B2, indicating excellent blood retention.

Figure 39:
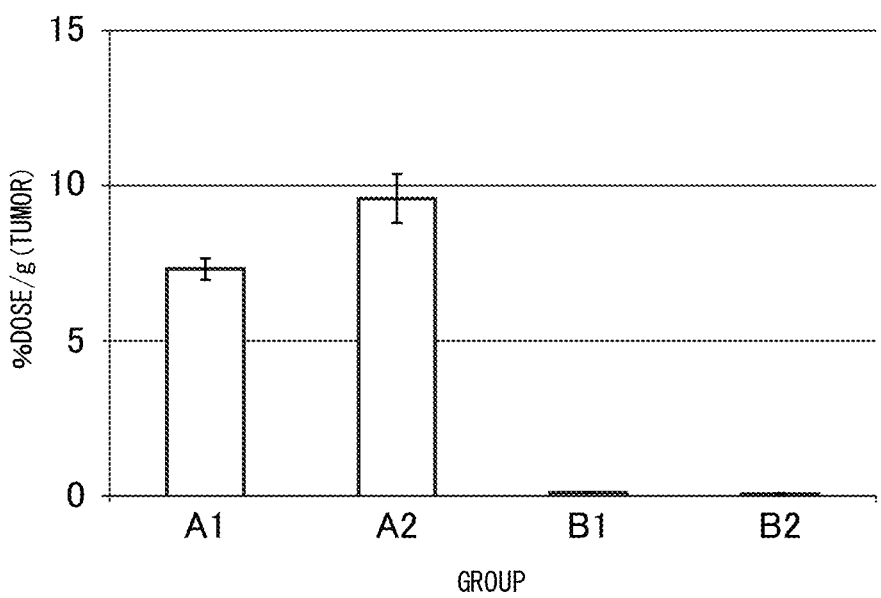
FIG. 39 is a graph showing the tumor accumulation rate of the sulfonated vesicles encapsulating MSN adsorbing gemcitabine obtained in Example II-4B.

Also, the measurement results for tumor concentrations of the GEM-adsorbed sulfonated MSN-encapsulating vesicles and GEM-adsorbed sulfonated MSN are shown in the graph in FIG. 39. In the GEM-adsorbed sulfonated MSN-encapsulating vesicle-administered groups (Groups A1 and A2), the tumor concentrations were much higher at both 24 hours and 72 hours after administration compared to the GEM-adsorbed sulfonated MSN-administered groups (Groups B1 and B2, indicating excellent tumor accumulation.

[Example Group III] Poorly Water-Soluble Substance-Encapsulating Vesicles and their Production Method

[Example III-1] Production of Indigo-Based Dye-Encapsulating Vesicles with β-Galactosidase-Encapsulating Crosslinked Vesicles Materials:

As the first polymer there was used an anionic block copolymer PEG-P(Asp); zeta potential: −30.6 mV) comprising polyethylene glycol (PEG; molecular weight: approximately 2000) as an uncharged hydrophilic segment, and polyaspartic acid (P(Asp); polymerization degree: approximately 75) as an anionic segment.

As the second polymer there was used a cationic homopolymer (Homo-P(Asp-AP); zeta potential: +16.3 mV) comprising poly(diaminopentane structure-containing asparagine derivative) (P(Asp-AP); polymerization degree: approximately 82) as a cationic segment.

The enzyme used as the substance to be encapsulated was β-galactosidase.

Preparation and Evaluation of Enzyme-Encapsulating Vesicles:

The first and second polymers were each dissolved in a 10 mM phosphate buffer (pH 7.4) (aqueous medium), to prepare solutions with respective polymer concentrations of 1.0 mg/mL. Also, β-galactosidase (enzyme) was dissolved in 10 mM phosphate buffer (pH 7.4, 150 mM sodium chloride-containing) to a concentration of 1 mg/mL, to prepare a solution. The obtained first polymer solution and second polymer solution were placed in an Eppendorf tube to an equal charge ratio (i.e. a C/A ratio of 1.0) and mixed, and then stirred with a vortex mixer at about 2000 rpm for 2 minutes to obtain a solution containing the vesicles (vacant vesicles) formed by self-assembly of the first and second polymers.

To the obtained vesicle-containing solution there was added the aforementioned β-galactosidase solution at the same volume as the second polymer solution used, and the mixture was stirred with a vortex mixer at about 2000 rpm for 2 minutes to encapsulate the β-galactosidase in the vesicles and obtain a solution containing β-galactosidase-encapsulating vesicles (enzyme-encapsulating vesicles).

The obtained β-galactosidase-encapsulating vesicle-containing solution was added to a solution containing EDC (product of Dojindo Laboratories, WSC) at 10 equivalents with respect to the carboxyl groups in the PEG-P(Asp), and the mixture was allowed to stand overnight for crosslinking by EDC reaction. The reaction by-product was removed by centrifugal ultrafiltration (VIVASPIN 20, product of Sartorius Stedium Biotech, molecular cutoff: 300,000; 2000 rpm, 25° C.) for purification, to obtain a solution containing crosslinked β-galactosidase-encapsulating vesicles.

Figure 40:
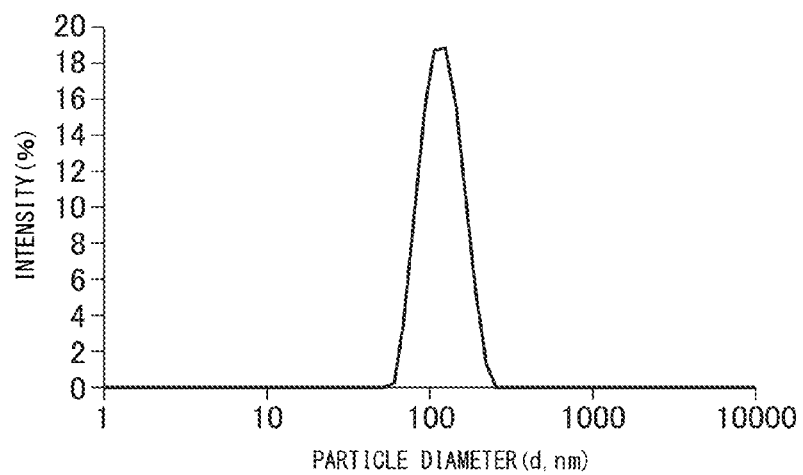
FIG. 40 is a graph showing the particle size distribution of a solution containing the crosslinked vesicles encapsulating β-galactosidase obtained in Example III-1.

The obtained β-galactosidase-encapsulating crosslinked vesicle-containing solution was measured by DLS to determine the particle size distribution, mean particle size and PDI. A graph of the particle size distribution is shown in FIG. 40. Formation of monodisperse particles with a mean particle size of 112 nm was confirmed. The PDI was 0.067.

Preparation and Evaluation of Poorly Water-Soluble Substance-Encapsulating Vesicles X-gal (5-bromo-4-chloro-3-indolyl-β-D-galactopyranoside: water-soluble precursor) was dissolved in a 10 mM phosphate buffer (pH 7.4, 150 mM sodium chloride-containing)/dimethylformamide mixture (4:1) to a concentration of 5 mg/mL, to prepare a solution (the X-gal being converted to an indigo-based dye (5,5'-dibromo-4,4'-dichloro-indigo) by the enzyme action of β-galactosidase). To 50 μL of the crosslinked β-galactosidase-encapsulating vesicle-containing solution with a total polymer concentration of 0.5 mg/mL there was added 10 μL of the X-gal solution, and then 190 μL of 10 mM phosphate buffer was added and the mixture was allowed to stand at 37° C. for 24 hours, to promote conversion reaction from X-gal (water-soluble precursor) to an indigo-based dye (5,5'-dibromo-4,4'-dichloro-indigo: poorly water-soluble substance) by β-galactosidase (enzyme). Next, filtration was performed with a 0.45 μm PES filter, and this was followed by purification by centrifugal ultrafiltration (VIVASPIN 20, product of Sartorius Stedium Biotech, using a molecular cutoff of 300,000; 2000 rpm, 25° C.), to obtain a solution containing indigo-based dye-encapsulating vesicles (poorly water-soluble substance-encapsulating vesicles of Example III-1).

Figure 41:
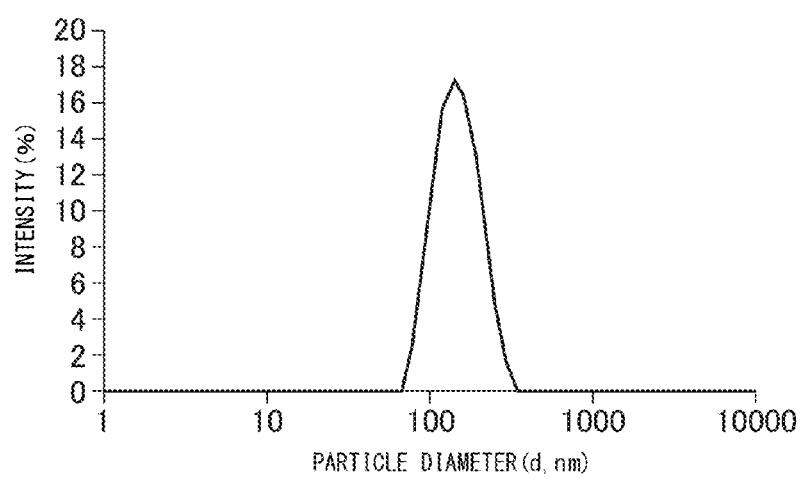
FIG. 41 is a graph showing the particle size distribution of a solution containing the vesicles encapsulating indigo dye obtained in Example III-1.

The obtained indigo-based dye-encapsulating vesicle-containing solution was measured by DLS to determine the particle size distribution, mean particle size and PDI. A graph of the particle size distribution is shown in FIG. 41. Monodisperse particles with a mean particle size of 140 nm were confirmed. The PDI was 0.091.

Figure 42:
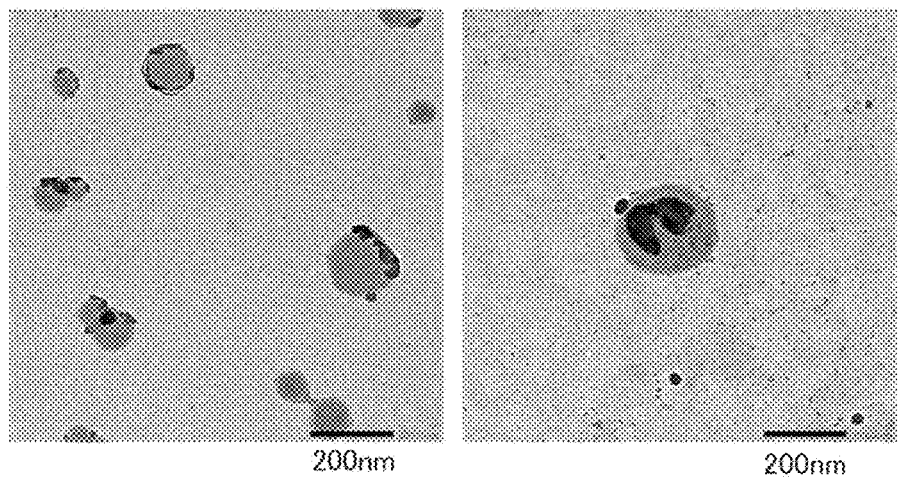
FIG. 42 is a TEM image of the vesicles encapsulating indigo dye obtained in Example III-1.
Figure 43:
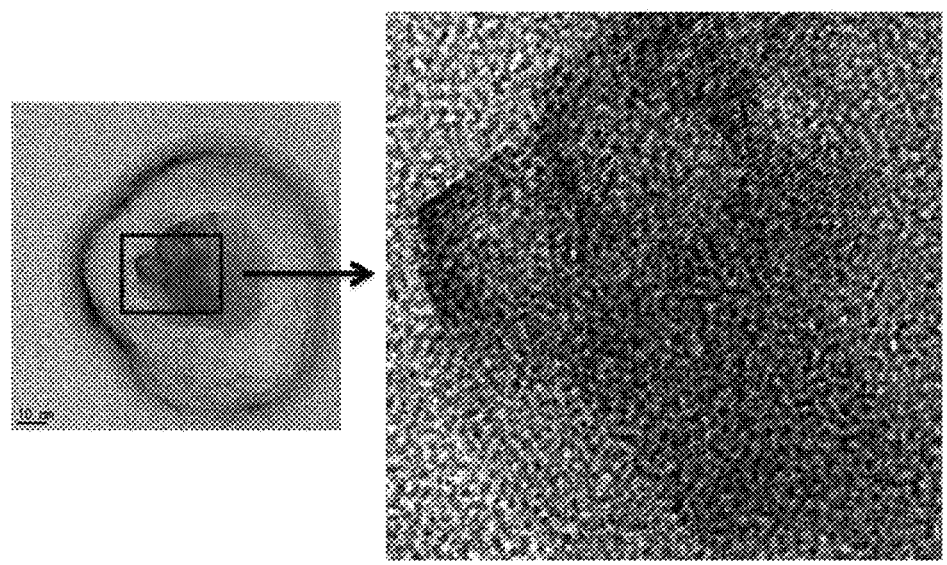
FIG. 43 is a high-resolution TEM image of the vesicles encapsulating indigo dye obtained in Example III-1.

The morphology of the indigo-based dye-encapsulating vesicle-containing solution was also observed with a transmission electron microscope (TEM). The TEM photograph obtained by the TEM (JEM-1400 by JEOL Corp.) is shown in FIG. 42. With FIG. 42 it was confirmed that the indigo-based dye (poorly water-soluble substance) converted from X-gal (water-soluble precursor) by β-galactosidase (enzyme) is localized in the interiors or membranes of the vesicles. Also, a TEM photograph obtained by high-resolution TEM (JEM-2100F by JEOL Corp.) is shown in FIG. 43. In FIG. 43, a diffraction line was observed that was attributable to the indigo-based dye. Thus, the indigo-based dye encapsulated in the vesicles was confirmed to be crystalline.

Also, the indigo-based dye-encapsulating vesicles were allowed to stand overnight in a 90% dimethyl sulfoxide-containing aqueous solution, and the resulting indigo-based dye encapsulation amount was calculated by absorptiometry. As a result, it was confirmed that 66.9% of the indigo-based dye had been encapsulated in the vesicles, with respect to the weight of all the polymers (first and second polymers).

[Comparative Example III-1] Production of Indigo-Based Dye-Encapsulating Vesicles with Free β-Galactosidase A vacant vesicle-containing solution prepared by the same procedure as Example III-1 was directly crosslinked by EDC reaction, without addition and mixing of a β-galactosidase solution, using the same procedure as in Example III-1, to obtain a crosslinked vacant vesicle-containing solution.

Figure 44:
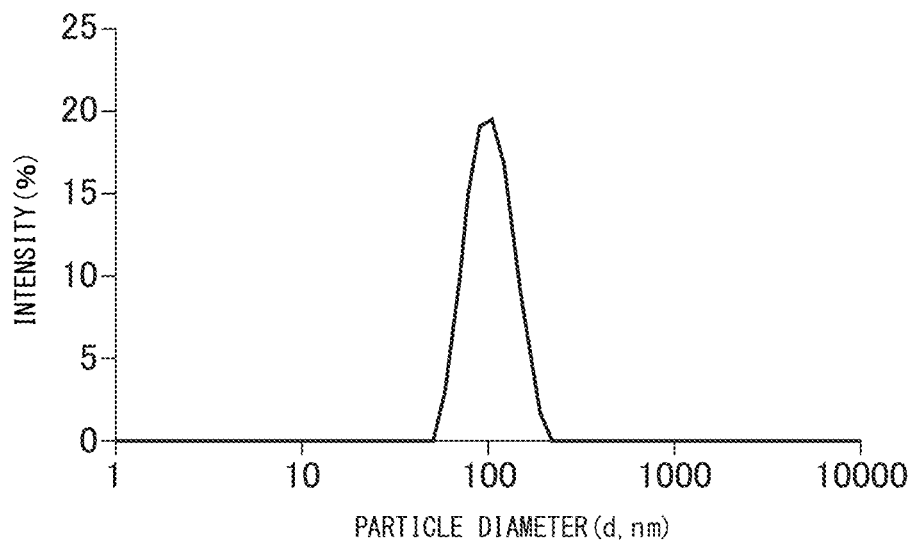
FIG. 44 is a graph showing the particle size distribution of a solution containing the crosslinked vacant vesicles obtained in Comparative Example III-1.

The obtained crosslinked vacant vesicle-containing solution was measured by DLS to determine the particle size distribution, mean particle size and PDI. A graph of the particle size distribution is shown in FIG. 44. Formation of monodisperse particles with a mean particle size of 98 nm was confirmed. The PDI was 0.076.

To 50 μL of the crosslinked vacant vesicle-containing solution with a total polymer concentration of 0.5 mg/mL there were added 12.5 μL of a 1 mg/mL β-galactosidase solution prepared in the same manner as Example III-1, and 10 μL of a 1 mg/mL X-gal solution prepared in the same manner as Example III-1, and then 177.5 μL of 10 mM phosphate buffer was further added and the mixture was allowed to stand at 37° C. for 24 hours. Next, filtration was performed with a 0.45 μm PES filter, and purification was performed by centrifugal ultrafiltration (VIVASPIN 20, product of Sartorius Stedium Biotech, molecular cutoff: 300,000; 2000 rpm, 25° C.), to obtain a indigo-based dye-produced solution containing vacant vesicles (the vesicles that were empty at the start of Comparative Example III-1).

Figure 45:
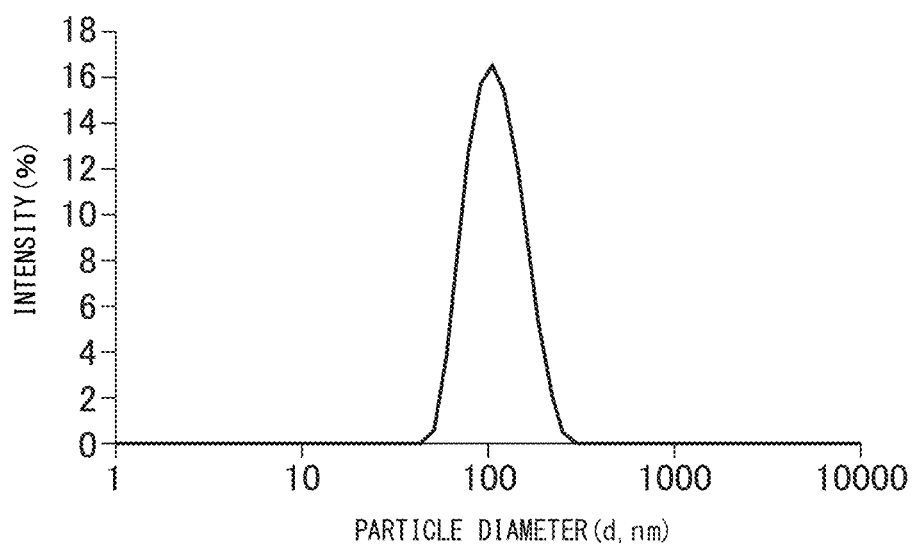
FIG. 45 is a graph showing the particle size distribution of a solution containing the vacant vesicles after production of indigo dye obtained in Comparative Example III-1.

The obtained indigo-based dye-produced solution containing vacant vesicles was measured by DLS to determine the particle size distribution, mean particle size and PDI. A graph of the particle size distribution is shown in FIG. 45. Particles with a mean particle size of 104 nm were confirmed. The PDI was 0.131.

Figure 46:
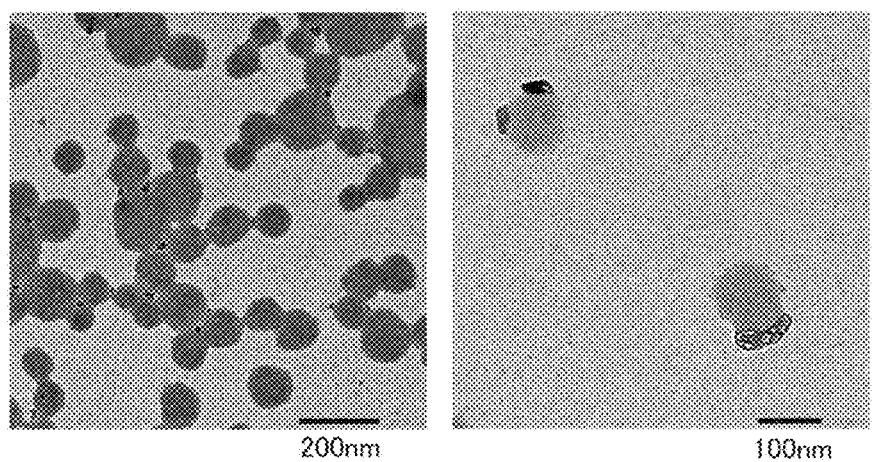
FIG. 46 is a TEM image the vacant vesicles after production of indigo dye obtained in Comparative Example III-1.

The state of the indigo-based dye-produced solution containing vacant vesicles was also observed with a transmission electron microscope (TEM). The TEM photograph obtained by the TEM (JEM-1400 by JEOL Corp.) is shown in FIG. 46. Based on FIG. 46, although a poorly water-soluble indigo-based dye was produced by reaction between β-galactosidase and X-gal, almost no indigo-based dye was found to be encapsulated in the vesicles.

Also, the vacant vesicles after production of the indigo-based dye were allowed to stand overnight in a 90% dimethyl sulfoxide-containing aqueous solution, and the resulting indigo-based dye encapsulation amount was calculated by absorptiometry. As a result, it was confirmed that 31.0% of the indigo-based dye was adhering onto the vesicles, with respect to the weight of all the polymers (first and second polymers). Considering this together with the results of FIG. 46, it is believed that the indigo-based dye adhering to the vesicles was not encapsulated in the vesicles but rather was mainly adhering to the exteriors of the vacant vesicles.

INDUSTRIAL APPLICABILITY

The substance-encapsulating vesicles obtained by the present invention have very high utility, including as a DDS for delivery of a drug, or in the field of biomaterials, functional materials and the like.

What is claimed is:

1. An adsorbent-encapsulating vesicle comprising:
   a vesicle having a membrane comprising a first polymer, which is a block copolymer having a polyethylene glycol segment and a first charged segment, and a second polymer, which has a second charged segment having a charge opposite to the charge of the first charged segment, wherein the first charged segment and the second charged segment are selected from (i) the anionic segment consisting of polyaspartic acid, polyglutamic acid, polycarboxylic acids, and nucleic acids, or (ii) the cationic segment consisting of polyglutamide, polylysine, polyarginine, and polyhistidine, and
   an adsorbent particle encapsulated in the vesicle, wherein at least either the first polymer or the second polymer is adsorbed by the adsorbent particle.

2. The adsorbent-encapsulating vesicle according to claim 1, wherein the first and/or second polymer(s) is(are) crosslinked.

3. The adsorbent-encapsulating vesicle according to claim 1, wherein the adsorbent particle is a silica particle.

4. The adsorbent-encapsulating vesicle according to claim 1, wherein the adsorbent particle has an average particle size of between 40 nm and 10 μm.

5. The adsorbent-encapsulating vesicle according to claim 1, wherein the adsorbent particle has been surface-treated.

6. The adsorbent-encapsulating vesicle according to claim 1, wherein a low-molecular weight compound of 5000 Dalton or less is also adsorbed by the adsorbent particle.

7. A method of producing the adsorbent-encapsulating vesicle of claim 1, said method comprising the steps of:
   (a) mixing one of the first and second polymers with the adsorbent particle to have one of the first and second polymers adsorbed by the adsorbent particle; and
   (b) further mixing the mixture from step (a) with the other of the first and second polymers to form a vesicle composed of a membrane comprising the first and second polymers around the adsorbent particle, thereby forming the adsorbent-encapsulating vesicle.

8. The method according to claim 7, further comprising:
   (c) crosslinking the first and/or the second polymer(s) contained in the vesicle from step (b).

9. The method according to claim 7, wherein the adsorbent particle is a silica particle.

10. The method according to claim 7, wherein the adsorbent particle has an average particle size between 40 nm and 10 μm.

11. The method according to claim 7, further comprising a step of surface-treating the adsorbent particle.

12. The method according to claim 7, wherein a low-molecular weight compound of 5000 Dalton or less is also adsorbed by the adsorbent particle.

13. A drug delivery system comprising the adsorbent-encapsulating vesicle according to claim 1 and a drug adsorbed by the adsorbent particle.

14. An adsorbent-encapsulating vesicle comprising:
   a vesicle having a membrane containing a first polymer and a second polymer,
   and an adsorbent particle encapsulated in the vesicle,
   wherein at least either the first polymer or the second polymer is adsorbed by the adsorbent particle,
   wherein the first polymer is a PEG-anionic segment block copolymer represented by formula (I) or (II), and the second polymer is a PEG-cationic segment block copolymer represented by either formula (III) or (IV) or a cationic copolymer formula (VII) or (VIII), or
   wherein the first polymer is a PEG-cationic segment block copolymer represented by formula (III) or (IV) and the second polymer is a PEG-anionic segment block copolymer represented by either formula (I) or (II) or an anionic polymer represented by formula (V) and/or (VI),

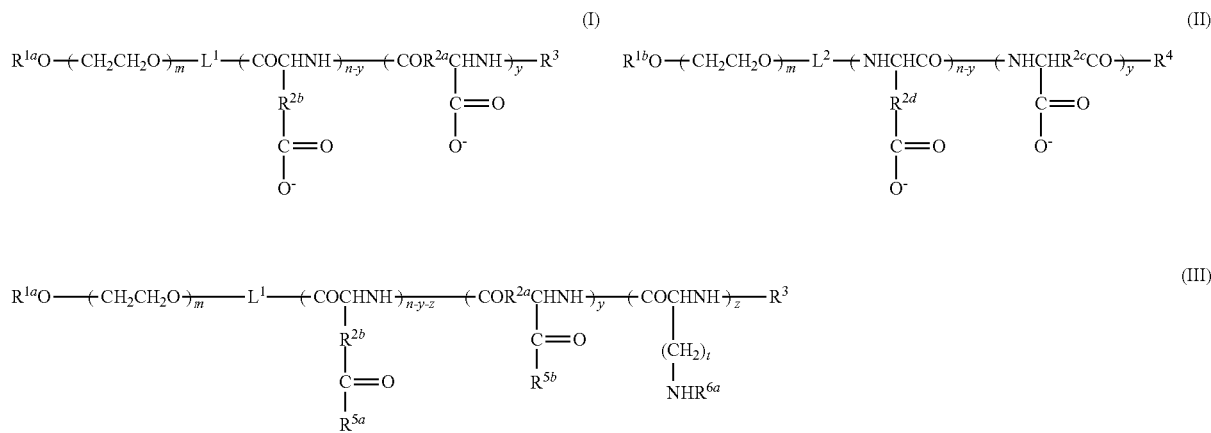

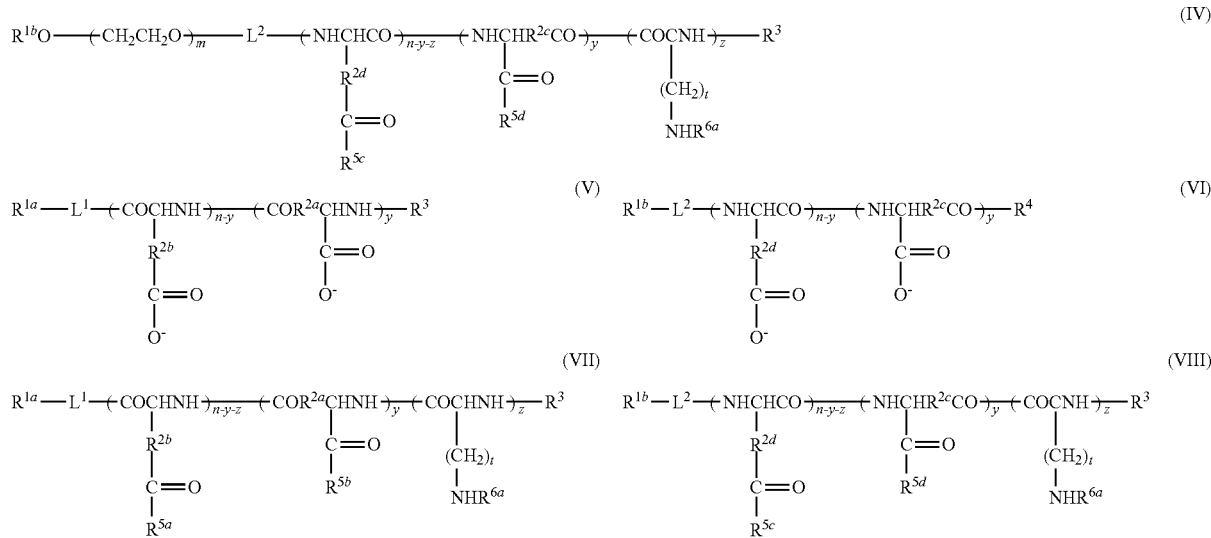

wherein
- $R^{1a}$ and $R^{1b}$ each independently represent hydrogen or $C_{1-12}$ alkyl group, optionally substituted with at least one substituent selected from the group consisting of halogen, aryl, hydroxyl, amino, carboxyl, cyano, formyl, dimethyl acetalated formyl, diethyl acetalated formyl, $C_{1-6}$ alkoxycarbonyl, $C_{2-7}$ acylamide, siloxy, tri($C_{1-6}$ alkyl)siloxy, and silylamino, $L^1$ is —$(CH_2)_b$—NH—, and $L^2$ is —$(CH_2)_c$—CO—, where b and c are independently an integer of 1 to 5,
- $R^{2a}$, $R^{2b}$, $R^{2c}$ and $R^{2d}$ each independently represent a methylene or ethylene group,
- $R^3$ represents a hydrogen atom, acetyl, acryloyl, or methacryloyl group,
- $R^4$ represents hydroxyl, oxybenzyl, or —NH—$R^9$ where $R^9$ represents a straight-chain or branched $C_{1-20}$ alkyl group,
- $R^{5a}$, $R^{5b}$, $R^{5c}$ and $R^{5d}$ each independently represent hydroxyl, oxybenzyl, or —NH—$(CH_2)_a$—X, where X is $(NH(CH_2)_2)_e$—$NH_2$ with the proviso that e is an integer of 0 to 5,
- $R^{6a}$ and $R^{6b}$ each independently represent a hydrogen atom, —C(=NH)$NH_2$ or a protecting group selected from the group consisting of a benzyloxycarbonyl group, Boc group, acetyl group and trifluoroacetyl group,
- m and n are independently an integer of 5 to 2,000,
- t is an integer of 2 to 6,
- y and z are independently an integer of 0 to 5,000.

15. The adsorbent-encapsulating vesicle according to claim 14, wherein the first and/or second polymer(s) is(are) crosslinked.

16. The adsorbent-encapsulating vesicle according to claim 14, wherein the adsorbent particle is a silica particle.

17. The adsorbent-encapsulating vesicle according to claim 14, wherein the adsorbent particle has an average particle size of between 40 nm and 10 μm.

18. The adsorbent-encapsulating vesicle according to claim 14, wherein the adsorbent particle has been surface-treated.

19. The adsorbent-encapsulating vesicle according to claim 14, wherein a low-molecular weight compound of 5000 Dalton or less is also adsorbed by the adsorbent particle.

20. A method of producing the adsorbent-encapsulating vesicle of claim 14, said method comprising the steps of:
 (a) mixing one of the first and second polymers with the adsorbent particle to have one of the first and second polymers adsorbed by the adsorbent particle; and
 (b) further mixing the mixture from step (a) with the other of the first and second polymers to form a vesicle composed of a membrane comprising the first and second polymers around the adsorbent particle, thereby forming the adsorbent-encapsulating vesicle.

21. A drug delivery system comprising the adsorbent-encapsulating vesicle according to claim 14 and a drug adsorbed by the adsorbent particle.

* * * * *